(12) United States Patent
Hiscock et al.

(10) Patent No.: US 9,061,080 B2
(45) Date of Patent: Jun. 23, 2015

(54) HER2 BINDING PEPTIDES LABELED WITH ALUMINIUM-[18] FLUORIDE COMPLEXED BY NOTA

(75) Inventors: Duncan Hiscock, Amersham (GB); Bard Indrevoll, Olso (NO); Peter Iveson, Amersham (GB); Matthias Eberhard Glaser, Amersham (GB); Rajiv Bhalla, Amersham (GB); Anthony Wilson, Waddesdon (GB)

(73) Assignee: GE HEALTHCARE LIMITED, Buckinghamshire (GB)

( * ) Notice: Subject to any disclaimer, the term of this patent is extended or adjusted under 35 U.S.C. 154(b) by 0 days.

(21) Appl. No.: 13/996,109

(22) PCT Filed: Dec. 19, 2011

(86) PCT No.: PCT/US2011/065794
§ 371 (c)(1),
(2), (4) Date: Jun. 20, 2013

(87) PCT Pub. No.: WO2012/087908
PCT Pub. Date: Jun. 28, 2012

(65) Prior Publication Data
US 2013/0287685 A1 Oct. 31, 2013

Related U.S. Application Data

(63) Continuation-in-part of application No. 12/975,425, filed on Dec. 22, 2010.

(60) Provisional application No. 61/438,297, filed on Feb. 1, 2011, provisional application No. 61/510,520, filed on Jul. 22, 2011, provisional application No. 61/541,287, filed on Sep. 30, 2011.

(51) Int. Cl.
*A61K 51/00* (2006.01)
*A61M 36/14* (2006.01)
*A61K 51/08* (2006.01)
*C07K 14/71* (2006.01)

(52) U.S. Cl.
CPC ............... *A61K 51/088* (2013.01); *C07K 14/71* (2013.01)

(58) Field of Classification Search
CPC ........... A61K 2123/00; A61K 2121/00; A61K 51/00; A61K 51/08; A61K 51/088; A61K 38/00; C07K 1/1075; C07K 1/04; C07K 1/00; C07K 1/107; C07K 14/475; C07K 14/71
USPC ............. 424/1.11, 1.65, 1.69, 1.81, 1.85, 9.3, 424/9.37, 9.4, 9.5, 9.6; 514/1, 1.1; 534/7, 534/10–16; 530/300, 324, 333
See application file for complete search history.

(56) References Cited

U.S. PATENT DOCUMENTS 7,597,876 B2 * 10/2009 McBride et al. ............. 424/1.89
2009/0299033 A1 12/2009 McBride et al.

FOREIGN PATENT DOCUMENTS

| WO | 2005/003156 | 1/2005 |
| WO | 2008/049866 | 5/2008 |
| WO | 2008/118601 | 10/2008 |
| WO | 2009/080810 | 7/2009 |

OTHER PUBLICATIONS

McBride et al, Bioconjugate Chemistry, Jul. 21, 2010, vol. 21, No. 7, pp. 1331-1340.*
McBride, et.al. Bioconjugate Chemistry 20100721 American Chemical Society, vol. 21, No. 7, Jul. 21, 2010, pp. 1331-1340.
Heskamp, et.al., Journal of Nucleare Medicine 20120101 Society of Nuclear Medicine Inc. vol. 53, No. 1, Jan. 1, 2012 pp. 146-153.
PCT/US2011/065794 ISRWO Dated Mar. 1, 2012.

* cited by examiner

*Primary Examiner* — D L Jones
(74) *Attorney, Agent, or Firm* — Collen A. Beard; Parks Wood LLC

(57) ABSTRACT

Imaging agents comprising an isolated polypeptide conjugated with a radionucleide and a chelator; wherein the isolated polypeptide binds specifically to HER2, or a variant thereof; and methods for preparing and using these imaging agents.

5 Claims, 34 Drawing Sheets

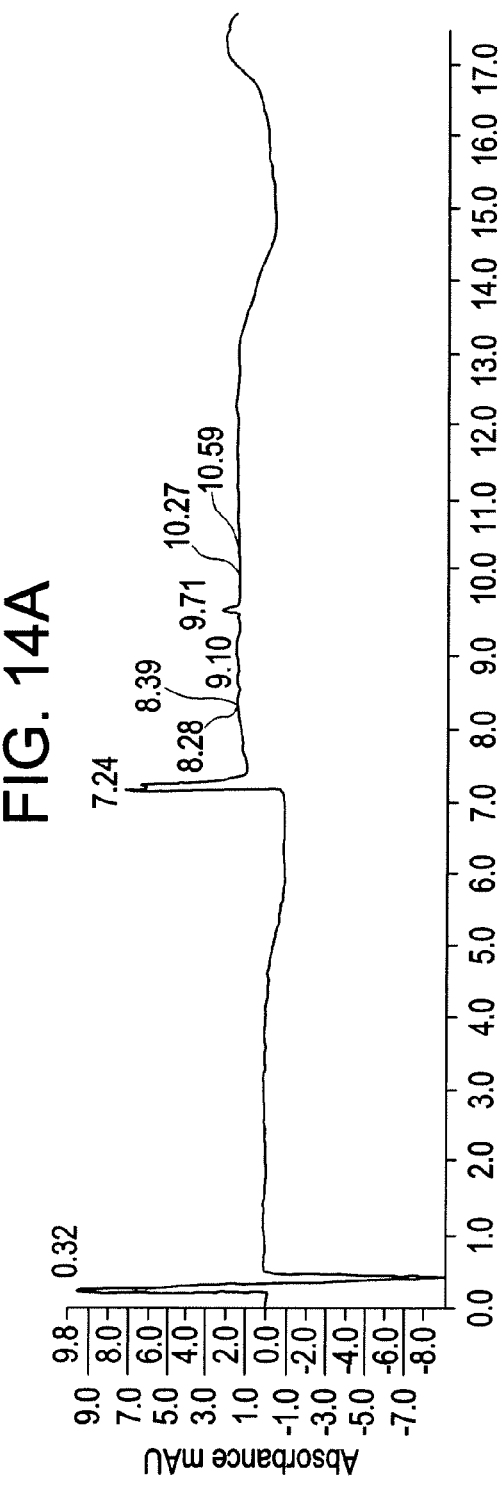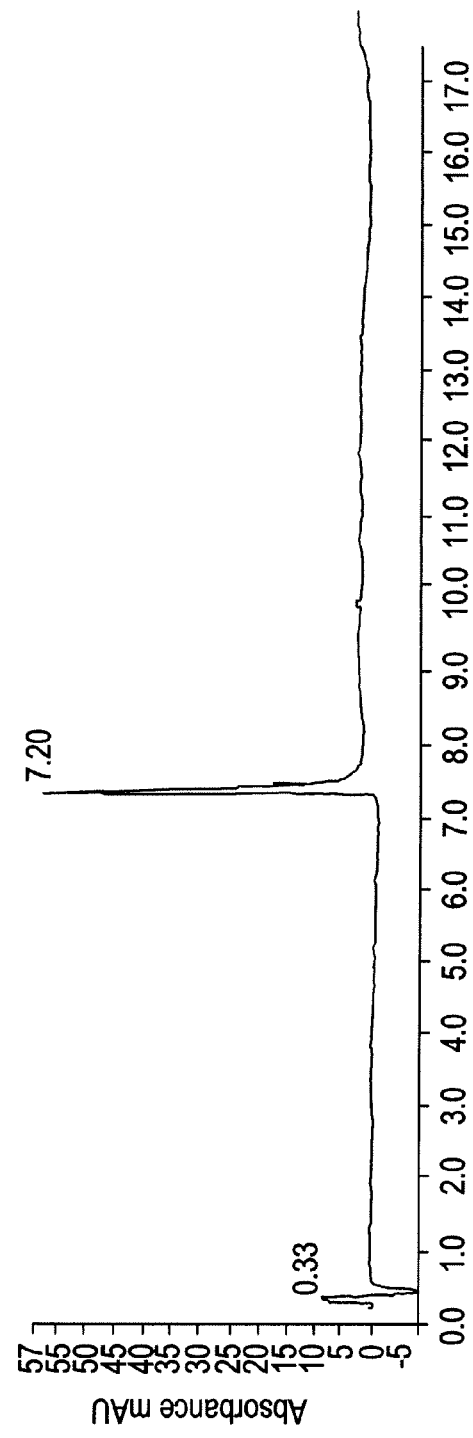

FIG. 31
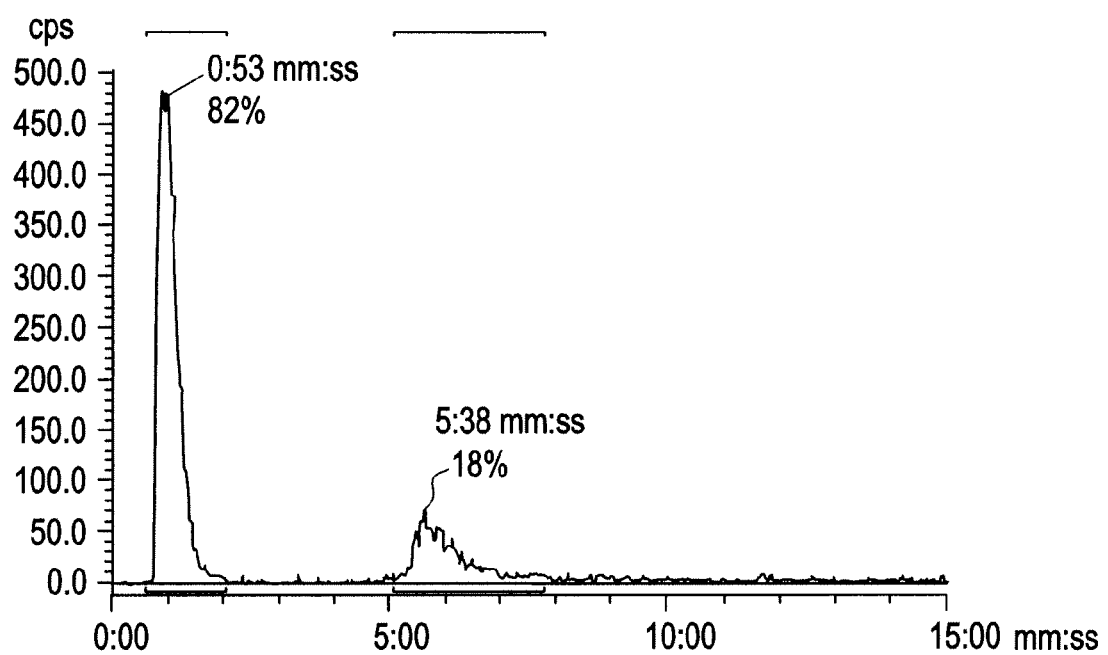
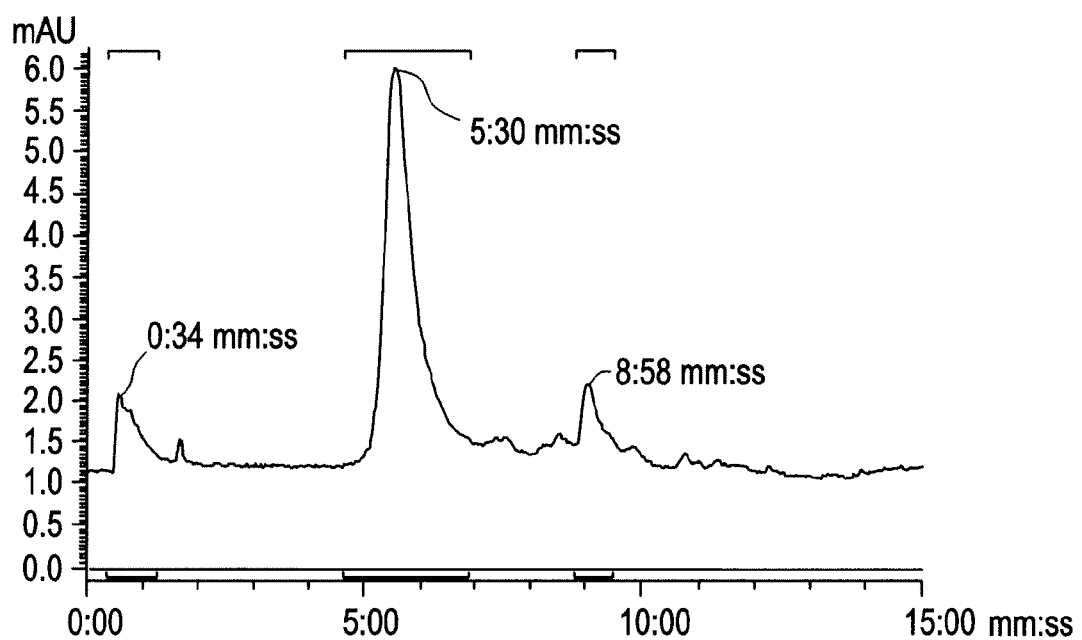

FIG. 38
A.2 – Imaging dual tumor model
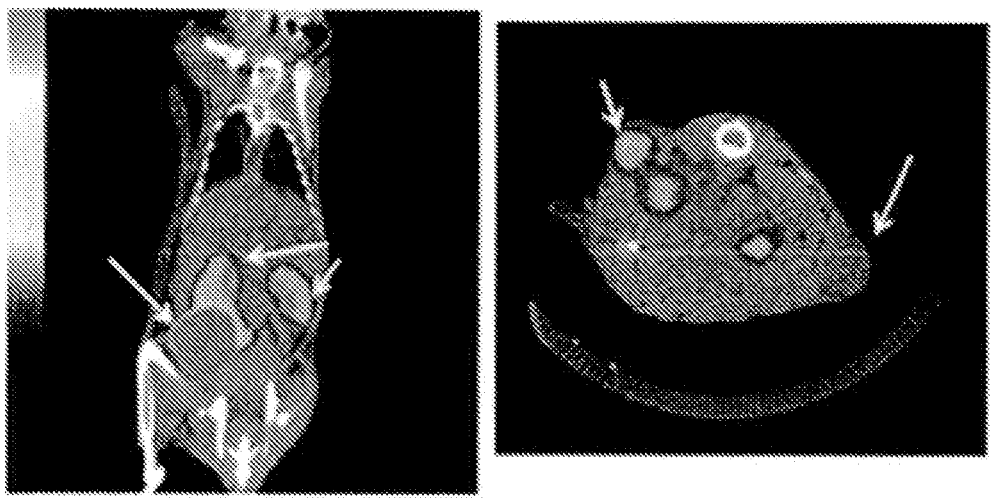
B.9 – Imaging study
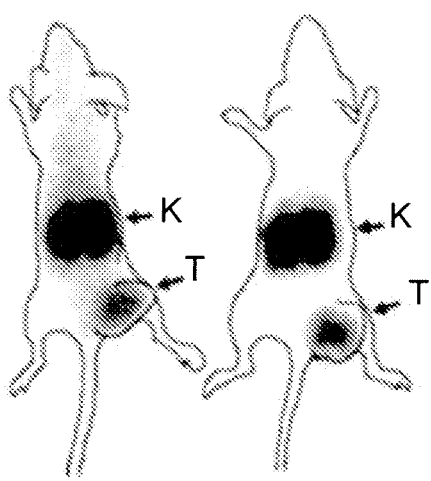
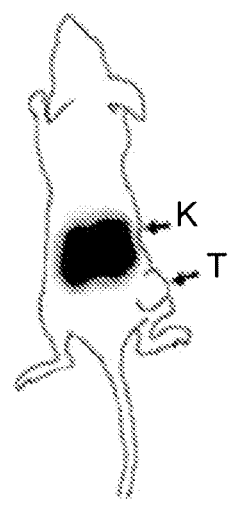
SKOV3 (high HER2)            A431 (low HER2)

HER2 BINDING PEPTIDES LABELED WITH ALUMINIUM-[18] FLUORIDE COMPLEXED BY NOTA

This application is a filing under 35 U.S.C. 371 of International Application No. PCT/US2011/065794, filed Dec. 19, 2011, and is a CIP of U.S. Application No. 12/975,425, filed Dec. 22, 2010 and also claims priority to U.S. Provisional Application No. 61/438,297, filed Feb. 1, 2011 and to U.S. Provisional Application No. 61/510,520, filed Jul. 22, 2011 and to U.S. Provisional Application No. 61/541,287, filed Sep. 30, 2011, the entireties of which are hereby incorporated by reference.

FIELD

The invention relates generally to imaging agents that bind to human epidermal growth factor receptor type 2 (HER2) and methods for making and using such agents.

BACKGROUND

Human epidermal growth factor receptor type 2 (HER2) is a transmembrane protein and a member of erbB family of receptor tyrosine kinase proteins. HER2 is a well-established tumor biomarker that is over-expressed in a wide variety of cancers, including breast, ovarian, lung, gastric, and oral cancers. Therefore, HER2 has great value as a molecular target and as a diagnostic or prognostic indicator of patient survival, or a predictive marker of the response to antineoplastic surgery.

Over the last decade, noninvasive molecular imaging of HER2 expression using various imaging modalities has been extensively studied. These modalities include radionuclide imaging with Positron Emission Tomography (PET) and Single Photon Emission Tomography (SPECT). PET and SPECT imaging of HER2 (HER2-PET and HER2-SPECT, respectively) provide high sensitivity, high spatial resolution. PET imaging of HER2 also provides strong quantification ability. HER2-PET and HER2-SPECT are particularly useful in real-time assays of overall tumor HER2 expression in patients, identification of HER2 expression in tumors over time, selection of patients for HER-targeted treatment (e.g., trastuzumab-based therapy), prediction of response to therapy, evaluation of drug efficacy, and many other applications. However, no PET or SPECT-labeled HER2 ligands have been developed that have a chemistry and exhibit in vivo behaviors which would be suitable for clinical applications.

Naturally occurring Staphylococcal protein A comprises domains that form a three-helix structure (a scaffold) that binds to the fragment, crystallizable region (Fc) of immunoglobulin isotype G (IgG). Certain polypeptides, derived from the Z-domain of protein A, contain a scaffold composed of three α-helices connected by loops. Certain amino acid residues situated on two of these helices constitute the binding site for the Fc region of IgG. Alternative binder molecules have been prepared by substituting surface-exposed amino acid residues (13 residues) situated on helices 1 and 2, to alter the binding ability of these molecules. One such example is HER2 binding molecules or HER2 binders. These HER2 binders have been labeled with PET or SPECT-active radionuclides. Such PET and SPECT-labeled binders provide the ability to measure in vivo HER2 expression patterns in patients and would therefore aid clinicians and researchers in diagnosing, prognosing, and treating HER2-associated disease conditions.

HER2 binding Affibody® molecules, radiolabeled with the PET-active radionucleide, $^{18}$F, have been evaluated as imaging agents for malignant tumors that over express HER2. HER2 binding Affibody® molecules, conjugated with $^{99m}$Tc via the chelators such as maGGG (mercaptoacetyltriglycyl), CGG (cysteine-diglycyl), CGGG (SEQ ID NO: 6) (cysteine-triglycyl) or AA3, have also been used for diagnostic imaging. The binding of these molecules to target HER2 expressing tumors has been demonstrated in mice.

In most of the cases, the signal-generating $^{18}$F group is introduced to the Affibody® through a thiol-reactive maleimide group. The thiol reactive maleimide group is prepared using a multi-step synthesis after $^{18}$F incorporation. However, this chemistry only provides a low radiochemical yield. Similarly, the conjugation of $^{99m}$Tc with the Affibody® is a multistep process. In addition, Tc reduction and the complex formation with chelates, require high pH (e.g., pH=11) conditions and long reaction times.

Though the in vivo performance of $^{18}$F labeled Affibody® molecules was moderately good, there is significant room for improvement. For example, in some studies, the tumor uptake was found to be only 6.36±1.26% ID/g 2 hours post-injection of the imaging agent.

Therefore, there is a need for chemistries and methods for synthesizing radiolabeled polypeptides in which a radioactive moiety, such as, for example, $^{18}$F, can be introduced at the final stage, which in turn will provide high radiochemical yields. In addition, there is a need for a new HER2 targeting imaging agent for PET or SPECT imaging with improved properties particularly related to renal clearance and toxicity effects.

SUMMARY OF THE INVENTION

The compositions of the invention are a new class of imaging agents that are capable of binding specifically to HER2 or variants thereof.

In one or more embodiments, the imaging agent composition comprises an isolated polypeptide comprising SEQ. ID No. 1, SEQ. ID. No 2 or a conservative variant thereof, conjugated with a $^{99m}$Tc via a diaminedioxime chelator. The diaminedioxime chelator may comprise Pn216, cPn216, Pn44, or derivatives thereof. The isolated polypeptide binds specifically to HER2 or variants thereof.

In one or more embodiments, the imaging agent composition comprises an isolated polypeptide comprising SEQ. ID No. 1, SEQ. ID. No 2 or a conservative variant thereof, conjugated with $^{67}$Ga or $^{68}$Ga via a NOTA chelator. The isolated polypeptide binds specifically to HER2 or variants thereof.

In one or more embodiments, the imaging agent composition comprises an isolated polypeptide comprising SEQ. ID No. 1, SEQ. ID. No 2 or a conservative variant thereof, conjugated with an Al$^{18}$F-NOTA chelate. The isolated polypeptide binds specifically to HER2 or variants thereof.

In one or more embodiments, the imaging agent composition comprises an isolated polypeptide comprising SEQ. ID No. 1, SEQ. ID. No 2 or a conservative variant thereof, conjugated with $^{18}$F via a linker. The linker comprises a group derived from an aminoxy group, an azido group, or an alkyne group. The isolated polypeptide binds specifically to HER2 or variants thereof.

In one or more embodiments, the imaging agent composition comprises an isolated polypeptide comprising SEQ. ID No. 1, SEQ. ID. No 2 or a conservative variant thereof, conjugated with $^{18}$F via an isotopic fluorine exchange chemistry. The isolated polypeptide binds specifically to HER2 or variants thereof.

In one or more embodiments, methods of making an imaging agent composition as described herein are provided. An example of a method of the invention, for preparing an imaging agent composition, comprises (i) providing an isolated polypeptide comprising SEQ. ID No. 1, SEQ. ID No. 2 or a conservative variant thereof; and (ii) reacting a diaminedioxime chelator with the polypeptide to form a chelator conjugated polypeptide. In another example, the method comprises (i) providing an isolated polypeptide comprising SEQ. ID No. 1, SEQ. ID No. 2 or a conservative variant thereof; (ii) reacting the polypeptide with a linker; and (iii) reacting the linker with an $^{18}$F moiety to form a $^{18}$F conjugated polypeptide. The linker may comprise an aminoxy group, an azido group, or an alkyne group.

In another example, the method comprises (i) providing an isolated polypeptide comprising SEQ. ID No. 1, SEQ. ID No. 2 or a conservative variant thereof; (ii) reacting the polypeptide with a NOTA-chelator to form, respectively, a NOTA-chelator conjugated polypeptide and (iii) reacting the NOTA-chelator conjugated polypeptide with an Al$^{18}$F moiety to form, a Al$^{18}$F-NOTA chelator conjugated polypeptide.

In another example, the method comprises (i) providing an isolated polypeptide comprising SEQ. ID No. 1, SEQ. ID No. 2 or a conservative variant thereof; (ii) reacting the polypeptide with a silicon fluoride (e.g. [$^{19}$F]-silicon fluoride)-containing moiety to form a silicon fluoride conjugated polypeptide; and (iii) reacting the silicon fluoride conjugated polypeptide with an $^{18}$F moiety to form an $^{18}$F-silicon fluoride conjugated polypeptide.

BRIEF DESCRIPTION OF THE DRAWINGS

These and other features, aspects, and advantages of the present invention will become better understood when the following detailed description is read with reference to the accompanying figures wherein:

FIG. 14A is the reverse phase HPLC chromatogram of Z00342 (SEQ. ID No. 1) starting material and 14B is the reverse phase HPLC chromatogram of the purified Z00342 (SEQ. ID No. 1)-AO imaging agent composition, both analyzed at 280 nm.

FIG. 31 is an analytical HPLC profile of a labelling mixture of 5. (Top trace: radioactivity channel, bottom trace: UV channel at 280 nm).

FIG. 38 shows preliminary imaging with 2 in the dual tumour xenograft model (A) and comparison to Affibody® 9 imaging study (B).

DETAILED DESCRIPTION

Figure 1A:
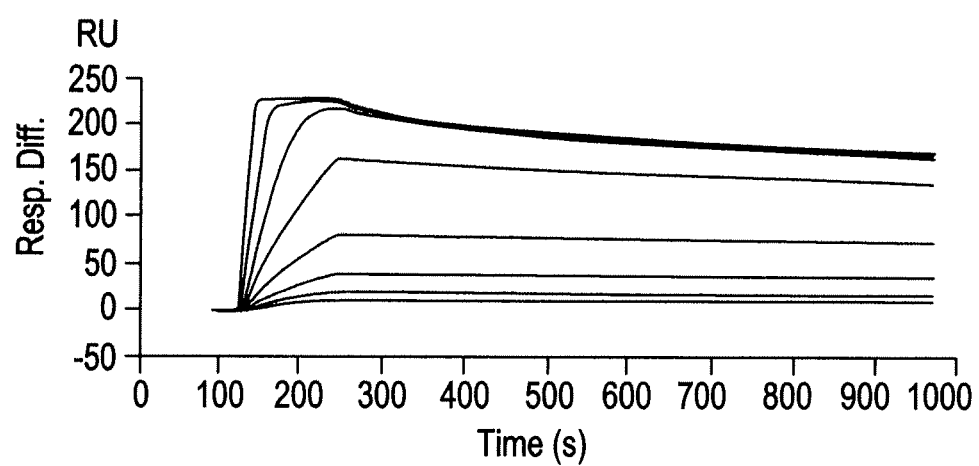
FIGS. 1A and 1B are graphs of the surface plasmon resonance (SPR) of the binding affinity of two anti-HER2 polypeptides, Z477 (SEQ. ID No. 3) and (Z477)$_2$ (SEQ. ID No. 5), respectively, at eight different concentrations, to human HER2.

The imaging agent compositions of the invention generally comprise an isolated polypeptide of SEQ. ID No. 1, SEQ. ID No. 2 or a conservative variant thereof, conjugated with a radioisotope such as, for example, $^{18}$F, $^{99m}$Tc, $^{67}$Ga or $^{68}$Ga, $^{111}$In, $^{123}$I, $^{124}$I, $^{89}$Zr, or $^{64}$Cu; and methods for making and using the compositions. The isolated polypeptide binds specifically to HER2 or its variant thereof. In one or more embodiments, the sequence of the isolated polypeptide has at least 90% sequence similarity to any of SEQ. ID No. 1, SEQ. ID No. 2 or conservative variant thereof.

The isolated polypeptide may comprise natural amino acids, synthetic amino acids, or amino acid mimetics that function in a manner similar to the naturally occurring amino acids. Naturally occurring amino acids are those encoded by the genetic code, as well as those amino acids that are later modified, for example, hydroxyproline, γ-carboxyglutamate, O-phosphoserine, phosphothreonine, and phosphotyrosine.

The isolated polypeptides may be prepared using standard solid phase synthesis techniques. Alternatively, the polypeptides may be prepared using recombinant techniques. When the polypeptides are prepared using recombinant techniques, the DNA encoding the polypeptides or conservative variants thereof may be isolated. The DNA encoding the polypeptides or conservative variants thereof may be inserted into a cloning vector, introduced into a host cell (e.g., a eukaryotic cell, a plant cell, or a prokaryotic cell), and expressed using any art recognized expression system.

The polypeptide may be substantially comprised of a single chiral form of amino acid residues. Thus, polypeptides of the invention may be substantially comprised of either L-amino acids or D-amino acids; although a combination of L-amino acids and D-amino acids may also be employed.

As the polypeptides provided herein are derived from the Z-domain of protein A, residues on the binding interface may be non-conservatively substituted or conservatively substituted while preserving binding activity. In some embodiments, the substituted residues may be derived from any of the 20 naturally occurring amino acids or any analog thereof.

The polypeptides may be about 49 residues to about 130 residues in length. The specific polypeptide sequences are listed in Table 1.

TABLE 1

| Name | Sequence | Length |
|---|---|---|
| Z00342 (SEQ. ID No. 1) | VENKFNKEMRNAYWEIALLPNLNN QQKRAFIRSLYDDPSQSANLLAEAK KLNDAQAPK | 58 |
| Z02891 (SEQ. ID No. 2) | AEAKYAKEMRNAYWEIALLPNLTN QQKRAFIRKLYDDPSQSSELLSEAK KLNDSQAPKVDC | 61 |
| Z00477 (SEQ. ID No. 3) | VDNKFNKEMRNAYWEIALLPNLNV AQKRAFIRSLYDDPSQSANLLAEAK KLNDAQAPKVDC | 61 |
| Z00477-His6 (SEQ. ID No. 4) ('His6' disclosed as SEQ ID NO: 7) | GSSHHHHHHLQVDNKFNKEMRNA YWEIALLPNLNVAQKRAFIRSLYDD PSQSANLLAEAKKLNDAQAPKVDC | 72 |
| (Z00477)$_2$ (SEQ. ID No. 5) | GSSHHHHHHLQVDNKFNKEMRNA YWEIALLPNLNVAQKRAFIRSLYDD PSQSANLLAEAKKLNDAQAPKVDN KFNKEMRNAYWEIALLPNLNVAQK RAFIRSLYDDPSQSANLLAEAKKLN DAQAPKVDC | 130 |

Additional sequences may be added to the termini to impart selected functionality. Thus, additional sequences may be appended to one or both termini to facilitate purification or isolation of the polypeptide, alone or coupled to a binding target (e.g., by appending a His tag to the polypeptide).

The polypeptides listed in Table 1 may be conjugated with $^{18}$F via a linker; $^{99m}$Tc via a diaminedioxime chelator, with $^{67}$Ga or $^{68}$Ga via a NOTA chelator, with $^{18}$F via an Al$^{18}$F-NOTA-chelator, with $^{18}$F via SiFA (i.e., silicon fluoride acceptor) or silicon fluoride exchange chemistry, with $^{111}$In via DOTA chelator chemistry, with $^{123}$I or $^{124}$I via fluorobenzaldehyde-like chemistry using iodobenzaldehyde, or with $^{64}$Cu via NOTA-chelator chemistry. Table 2 provides the isoelectric point (pI), of these polypeptides.

TABLE 2

|  | pI | MW (kD) |
| --- | --- | --- |
| His6-Z00477 (SEQ. ID No. 4) ('His6' disclosed as SEQ ID NO: 7) | 8.31 | 8143.11 |
| Z02891(SEQ. ID No. 2) | 8.10 | 7029.96 |
| His6-Z00342 ('His6' disclosed as SEQ ID NO: 7) | 8.14 | 8318.27 |

In one or more embodiments, the isolated polypeptide, comprising SEQ. ID No. 1, SEQ. ID No. 2 or a conservative variant thereof, may be conjugated with $^{18}$F. The $^{18}$F may be incorporated at a C terminus, at a N-terminus, or at an internal position of the isolated polypeptide.

In one or more embodiments, the $^{18}$F may be conjugated to the isolated polypeptide via a linker. The linker may comprise, an aminoxy group, an azido group, or an alkyne group. The aminoxy group of the linker may be attached with an aldehyde, such as a fluorine-substituted aldehyde. An azide group of the linker may be attached with a fluorine substituted alkyne. Similarly, an alkyne group of the linker may be attached with a fluorine substituted azide. The linker may also comprise a thiol reactive group. The linker may comprise of a maleimido-aminoxy, maleimido-alkyne or maleimido-azide group. The $^{18}$F conjugated polypeptide may be prepared by: (i) providing the isolated polypeptide comprising SEQ. ID No. 1, SEQ. ID No. 2, or a conservative variant thereof; (ii) reacting the polypeptide with a linker, wherein the linker comprises an aminoxy group, an azido group, or an alkyne group, to form a linker conjugated polypeptide; and reacting the linker with an $^{18}$F moiety to form the $^{18}$F conjugated polypeptide.

The $^{18}$F conjugated polypeptide may be prepared by: (i) providing the isolated polypeptide comprising SEQ. ID No. 1, SEQ. ID No. 2, or a conservative variant thereof; (ii) reacting the polypeptide with a linker, wherein the linker comprises a maleimido-aminoxy, maleimido-alkyne or maleimido-azide group, to form a linker conjugated polypeptide; and reacting the linker with an $^{18}$F moiety to form the $^{18}$F conjugated polypeptide.

In another embodiment, the method may comprise: (i) providing an isolated polypeptide comprising SEQ. ID No. 1, SEQ. ID No. 2, or a conservative variant thereof; (ii) providing a linker; (iii) reacting the linker with the $^{18}$F moiety to form a $^{18}$F labeled linker; and (iv) reacting the $^{18}$F labeled linker with the isolated polypeptide of SEQ. ID No 1, SEQ ID no 2, or a conservative variant thereof, to form the $^{18}$F conjugated polypeptide.

Using the above-described examples, fluorine or radiofluorine atom(s), such as $^{18}$F, may be introduced onto the polypeptides. A fluorine-substituted polypeptide results when a fluorine-substituted aldehyde is reacted with the aminoxy group of the linker conjugated polypeptide. Similarly, a fluorine substituted polypeptide results, when a fluorine substituted azide or alkyne group is reacted with the respective alkyne or azide group of the linker conjugated polypeptide. A radiofluorine-labeled polypeptide or imaging agent composition results, when a radiofluorine-substituted aldehyde, azide or alkyne is reacted with the respective aminoxy, alkyne or azide group of the linker conjugated polypeptide. Further, the linker may have a radiofluorine ($^{18}$F) to prepare radiofluorine-labeled imaging agent compositions. The methods for introducing fluorine onto the polypeptide may also be used to prepare a fluorinated imaging agent composition of any length. Thus, in some embodiments the polypeptide of the imaging agent composition may comprise, for example, 40 to 130 amino acid residues.

A linker-conjugated polypeptide or the $^{18}$F-conjugated linker for use in the preparation of an imaging agent or imaging agent composition of the invention may be prepared by a method of the invention that is more efficient than previously known methods and result in higher yields. The methods are easier to carry out, faster and are performed under milder, more user friendly, conditions. For example, the method for labeling a polypeptide with an $^{18}$F-conjugated linker (e.g., $^{18}$F-fluorobenzaldehyde)("$^{18}$F-FBA") is simpler than the procedures known in the art. $^{18}$F conjugated-linker is prepared in one step by the direct nucleophilic incorporation of $^{18}$F onto the trimethylanilinium precursor. $^{18}$F-linker (i.e., $^{18}$F-FBA) is then conjugated to the polypeptide, such as, for example, an Affibody® and those described herein. The preparation of the linker is also easier than previously known methods in the art. Moreover, radiolabeled aminoxy based linker-conjugated polypeptides, and the cPn family of chelator conjugated polypeptides (e.g., Affibody®), show significantly better biodistribution and better tumor uptake, as well as better clearance with less liver uptake.

The fluorine-labeled imaging agent compositions are highly desired materials in diagnostic applications. $^{18}$F labeled imaging agent compositions may be visualized using established imaging techniques such as PET.

In another embodiment, the polypeptide may be conjugated with $^{99m}$Tc via a diamindioxime chelator of formula (I).

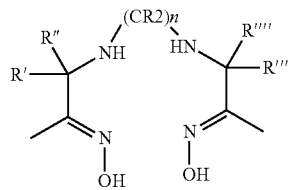

wherein R', R'', R''', R'''' is independently H or $C_{1-10}$ alkyl, $C_{3-10}$ alkylary, $C_{2-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached to form a carbocyclic, heterocyclic, saturated or unsaturated ring, wherein R may be H, $C_{1-10}$ alkyl, $C_{3-10}$ alkylary, $C_{2-10}$ alkoxyalkyl, $C_{1-10}$ hydroxyalkyl, $C_{1-10}$ alkylamine, or $C_{1-10}$ fluoroalkyl. In one embodiment, n may vary from 0-5. Examples of methods for preparing diaminedioxime chelators are described in PCT Application, International Publication No. WO2004080492 (A1) entitled "Methods of radio fluorination of biologically active vector", and PCT Application, International Publication No. WO2006067376(A2) entitled "Radio labelled conjugates of RGD-containing peptides and methods for their preparation via click-chemistry", which are incorporated herein by references.

The $^{99m}$Tc may be conjugated to the isolated polypeptide via the diamindioxime at the N-terminus of the isolated polypeptide. The chelator may be a bifunctional compound. In one embodiment, the bifunctional compound may be Mal-cPN216. The Mal-cPN216 comprises a thiol-reactive maleimide group for conjugation to a terminal cysteine of the polypeptide of SEQ ID No. 1 or SEQ ID No 2 and a bis-aminoxime group (diamindioxime chelator) for chelating with $^{99m}$Tc. The Mal-cPN216 may have a formula (II).

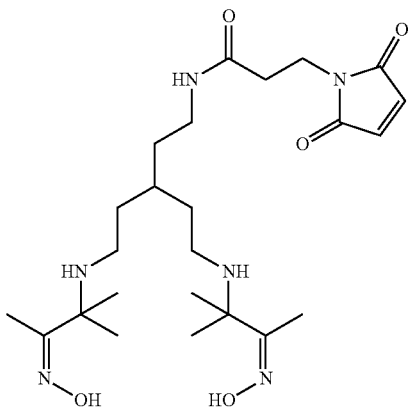 [SMILES: C/C(=N/O)C(C)(C)NCCC(CCNC(=O)CCN1C(=O)C=CC1=O)CCNC(C)(C)/C(C)=N\O]

The diamindioxime chelator conjugated peptide may be prepared by (i) providing an isolated polypeptide comprising SEQ. ID No. 1, SEQ. ID No. 2 or a conservative variant thereof, (ii) reacting a diamindioxime chelator with the polypeptide to form the diamindioxime conjugated polypeptide. The diamindioxime chelator may be further conjugated with $^{99m}$Tc.

In one or more embodiments, the polypeptide may be conjugated with $^{67}$Ga, or $^{68}$Ga via NOTA (1,4,7-triazacyclononane-N,N',N''-triacetic acid) chelator. The NOTA-chelator conjugated polypeptide may be prepared by (i) providing an isolated polypeptide comprising SEQ. ID No. 1, SEQ. ID No. 2 or a conservative variant thereof, (ii) reacting a NOTA chelator with the polypeptide to form the NOTA-chelator conjugated polypeptide. The NOTA chelator may be further conjugated with $^{67}$Ga or $^{68}$Ga.

In one embodiment, the Ga, specifically $^{67}$Ga, may be conjugated to the isolated polypeptide via NOTA chelator. The NOTA chelator may be functionalized with a maleimido group, as described in formula (III).

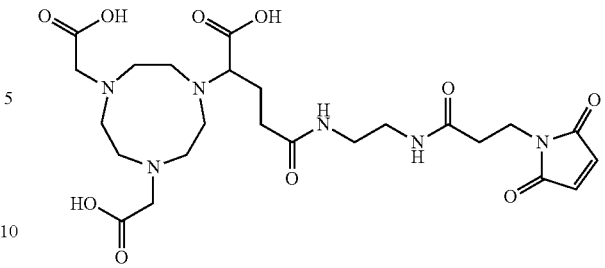

In one or more embodiments, the polypeptide may be conjugated with Al$^{18}$F via NOTA (1,4,7-thazacyclononane-N,N',N''-triacetic acid) chelator The NOTA-conjugated polypeptide may be prepared by (i) providing an isolated polypeptide comprising SEQ. ID No. 1, SEQ. ID No. 2 or a conservative variant thereof, (ii) reacting a NOTA-chelator with the polypeptide to form the NOTA-chelator conjugated polypeptide. The NOTA-chelator conjugated polypeptide may then be further conjugated with Al$^{18}$F to form the Al$^{18}$F-NOTA-chelator conjugated polypeptide.

In one or more embodiments, the polypeptide may be conjugated with $^{18}$F via NOTA-chelator. The NOTA-chelator conjugated polypeptide may be prepared by (i) providing an isolated polypeptide comprising SEQ. ID No. 1, SEQ. ID No. 2 or a conservative variant thereof, (ii) reacting a NOTA-chelator with a source of $^{18}$F (e.g., Al$^{18}$F) to form an $^{18}$F-NOTA-chelator; and (iii) reacting the $^{18}$F-NOTA-chelator with the isolated polypeptide to form the $^{18}$F-NOTA-chelator conjugated polypeptide.

In one or more embodiments, a chelator may comprise a chelate moiety (e.g. NOTA, DOTA) alone or a chelate moiety and a linker, each as described herein. By way of example, a NOTA-chelator can represent a NOTA chelate moiety alone or a NOTA chelate moiety attached to a linker as described herein.

In one or more embodiments, the polypeptide may be conjugated with $^{18}$F via SiFA chemistry. The $^{18}$F-SiFA conjugated polypeptide may be prepared by: (i) providing the isolated polypeptide comprising SEQ. ID No. 1, SEQ. ID No. 2, or a conservative variant thereof; (ii) reacting the polypeptide with a linker, wherein the linker comprises a silicon fluoride acceptor (SiFA) group, to form a SiFA conjugated polypeptide; and (iii) reacting the SiFA conjugated polypeptide with an $^{18}$F moiety or a source of $^{18}$F. The $^{18}$F moiety or source of $^{18}$F can any such moiety or source capable of reacting with a SiFA group and undergo isotopic fluorine exchange chemistry. Scheme I below illustrates radiolabelling of Z02891 (SEQ. ID No. 2) using [$^{18}$F]SiF coupling:

Scheme I

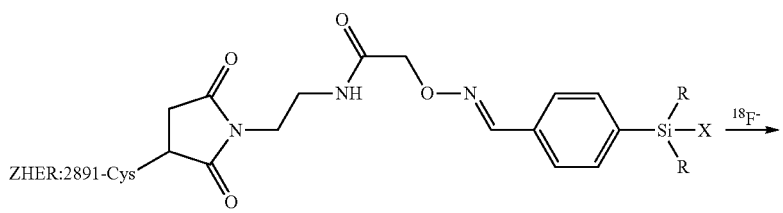

-continued

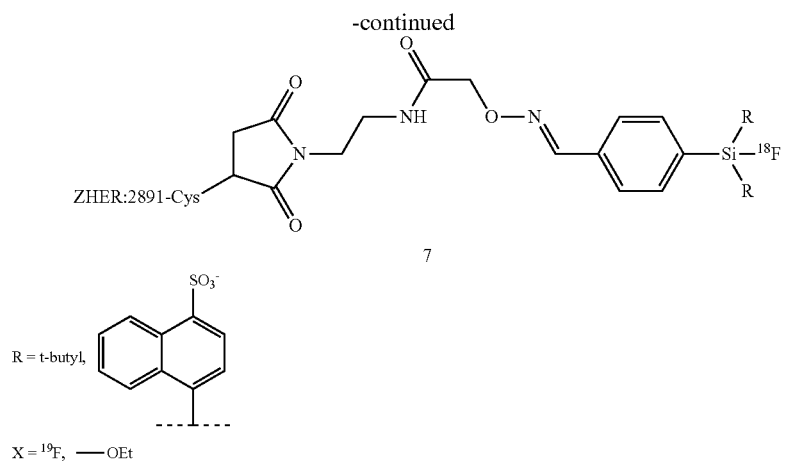

7

R = t-butyl,

X = $^{19}$F, ——OEt

In one or more embodiments, the methods of making a radiolabeled imaging agent or imaging agent composition of the invention as described herein, are automated. For example, a radiolabeled imaging agent or imaging agent composition of the invention may be conveniently prepared in an automated fashion by means of an automated radiosynthesis apparatus. There are several commercially-available examples of such platform apparatus, including TRACERlab™ (e.g., TRACERlab™ MX) and FASTlab™ (both from GE Healthcare Ltd.). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps. Optionally, in a further embodiment of the invention, the automated radiosynthesis apparatus can be linked to a high performance liquid chromatograph (HPLC).

The present invention therefore provides a cassette for the automated synthesis of a radiolabeled imaging agent or imaging agent composition of the invention, each as defined herein.

The invention also comprises methods of imaging at least a portion of a subject. In one embodiment, the method comprises administering a radiolabeled imaging agent or an imaging agent composition of the invention to a subject and imaging the subject. The subject may be imaged, for example, with a diagnostic device.

In one or more embodiments, a method of imaging may further comprise the steps of monitoring the delivery of the agent or composition to the subject and diagnosing the subject with a HER2-associated disease condition (e.g., breast cancer). In one embodiment, the subject may be a mammal, for example, a human. In another embodiment, the subject may comprise cells or tissues. The tissues may be used in biopsy. The diagnostic device may employ an imaging method chosen from magnetic resonance imaging, optical imaging, optical coherence tomography, X-ray, single photon emission computed tomography (SPECT), positron emission tomography (PET), or combinations thereof.

A radiolabeled imaging agent or an imaging agent composition of the invention may be administered to humans and other animals parenterally as a pharmaceutical composition. A pharmaceutical composition of the invention comprises a radiolabeled imaging agent or an imaging agent composition, as described herein, and a pharmaceutically acceptable carrier, excipient, solvent or diluent.

For example, a pharmaceutical composition of this invention for parenteral injection comprise pharmaceutically-acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by using coating materials such as lecithin, by adjusting the particle size in dispersions, and by using surfactants.

A pharmaceutical composition of the invention may also contain an adjuvant such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents, which delay absorption such as aluminum monostearate and gelatin.

A radiolabeled imaging agent or an imaging agent composition of the invention may be dispersed in physiologically acceptable carrier to minimize potential toxicity. Thus, the imaging agents may be dispersed in a biocompatible solution with a pH of about 6 to about 8. In some embodiments, the agent is dispersed in a biocompatible solution with a pH of about 7 to about 7.4. In other embodiments, the agent is dispersed in a biocompatible solution with a pH of about 7.4.

An imaging agent composition or a pharmaceutical composition of the invention may be combined with other additives that are commonly used in the pharmaceutical industry to suspend or dissolve the compounds in an aqueous medium, and then the suspension or solution may be sterilized by techniques known in the art. The imaging agent composition may be administered in a variety of forms and adapted to the chosen route of administration. For example, the agents may be administered topically (i.e., via tissue or mucus membranes), intravenously, intramuscularly, intradermally, or subcutaneously. Forms suitable for injection include sterile aqueous solutions or dispersions and sterile powders for the preparation of sterile injectable solutions, dispersions, liposomal, or emulsion formulations. Forms suitable for inhalation use include agents such as those dispersed in an aerosol. Forms suitable for topical administration include creams, lotions, ointments, and the like.

An imaging agent composition or a pharmaceutical composition of the invention may be concentrated to conveniently deliver a preferred amount of the agents to a subject and packaged in a container in the desired form. The agent may be dispensed in a container in which it is dispersed in a physiologically acceptable solution that conveniently facilitates administering the agent in concentrations between 0.1 mg and 50 mg of the agent per kg body weight of the subject.

In one or more embodiments, the target tissue may be imaged about four hours after administering the agents. In alternative embodiments, the target tissue may be imaged about 24 hours after administering the agents to the subject.

EXAMPLES

The following examples are provided for illustration only and should not be construed as limiting the invention.

Materials

A panel of tumorigenic cell lines with a reasonable probability of expressing HER2 was selected based on available literature (Bruskin, et. al. Nucl. Med. Biol. 2004:31:205; Tran, et. al. Imaging agent composition Chem. 2007:18:1956), as described in Table 3.

TABLE 3

| Cell line | Species | Type | Purpose |
|---|---|---|---|
| SKOV3 | Human | Ovarian carcinoma | Candidate |
| SKBR3 | Human | Breast carcinoma | Candidate |
| C6 | Rat | Glioma | control |

All cell lines were obtained from the American Type Culture Collection (ATCC) and cultured as recommended. Cells were cultured to >90% confluence prior to use. Flow cytometry (Beckman Coulter Cytomics FC500 MPL) was carried out on the cell lines listed in table 4 using anti-Her2 primary antibodies (R&D Systems, PN MAB 1129) and the Dako QIFIKIT (PN K0078) for quantitative analysis of indirect immunofluorescence staining. Calibration beads with 5 different populations bearing different numbers of Mab molecules were used in conjunction with the cell lines to determine number of surface receptors per cell. In all cases, appropriate isotype controls were obtained from the corresponding vendors.

Adherent cells were released from their flasks using cell dissociation buffer (PBS+10 mM EDTA) rather than trypsin to avoid proteolysis of cell surface receptors. Cells were washed twice in PBS and resuspended in ice-cold FC buffer (PBS+0.5% BSA w/v) to a concentration of $5$-$10 \times 10^6$ cells/ml. 100 µL aliquots of cells were mixed with 5 µg of primary antibody and incubated, on ice, for 45 minutes. Cells were then washed with 1 ml of ice cold flow cytometry (FC) buffer (PBS with 2% bovine serum albumin), centrifuged at 300×g for 5 min, and resuspended in 0.5 µL of FC buffer. 100 µL of 1:50 dilution with PBS of the secondary antibody fragment (F(ab)$_2$ FITC-conjugated goat anti-mouse Immunoglobulins) was added and incubated, on ice and in the dark, for 45 minutes. Cells were then washed twice with 1 mL of ice cold FC buffer, centrifuged at 300×g for 5 min, and resuspended in 500 µL of FC buffer. All stained cells were passed through a 100-micron filter prior to flow cytometry to prevent clogs of the flow cell.

Flow cytometry was carried out on a Beckman Coulter Cytomics FC500 MPL. A minimum of $5 \times 10^4$ events was collected for each tube. All analyses were single color, with detection of FITC in FL1. Forward scatter (FS) and side scatter (SS) data demonstrated that all cell populations were tightly grouped.

Figure 2A:
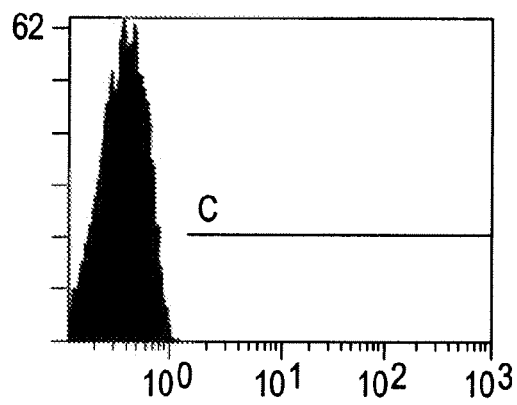
FIG. 2A and FIG. 2B are graphs of the qualitative flow cytometry of C6 (rat glioma, control) and human anti-HER2 antibody to SKOV3 (human ovarian carcinoma) respectively.
Figure 2B:
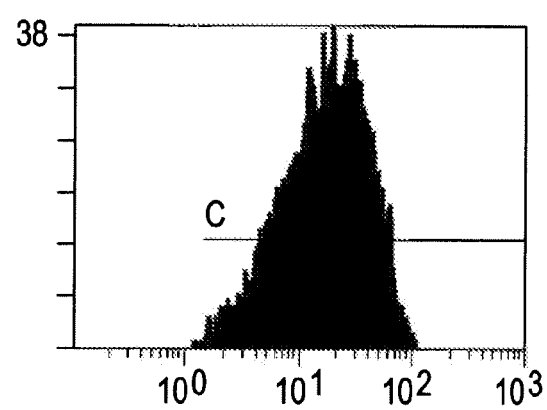
Figure 2C:
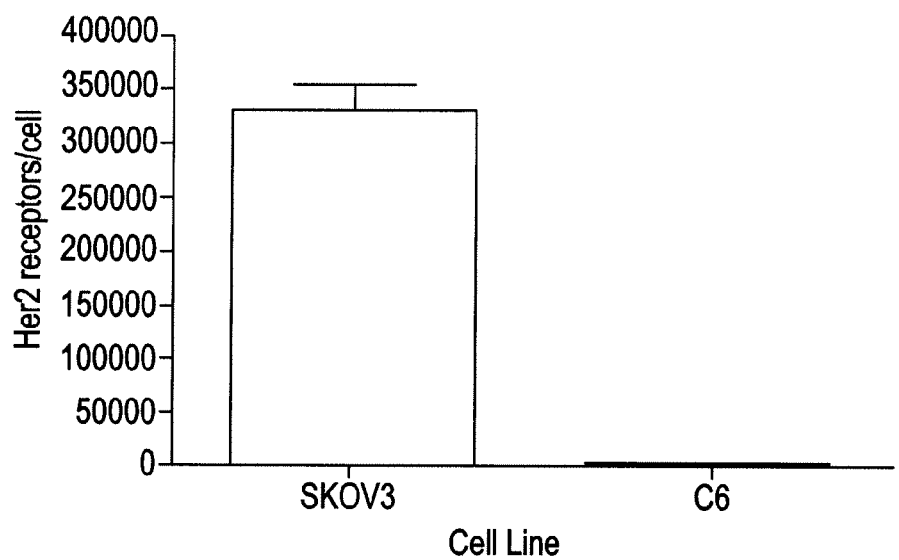
FIG. 2C shows a bar chart for Her2 receptors per cell for SKOV3 and C6 cell lines.
Figure 3:
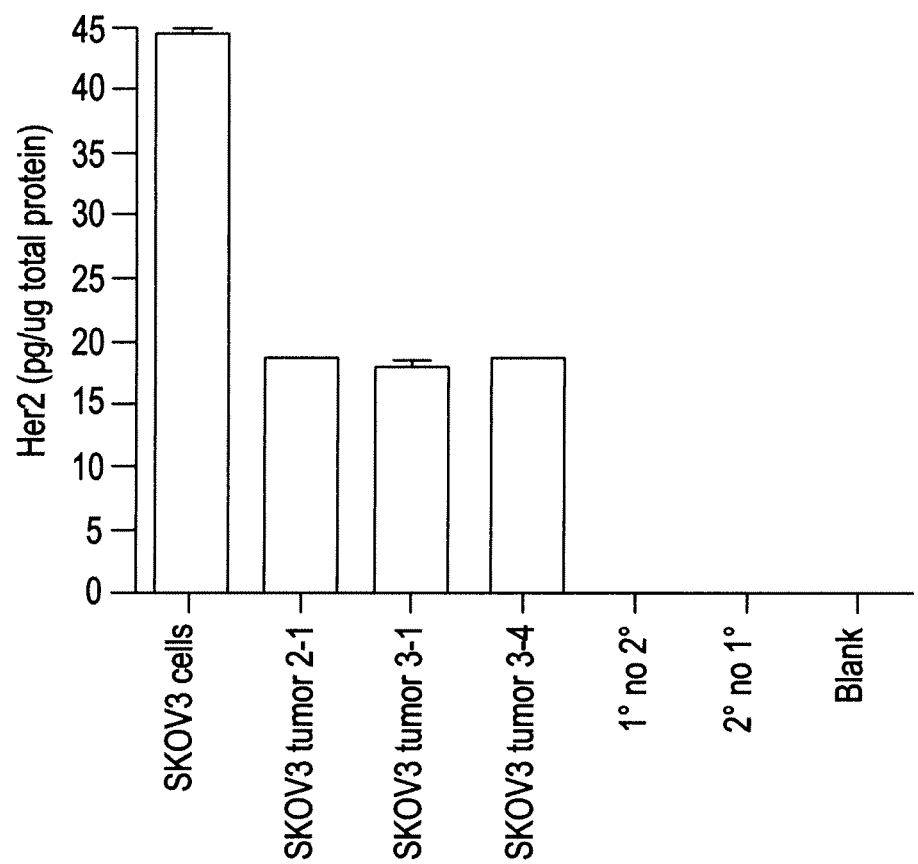
FIG. 3 is a bar graph of ELISA assays for Her2 with respect to a panel of tumor types SKOV3 2-1, SKOV3 3-1, SKOV3 3-4, with respect to SKOV3 cells, and blank.

Flow cytometry was used to evaluate the cells for their HER2 expression in vitro (FIGS. 2A, 2B, and 2C) with SKOV3 cells showing the highest level of HER2 expression (FIG. 3). The results in FIG. 3 were reproducible (n=3).

The highest expressing cell line was SKOV3. These cells were injected into 6-12 week old immuno-compromised mice and allowed to grow tumors. Tumor growth curves and success rates were dependent on the number of cells inoculated. Optimal tumor growth was obtained with three to four million cells/mouse In vivo studies were carried out with female CD-1 nude mice (Charles River Labs, Hopkinton, Mass.) with an age range between 6 and 15 weeks. Mice were housed in a ventilated rack with food and water ad libitum and a standard 12 hour day-night lighting cycle. For xenografts, animals were injected with 100 µl of cells in PBS. Cells were implanted subcutaneously in the right hindquarter Implantation was performed under isoflurane anesthesia. For SKOV3, between $3 \times 10^6$ to $4 \times 10^6$ cells were implanted in each mouse. Under these conditions, useable tumors (100 to 300 µg) were obtained in 3 to 4 weeks in greater than 80% of animals injected.

Tumors were collected from mice by dissection, and whole tumors were stored at 20° C. until processing. Tumors were ground on ice in 1 ml of RIPA buffer supplemented with a protease inhibitor cocktail (Santa Cruz Biotech, Santa Cruz, Calif. #24948) in a Dounce homogenizer. Homogenates were then incubated on ice for 30 minutes, then centrifuged at 10,000×G for 10 minutes in a refrigerated centrifuge. Supernatants were collected and stored on ice or at 4° C. until further processing. Protein concentrations in lysates were determined using a BCA protein assay kit (Pierce Biotechnology 23225). Lysates were diluted to a standard concentration to yield 20 µg of protein/well in the microtiter plate. ELISA's were run with a commercially available human HER2 kit (R&D Systems, DYC1129) according to the manufacturer's instructions. Each sample was run in triplicate, and data are reported as pg HER2/µg total protein, errors are reported as standard deviations.

Target expression in vivo was measured by ELISA. Excised tumors were homogenized and analyzed for HER2 using a commercially available matched pair kit (R&D systems, DYC1129, Minneapolis, Minn.). The results, in FIG. 3, show that the SKOV3 cell line grows a high-expressing tumor. ELISA controls were cell-culture lysates of the negative control lines used for flow cytometry. These results indicate that tumor xenografts of SKOV3 are appropriate for the in vivo study of molecules targeting human HER2.

All polypeptides were received from Affibody® AB in Sweden. The polypeptides are referred to by their numeric internal development codes, which are prefixed with "Z". Table 1 details the polypeptides described herein. The polypeptides include polypeptide Z00342 (SEQ. ID No. 1); polypeptide Z02891 (SEQ. ID No. 2); polypeptide Z00477 (SEQ. ID No. 3 and 4), and dimer of Z00477, i.e., (Z00477)$_2$ (SEQ. ID No. 5).

Binding interactions between the polypeptides and the HER2/neu antigen were measured in vitro using surface plasmon resonance (SPR) detection on a Biacore™ 3000 instrument (GE Healthcare, Piscataway, N.J.). The extracellular domain of the Her2/neu antigen was obtained as a conjugate with the Fc region of human IgG (Fc-Her2) from R&D Systems (Minneapolis, Minn.) and covalently attached to a CM-5 dextran-functionalized sensor chip (GE Healthcare, Piscataway, N.J.) pre-equilibrated with HBS-EP buffer (0.01M HEPES pH 7.4, 0.15M NaCl, 3 mM EDTA, 0.005% v/v surfactant P20) at 10 µL/min and subsequently activated with EDC and NHS. The Fc-HER2 (5 µg/ml) in 10 mM sodium acetate (pH 5.5) was injected onto the activated sensor chip until the desired immobilization level (~3000 Resonance Units) was achieved (2 mM) Residual activated groups on the sensor chip were blocked by injection of ethanolamine (1 M, pH 8.5). Any non-covalently bound conjugate was removed by repeated (5×) washing with 2.5 M NaCl, 50 mM NaOH. A second flow cell on the same sensor chip was treated identically, except with no Fc-HER2 immobilization, in order to serve as a control surface for refractive index changes and non-specific binding interactions with the sensor chip. Prior to the kinetic study, binding of the target analyte was tested on both surfaces and a surface stability experiment was performed to ensure adequate removal of the bound analyte and regeneration of the sensor chip following treatment with 2.5 M NaCl, 50 mM NaOH. SPR sensorgrams were analyzed using the BIAevaluation software (GE Healthcare, Piscataway, N.J.). The robustness of the kinetic model was determined by evaluation of the residuals and standard error for each of the calculated kinetic parameters, the "goodness of the fit" ($\chi^2$<10), and a direct comparison of the modeled sensorgrams to the experimental data. SPR measurements were collected at eight analyte concentrations (0-100 nM protein) and the resulting sensorgrams were fitted to a 1:1 Langmuir binding model.

Figure 1B:
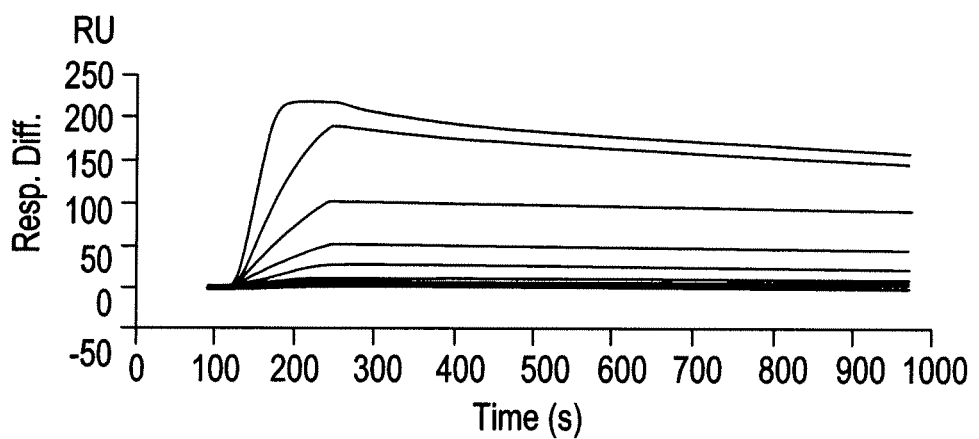

FIG. 1 shows example surface plasmon resonance (SPR) data obtained for Z00477 (SEQ. ID No. 3) and (Z00477)$_2$ (SEQ. ID No. 5) when run on human HER2-functionalized surfaces. This relationship holds true for all polypeptides for which the affinities are known (Table 2), in which the values for the dimer Z(477)2 (SEQ. ID No. 5) are estimates based on avidity affect.

Labeling of His6 (SEQ ID NO: 7)-tagged Polypeptides with the fac-[$^{99m}$Tc(CO)$_3$]$^+$ core was accomplished using modifications to a previously published procedure (Waibel, R.; et al., A. Nat. Biotechnol. 1999, 17, 897.). Briefly, Na[$^{99m}$TcO$_4$] in saline (4 mCi, 2 mL) was added to an Isolink® boranocarbonate kit (Alberto, R. et al, J. Am. Chem. Soc. 2001, 123, 3135.). The resulting solution was heated to 95° C. for 15-20 minutes, to give face-[$^{99m}$Tc(CO)$_3$(H$_2$O)$_3$]$^+$. A portion (2 mCi, 1 mL) of the solution was removed and neutralized to pH ~7 with 1 N HCl. A 325 µL aliquot was removed and added to a solution of the His6-Polypeptide (SEQ ID NO: 7) (40 µg). The resulting solution was heated in a water bath at 35-37° C. for 40 minutes. Typical radiochemical yields ranged from 80-95% (determined by ITLC-SG, Biodex, 0.9% NaCl). The crude reaction products were chromatographed on a NAP-5 column (GE Healthcare, 10 mM PBS) to give products of >99% radiochemical purity. Typical specific activities obtained were 3-4 µCi/ng. The resulting solution was then diluted with 10 mM PBS to give the proper concentration for subsequent biodistribution studies.

HPLC was carried out on an Agilent 1100 series HPLC equipped with a Grace-Vydac Peptide/Protein C4 (4.6×250 mm) column and a Raytest GABI radioactivity detector. Solvent A was 95:5 water:MeCN with 0.1% TFA, and solvent B was 5:95 water:MeCN with 0.1% TFA. The gradient was as follows (all changes linear; time/% B): 0/0, 4/20, 16/60, 20/100, 25/100, 26/0, 31/0.

Each polypeptide was labeled with the tricarbonyltechnetium core in high yield (>90%) before purification. Purification by NAP-5 chromatography gave samples of $^{99m}$Tc-labeled Polypeptides in >99% radiochemical purity (Table 4)

TABLE 4

| Compound | Crude yield (%) | Isolated yield (decay corr.) (%) | NAP-5 RCP (%) |
|---|---|---|---|
| Z00477 (SEQ. ID No. 3) | 56.9 | 24.7 (26.9) | 99.5 |

Figure 4:
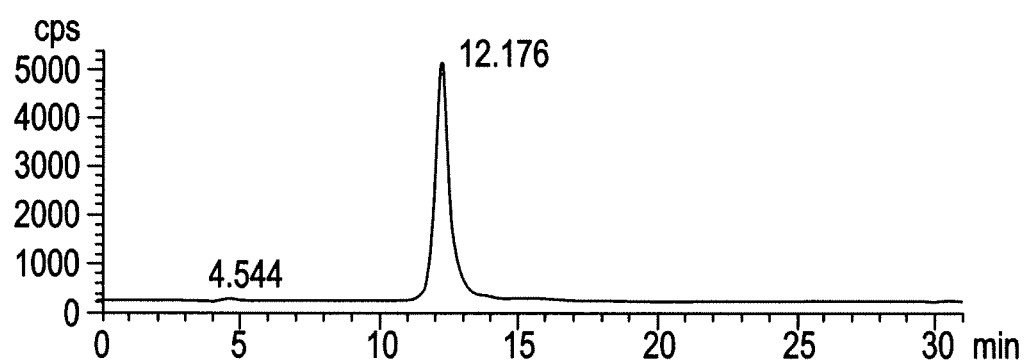
FIG. 4 is a reverse phase HPLC gamma chromatogram of $^{99m}$Tc labeled Z00477 (SEQ. ID No. 3).

Representative HPLC chromatograms of NAP-5 purified radiolabeled polypeptides are shown in FIG. 4. The retention time of the radiolabeled species was virtually unchanged from the corresponding unlabeled polypeptide's retention time in a 220 nm UV chromatogram (except for the time difference due to the physical separation of the UV and gamma detectors; data not shown).

Animal Models used to study $^{99m}$Tc(CO)$_3$(His$_6$)-Polypeptides ('His$_6$' disclosed as SEQ ID NO: 7)

In vivo studies were carried out with female CD-1 nude mice (Charles River Labs, Hopkinton, Mass.) with an age range between 6 and 15 weeks. Mice were housed in a ventilated rack with food and water ad libitum and a standard 12 hour day-night lighting cycle. For xenografts, animals were injected with 100 µl of cells in PBS. Cells were implanted subcutaneously in the right hindquarter Implantation was performed under isoflurane anesthesia. For SKOV3, between 3×10$^6$ to 4×10$^6$ cells were implanted in each mouse. Under these conditions, useable tumors (100 to 300 µg) were obtained in 3 to 4 weeks in greater than 80% of animals injected.

Biodistribution

Mice were given tail-vein injections of ~1 µg of $^{99m}$Tc-labeled polypeptides (~3 µCi/1 µg). Mice were placed in filter-paper lined cages until euthanasia. Three mice were euthanized at each timepoint and tissues of interest dissected and counted on a Perkin Elmer Wallac Wizard 1480 Gamma Counter. Data were collected for blood, kidney, liver, spleen, and injection site (tail). Urine from cages was pooled with the bladder and also counted. The remaining tissues were counted and the sum of all tissues plus urine for each animal was summed to provide the total injected dose. The % injected dose for each organ was determined based on this total, and organs were weighed for determination of the % injected dose per gram, (% ID/g). Data is reported as mean value for all three mice in the timepoint with error bars representing the standard deviation of the group.

Figure 6:
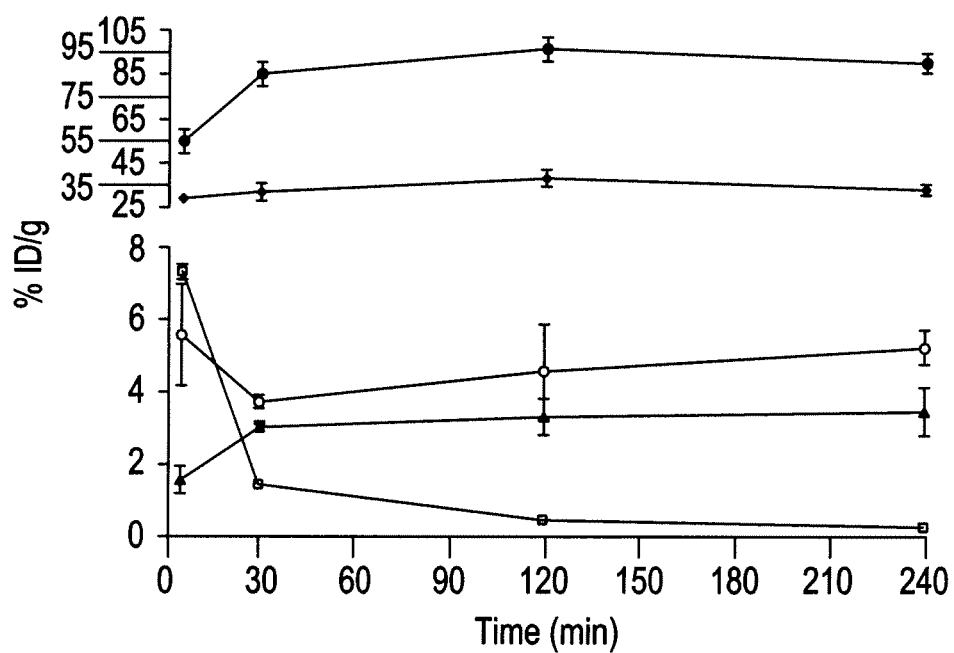
FIG. 6 is a graph of biodistribution profile of Z00477 (SEQ. ID No. 3) in blood, tumor, liver, kidney and spleen samples from SKOV3 tumor bearing mice, including the tumor:blood ratio over time.

The $^{99m}$Tc labeled Z00477 (SEQ. ID No. 4) polypeptide was injected into SKOV3 mice. FIG. 6 shows the tumor and blood curves for these experiments. The Z00477 (SEQ. ID No. 4) polypeptide shows good tumor uptake in target-expressing SKOV3 tumors, with a maximal value of approximately 3% of the injected dose per gram of tissue at 30 minutes post-injection (PI), and a peak tumor: blood ratio of more than 8 at 240 minutes PI.

Polypeptides exhibit a monoexponential clearance from the blood with half-lives of less than two minutes. This clearance is primarily mediated by the liver and kidneys. Polypeptide uptake in the spleen was moderate, and moderate to high uptake in the liver is observed, as described in Table 5.

TABLE 5

Z00477 (SEQ. ID No. 3) His6 (SEQ ID NO: 7)tagged uptake (% ID/g) in SKOV3 tumor bearing mice

|  | 5 Minutes | 30 Minutes | 120 Minutes | 240 Minutes |
|---|---|---|---|---|
| Blood | 7.30 ± 0.32 (n = 3) | 1.47 ± 0.16 (n = 3) | 0.56 ± 0.03 (n = 3) | 0.43 ± 0.03 (n = 3) |
| Tumor | 1.57 ± 0.62 (n = 3) | 3.06 ± 0.17 (n = 3) | 3.40 ± 0.87 (n = 3) | 3.60 ± 1.15 (n = 3) |
| Liver | 29.07 ± 0.70 (n = 3) | 32.19 ± 6.50 (n = 3) | 39.57 ± 6.29 (n = 3) | 35.17 ± 3.48 (n = 3) |
| Kidney | 54.83 ± 9.29 (n = 3) | 85.89 ± 10.00 (n = 3) | 97.99 ± 10.45 (n = 3) | 92.54 ± 7.36 (n = 3) |
| Spleen | 5.57 ± 2.39 (n = 3) | 3.76 ± 0.23 (n = 3) | 4.65 ± 2.21 (n = 3) | 5.36 ± 0.80 (n = 3) |

Bivalent polypeptides exhibit higher affinity than the corresponding monomers, presumably due to the avidity effect. Their larger size, however, may hinder tumor penetration. For the HER2 polypeptides, bivalent forms of each the four high affinity polypeptides were available. The Z00477 (SEQ. ID No. 3) dimer, (Z00477)$_2$ (SEQ. ID No. 5), was radiolabeled and used for a four-hour biodistribution experiment in SKOV3-tumored mice.

The monovalent and bivalent polypeptides otherwise exhibit similar biodistribution characteristics, and blood half-lives are observed for both in the one to two minute range. The results clearly indicate that both monomeric and divalent polypeptides can be targeted to HER2 in vivo.

Figure 7:
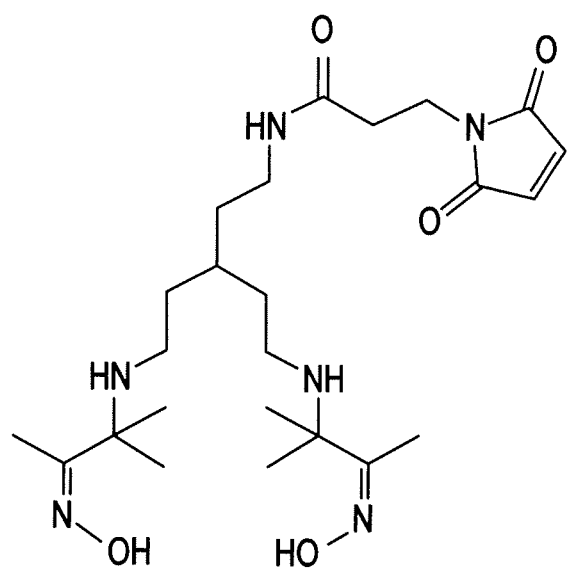
FIG. 7 is a diagram of the chemical structure for a Mal-cPN216 linker.

To introduce the $^{99m}$Tc chelator cPN216 (FIG. 7), a bifunctional compound Mal-cPN216 was synthesized comprising of a thiol-reactive maleimide group for conjugation to a terminal cysteine of a polypeptide and an amine oxime group for chelating $^{99m}$Tc.

cPN216-amine was obtained from GE Healthcare. N-β-maleimidopropionic acid was purchased from Pierce Technologies (Rockford, Ill.). N-methylmorpholine, (benzotriazol-1-yloxy) tripyrrolidinophosphonium hexafluorophosphate (PyBoP), dithiothreitol (DTT), ammonium bicarbonate, and anhydrous DMF were purchased from Aldrich (Milwaukee, Wis.). PBS buffer (1×, pH 7.4) was obtained from Invitrogen (Carlsbad, Calif.). HPLC-grade acetonitrile (CH$_3$CN), HPLC-grade trifluoroacetic acid (TFA), and Millipore 18 mΩ water were used for HPLC purifications.

Example 1

To an ice-cooled solution of N-β-maleimidopropionic acid (108 mg, 0.64 mmol), cPN216-amine (200 mg, 0.58 mmol), and PyBoP (333 mg, 0.64 mmol) in anhydrous DMF at 0° C. was added 0.4 M of N-methylmorpholine in DMF (128 μL, 1.16 mmol). The ice bath was removed after 2 hrs, and the mixture was stirred at room temperature overnight before being subjected to HPLC purification. The product Mal-cPN216 was obtained as a white powder (230 mg, 80% yield). 1H-NMR (400 MHz, DMSO-d6): δ 1.35 (m, 2 H), 1.43 (s, 12 H), 1.56 (m, 5 H), 1.85 (s, 6 H), 2.33 (dd, J1=8 Hz, J2=4 Hz, 2 H), 2.78 (m, 4 H), 3.04 (m, 2 H), 3.61 (dd, J1=8 Hz, J2=4 Hz, 2 H), 7.02 (s, 2 H), 8.02 (s, 1 H), 8.68 (s, 4 H), 11.26 (s, 2 H); m/z=495.2 for [M+H]$^+$ (C24H43N6O5, Calculated MW=495.3).

Figure 8A:
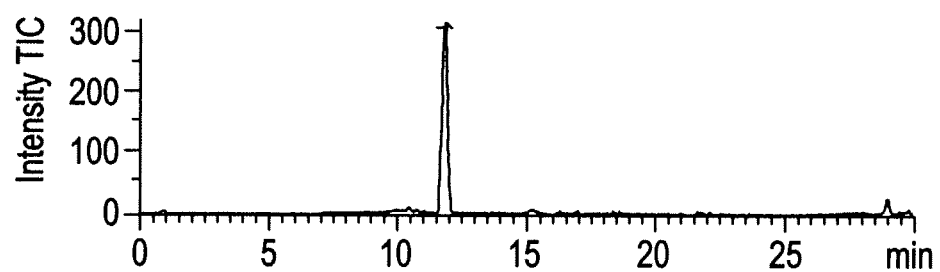
FIG. 8A is a graph of the electrospray ionization time of flight mass spectrum (ESI-TOF-MS) and FIG. 8B is a graph of mass deconvolution result for the purified Z00477 (SEQ. ID No. 3)-cPN216.
Figure 8B:
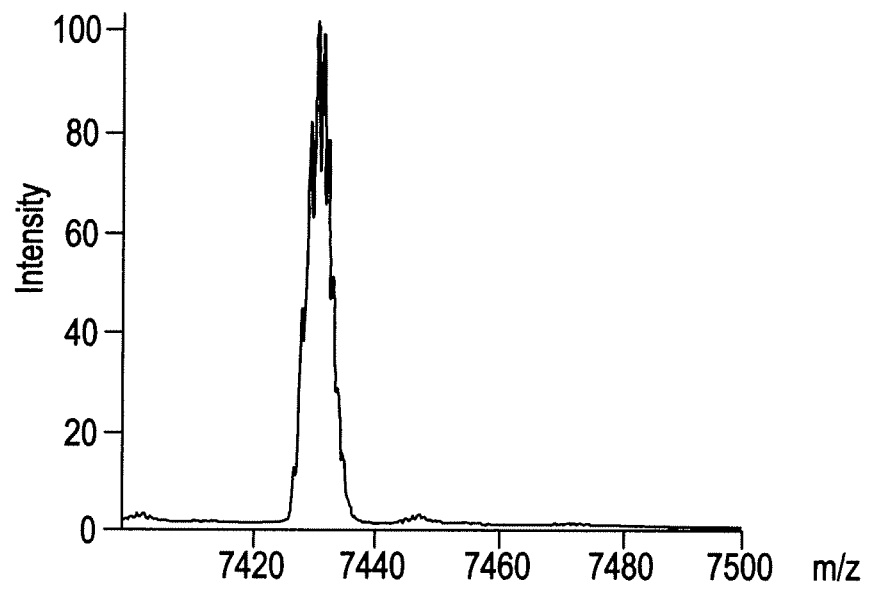

The polypeptide Z00477 (SEQ ID No. 3) was dissolved with freshly degassed PBS buffer (1×, pH 7.4) at a concentration of approximately 1 mg/mL. The disulfide linkage in the polypeptide was reduced by the addition of DTT solution in freshly degassed PBS buffer (1×, pH 7.4). The final concentration of DTT was 20 mM. The reaction mixture was vortexed for 2 hours and passed through a Zeba desalt spin column (Pierce Technologies) pre-equilibrated with degassed PBS buffer (1×, pH 7.4) to remove excess of DTT reagent. The eluted reduced polypeptide molecule was collected, and the bifunctional compound Mal-cPN216 was added (20 equivalents per equivalent of the polypeptide) as a solution in DMSO, and the mixture was vortexed at room temperature for 3 hours and frozen with liquid-nitrogen. The reaction mixture was stored overnight before being subject to Reverse phase HPLC purification (FIGS. 8A and 8B).

The HPLC purification was performed on a MiCHROM Magic C18AQ 5μ 200 A column (MiChrom Bioresources, Auburn, Calif.). Solvent A: H$_2$O (with 0.1% formic acid), Solvent B: CH$_3$CN (with 0.1% formic acid). Gradient: 5-100% B over 30 mins.

The fractions containing desired product were combined and neutralized with 100 mM ammonium bicarbonate solution, and the solvents were removed by lyophilization to give the desired imaging agent composition as a white solid (yield 41%).

LC-MS analysis of the purified product confirmed the presence of the desired product, and the MW suggested that only one cPN216 label was added to polypeptide constructs (Z00477 (SEQ. ID No. 3)-cPN216: calculated MW: 7429 Da. found: 7429 Da; Z02891 (SEQ. ID No. 2)-cPN216 calculated MW: 7524 Da. found: 7524 Da).

Example 2

To a 20 mL vial was added 10.00 mL of distilled, deionized water. Nitrogen gas was bubbled through this solution for approximately 30 minutes prior to addition of the NaHCO$_3$ (450 mg, 5.36×10$^{-3}$ mol), Na$_2$CO$_3$ (60 mg, 5.66×10$^{-4}$ mol) and sodium para-aminobenzoate (20 mg, 1.26×10$^{-4}$ mol). All reagents were weighed independently and added to the vial containing water. Tin chloride (1.6 mg, 7.09×10$^{-6}$ mol) and MDP (2.5 mg, 1.42×10$^{-5}$ mol) were weighed together into a 1 dram vial and subsequently transferred (with 1 subsequent wash) by rapid suspension in approximately 1 mL of the carbonate buffer mixture. 10 μL aliquots were removed and transferred under a stream of nitrogen to silanized vials, immediately frozen and maintained in a liquid nitrogen bath until lyophilization. Each vial was partially capped with rubber septa and placed in a tray lyophilizer overnight. Vials were sealed under vacuum, removed from the lyophilizer, crimp-sealed with aluminum caps, re-pressurized with anhydrous nitrogen and stored in a freezer until future use.

Example 3

Synthesis of the radiolabeled polypeptide was performed using a one-step kit formulation produced in house (Chelakit A+) containing a lyophilized mixture of stannous chloride as a reducing agent for technetium, methylene diphosphonic acid, p-aminobenzoate as a free-radical scavenger and sodium bicarbonate/sodium carbonate (pH 9.2) as buffer. In rapid succession, 20 µL of a 2 µg/µL solution of polypeptide in saline was added to the Chelakit, followed immediately by Na$^{99m}$TcO$_4$ (0.8 mCi, 29.6 MBq) in 0.080 mL of saline (0.15M NaCl) obtained from Cardinal Health (Albany, N.Y.). The mixture was agitated once and allowed to sit at ambient temperature for 20 min. Upon completion, the crude radiochemical yield was determined by ITLC (Table 6 below according to ITLC-SG, Biodex, 0.9% NaCl).

TABLE 6

| Compound | Crude RCP (%) | purified RCP (%) | RCY (%) decay corrected/ (uncorrected) |
|---|---|---|---|
| Z00477 (SEQ. ID No. 3) | 49.2 | 98.6 | 53.9 (13.1) |
| Z02891 (SEQ. ID No. 2) | 71.6 | 97.5 | 46.9 (43.8) |

Figure 9:
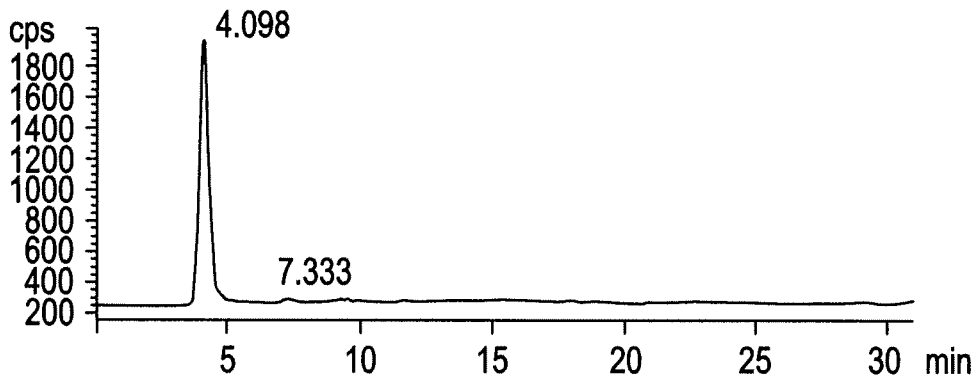
FIG. 9 is a reverse phase HPLC gamma trace chromatogram for Z02891-cPN216 (SEQ. ID No. 2) labeled with $^{99m}$Tc.

The reaction volume was increased to 0.45 mL with 0.35 mL of 150 mM sterile NaCl, and the final product purified by size exclusion chromatography (NAP5, GE Healthcare, charged with 10 mM PBS). The crude reaction mixture was loaded onto the NAP5 column, allowed to enter the gel bed and the final purified product isolated after elution with 0.8 mL of 10 mL PBS. Final activity was assayed in a standard dose calibrator (CRC-15R, Capintec, Ramsey, N.J.). Radiochemical yield (Table 6) and purity were determined by ITLC (>98.5%), C4 RP-HPLC (FIG. 9) and SEC-HPLC analysis. The final product (10-15 µCi/µg, 0.2-0.5 µCi/µL (0.37 MBq/µg, 7.4 MBq/mL)) was used immediately for biodistribution studies.

The HPLC conditions used for this experiment were as follows: C4 RP-HPLC method 1: Solvent A: 95/5 H$_2$O/CH$_3$CN (with 0.05% TFA), Solvent B: 95/5 CH$_3$CN/ddH$_2$O (distilled, deionized water) with 0.05% TFA. Gradient elution: 0 min 0% B, 4 min 20% B, 16 min 60% B, 20 min. 100% B, 25 min. 100% B, 26 min 0% B, 31 min 0% B.

C4 RP-HPLC method 2: Solvent A: 0.06% NH$_3$ in water, Solvent B: CH$_3$CN. Gradient elution: 0 min 0% B, 4 min 20% B, 16 min 60% B, 20 min 100% B, 25 min 100% B, 26 min 0% B, 31 min 0% B.

RP-HPLC analysis performed on an HP Agilent 1100 with a G1311A QuatPump, G1313A autoinjector with 100 µL syringe and 2.0 mL seat capillary, Grace Vydac—protein C4 column (S/N E050929-2-1, 4.6 mm×150 mm), G1316A column heater, G1315A DAD and Ramon Star—GABI gamma-detector.

SEC HPLC: Solvent: 1× (10 mM) PBS (Gibco, Invitrogen, pH 7.4 containing CaCl$_2$ and MgCl$_2$). Isocratic elution for 30 min. Analysis performed on a: Perkin Elmer SEC-4 Solvent Environmental control, Series 410 LC pump, ISS 200 Advanced LC sample processor and Series 200 Diode Array Detector. A Raytest GABI with Socket 8103 0111 pinhole (0.7 mm inner diameter with 250 µL volume) flow cell gamma detector was interfaced through a Perkin Elmer NCI 900 Network Chromatography Interface. The column used was a Superdex 75 10/300 GL High Performance SEC column (GE Healthcare. code: 17-5174-01, ID no. 0639059).

Figure 5A:
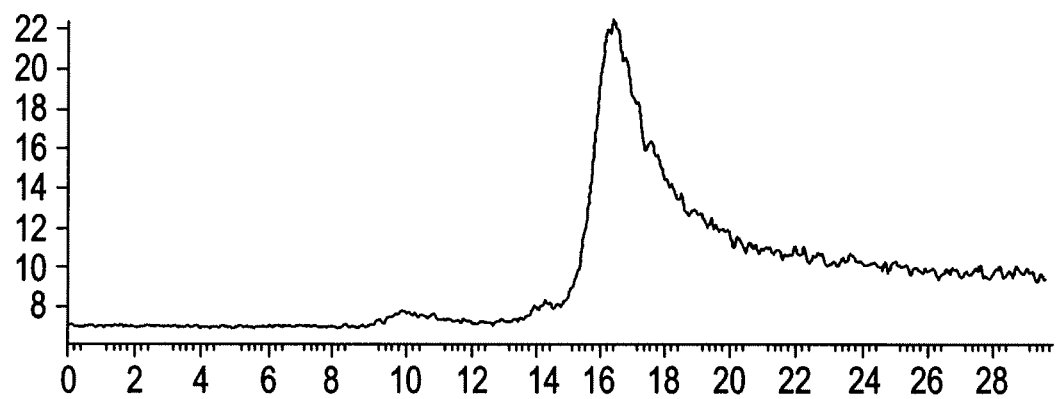
FIG. 5A is a size exclusion HPLC gamma chromatogram of aggregated $^{99m}$Tc(CO)$_3$(His6)Z00477 (SEQ. ID. No. 4) ('His6' disclosed as SEQ ID NO: 7) at pH 9.
Figure 5B:
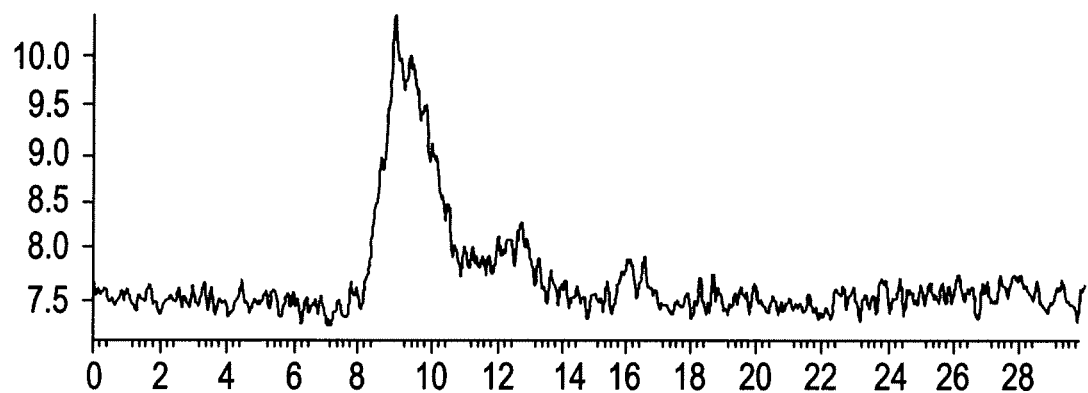
FIG. 5B a size exclusion HPLC gamma chromatogram of non aggregated $^{99m}$Tc(CO)$_3$(His6)Z00477 ('His6' disclosed as SEQ ID NO: 7) labeled Affibody® standard.

The operating pH of the Chelakits used to incorporate $^{99m}$Tc into the cPN216 chelate (pH=9.2) nearly matched the calculated pI of the Z00477 (SEQ. ID No. 3) polypeptide. Labeling under these conditions were determined to cause aggregation in the final product (FIGS. 5A and 5B). Aggregation was confirmed by size exclusion HPLC and through the increased blood residence time and liver uptake observed in the biodistribution studies. By altering the isoelectric point of the polypeptide, $^{99m}$Tc was successfully incorporated onto the Z02891 (SEQ. ID No. 2) construct. Size exclusion HPLC confirmed the presence of a species with the appropriate molecular weight and biodistribution studies showed uptake of the tracer into the tumor xenografts.

In vivo studies were carried out with female CD-1 nude mice (Charles River Labs, Hopkinton, Mass.) with an age range between 6 and 15 weeks. Mice were housed in a ventilated rack with food and water ad libitum and a standard 12 hours day-night lighting cycle. For xenografts, animals were injected with 100 µl of cells in PBS. Cells were implanted subcutaneously in the right hindquarter Implantation was performed under isoflurane anesthesia. For SKOV3, between 3×10$^6$ to 4×10$^6$ cells were implanted in each mouse. Under these conditions, useable tumors (100 to 300 µg) were obtained in 3 to 4 weeks in greater than 80% of animals injected.

Mice were given tail-vein injections of ~1 ug of $^{99m}$Tc-labeled polypeptides (~10 µCi/1 µg). Mice were placed in filter-paper lined cages until euthanasia. Three mice were euthanized at each timepoint and tissues of interest dissected and counted on a Perkin Elmer Wallac Wizard 1480 Gamma Counter. Data were collected for blood, kidney, liver, spleen, and injection site (tail). Urine from cages was pooled with the bladder and also counted. The remaining tissues were counted and the sum of all tissues plus urine for each animal was summed to provide the total injected dose. The % injected dose for each organ was determined based on this total, and organs were weighed for determination of the % injected dose per gram, (% ID/g). Data is reported as mean value for all four to five mice in the time point with error bars representing the standard deviation of the group. Four time points were taken over four hours (5, 30, 120, and 240 minutes post-injection).

Figure 10:
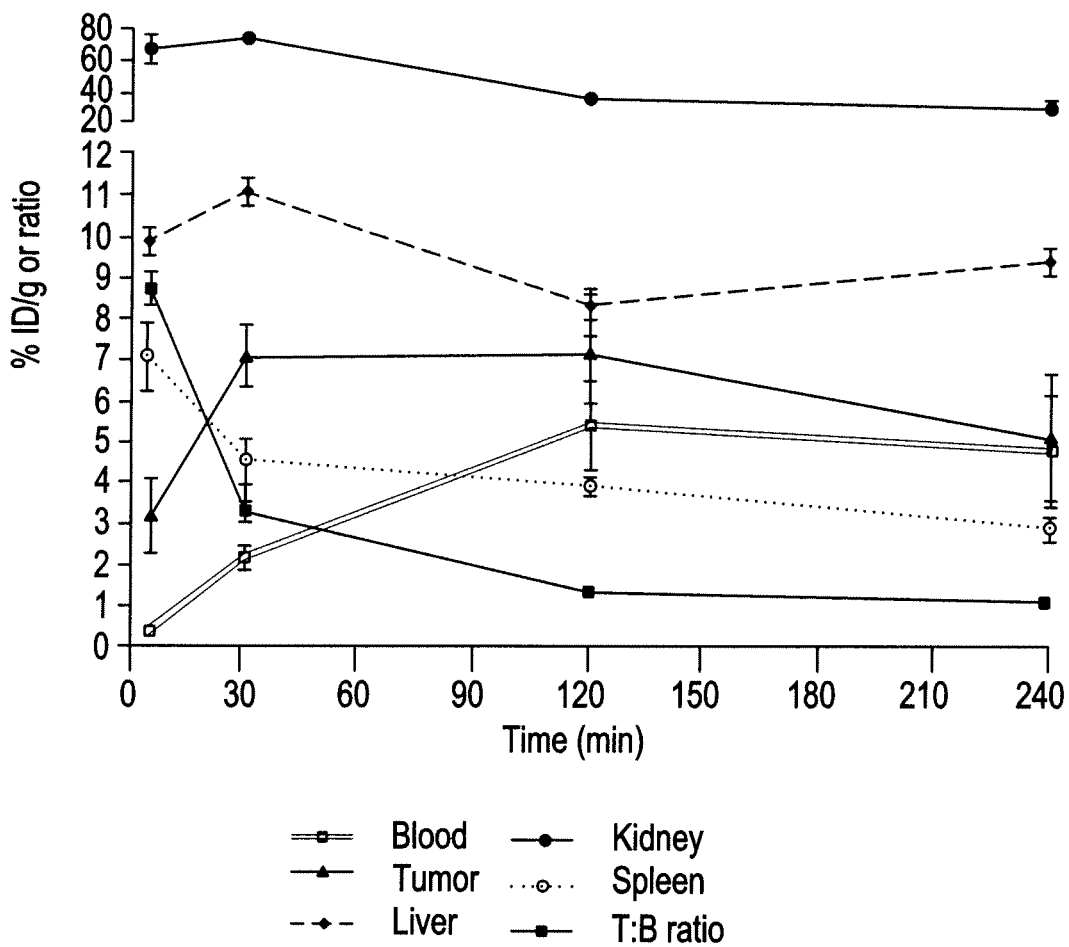
FIG. 10 is a graph of the biodistribution profile of Z02891 (SEQ. ID No. 2) labeled with $^{99m}$Tc via cPN216 (% ID, % injected dose)) in blood, liver, kidneys, spleen, and tail samples from SKOV3 tumor bearing mice.
Figure 11:
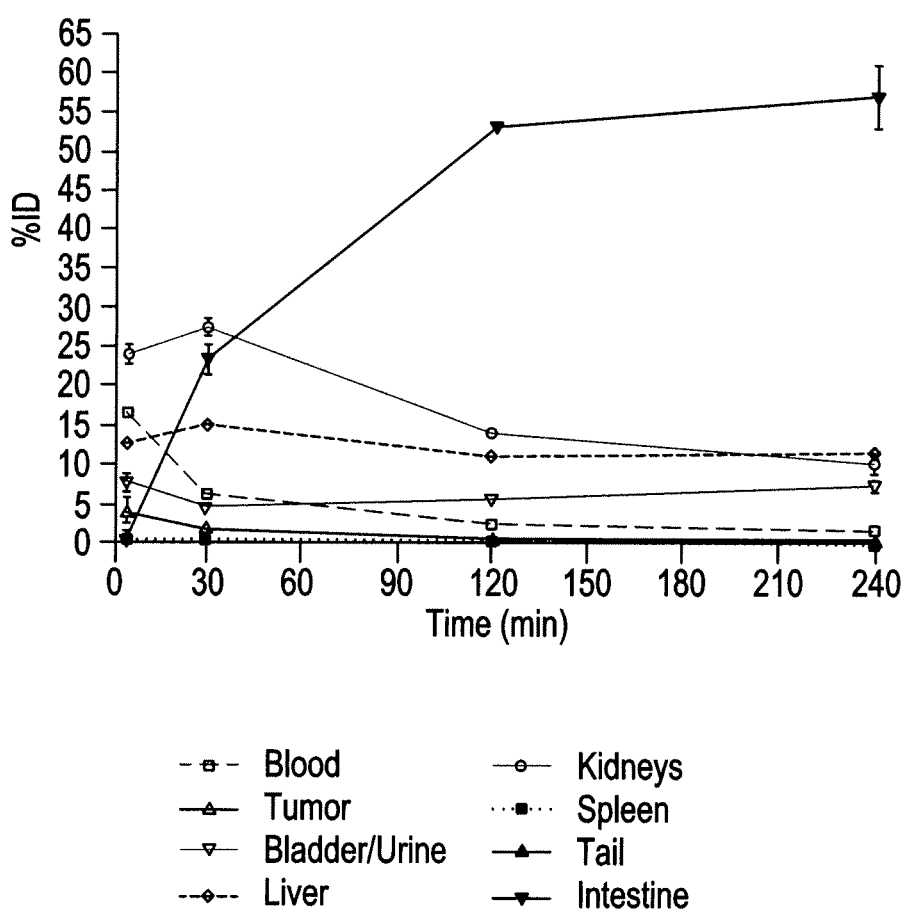
FIG. 11 is a graph of the biodistribution profile of Z02891 (SEQ. ID No. 2) labeled with $^{99m}$Tc via cPN216 (% ID, % injected dose) in tumor, blood, liver, kidneys, bladder/urine, tail, intestine and spleen samples from SKOV3 tumor bearing mice.
Figure 12:
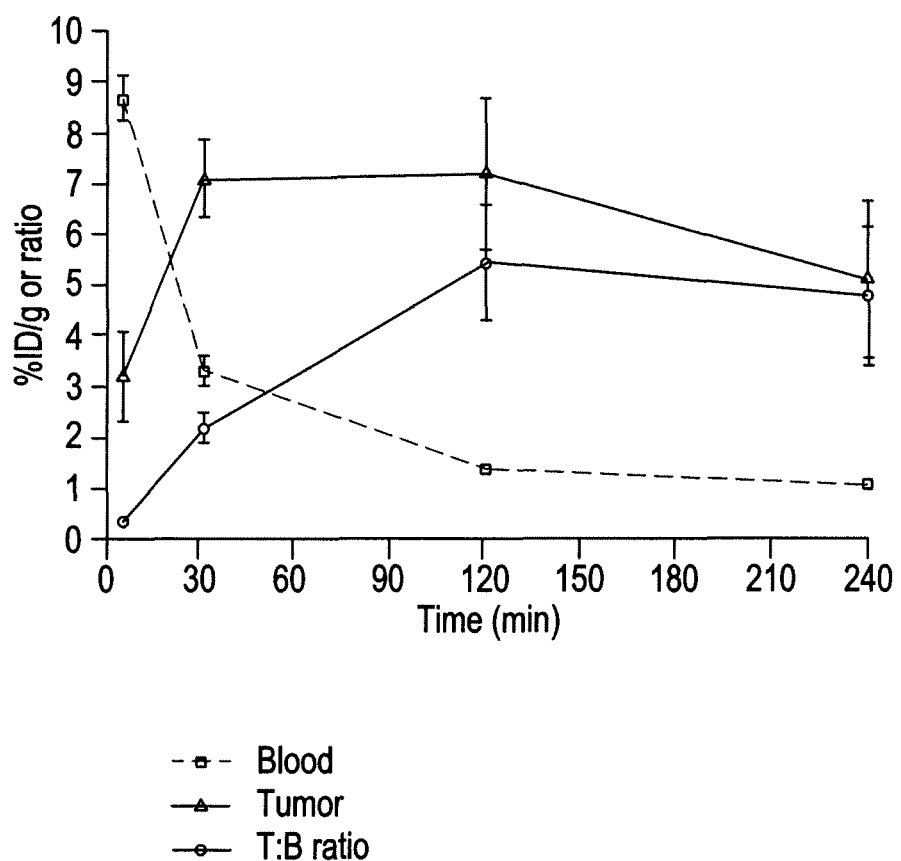
FIG. 12 is a graph of the biodistribution profile for Z02891 (SEQ. ID No. 2) in SKOV3 tumor bearing mice showing the tumor: blood ratio.

The Z02891 (SEQ. ID No. 2)-cPN216-$^{99m}$Tc polypeptide shows strong tumor uptake in target-expressing SKOV3 tumors, with a value of 7.11±1.69% (n=5) of the injected dose per gram of tissue at 30 minutes post-injection (PI), which remains fairly constant over the time-course of the study up to 240 min PI. Tumor: blood ratios were 2, 5, and 5 at 30, 120, and 240 min post injection, respectively. FIGS. 10, 11 and 12 show the tumor, blood and tumor: blood curves for these experiments.

The Polypeptides exhibit a monoexponential clearance from the blood with half-lives of less than two minutes. This clearance is primarily mediated by the kidneys, with 10.58±2.96 (n=5) ID/organ at 240 min post-injection PI. Activity is secreted primarily in the urine. Polypeptide uptake in the spleen was moderate to high due to possible aggregation, and moderate uptake in the liver is observed, e.g., 12% ID/organ (equivalent in value in mice to % ID/g) over the course of the study.

Biodistribution Results for Z02891 (SEQ. ID No. 2)-cPN216-$^{99m}$Tc

TABLE 7

Z02891 (SEQ. ID No. 2) cPN216 uptake (% ID/g) in SKOV3 tumor bearing mice

|  | 5 Minutes | 30 Minutes | 120 Minutes | 240 Minutes |
|---|---|---|---|---|
| Blood | 8.69 ± 0.99 (n = 5) | 3.32 ± 0.48 (n = 5) | 1.33 ± 0.05 (n = 5) | 1.05 ± 0.09 (n = 5) |
| Tumor | 3.19 ± 1.78 (n = 4) | 7.11 ± 1.69 (n = 5) | 7.18 ± 3.33 (n = 5) | 5.07 ± 3.47 (n = 5) |
| Liver | 9.87 ± 0.81 (n = 5) | 11.07 ± 1.06 (n = 5) | 8.33 ± 0.50 (n = 5) | 9.38 ± 0.69 (n = 5) |
| Kidney | 67.61 ± 9.24 (n = 5) | 74.15 ± 4.17 (n = 5) | 37.14 ± 3.48 (n = 5) | 29.67 ± 10.87 (n = 5) |
| Spleen | 7.07 ± 1.84 (n = 5) | 4.51 ± 1.25 (n = 5) | 3.91 ± 0.44 (n = 5) | 2.85 ± 0.62 (n = 5) |

Example 4

Z00477 (SEQ. ID. NO. 4), Z00342 (SEQ. ID No. 1) and Z02891 (SEQ. ID No. 2)-cysteine polypeptides were functionalized with an aminoxy group via an engineered C-terminal cysteine. The purity of the polypeptide molecules provided was determined to be >95% by High Performance Liquid Chromatography (HPLC).

Example 5

Figure 13A:
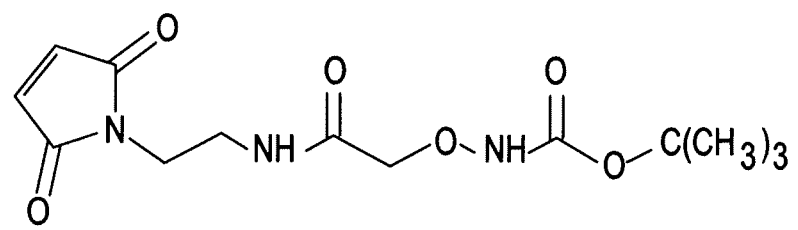
FIGS. 13A and 13B are diagrams of the chemical structures for Boc-protected malimide-aminoxy (Mal-AO-Boc) and malimide-aminoxy (Mal-AO) linkers. 13A is the chemical structure for tert-butyl 2-(2-(2,5-dioxo-2,5-dihydro-1H-pyrrol-1-yl)ethylamino)-2-oxoethoxycarbamate (Mal-AO-Boc) and 13B is the chemical structure for 2-(aminooxy)-N-(2-(2,5-dioxo-2,5-dihydro-1H-pyrrol-1-yl)ethyl)acetamide hydrochloride (Mal-AO.HCl).
Figure 13B:
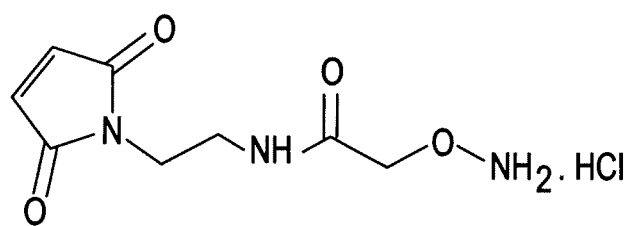

To incorporate $^{18}$F into the Polypeptide molecules, a bifunctional linker Mal-aminooxy was synthesized comprising of two orthogonal groups: a thiol-reactive maleimide group for conjugation to the engineered cysteine and an aldehyde-reactive aminoxy group (FIGS. 13A and 13B). This linker was prepared by reacting N-(2-aminoethyl) malemide with 2-(tert-butoxycarbonylaminooxy) acetic acid using 1-ethyl-3-[3-dimethylaminopropyl]carbodiimide (EDC)-mediated coupling conditions yielding the Boc-protected form of the linker. The Boc protecting group was then de-protected by acid cleavage to give the final Mal-AO product in quantitative yield. The final product was used directly without further purification.

General

Dichloromethane, 2-(tert-butoxycarbonylaminooxy) acetic acid, triethylamine, N-(2-aminoethyl)maleimide trifluoroacetic acid (TFA) salt, N-hydroxybenzotriazole hydrate (HOBT), 1-ethyl-3-[3-dimethylaminopropyl]carbodiimide (EDC), dithiothriotol (DTT), and all other standard synthesis reagents were purchased from Sigma-Aldrich Chemical Co. (St. Louis, Mo.). All chemicals were used without further purification. PBS buffer (1×, pH 7.4) was obtained from Invitrogen (Carlsbad, Calif.). HPLC-grade ethyl acetate, hexanes, acetonitrile ($CH_3CN$), trifluoroacetic acid (TFA), and Millipore 18 mΩ water were used for purifications.

Example 6

To a solution of 2-(tert-butoxycarbonylaminooxy)acetic acid (382 mg, 2 mmol) in anhydrous dichloromethane (20 mL) was added sequentially triethylamine (307 μL, 2.2 mmol), N-(2-aminoethyl)maleimide-TFA salt (508 mg, 2 mmol), HOBT(306 mg, 2 mmol), and EDC (420 mg, 2.2 mmol). After being stirred for 24 hrs at room temperature, the reaction mixture was diluted with ethyl acetate (50 mL) and washed with saturated sodium bicarbonate solution (3×30 mL), water (30 mL), and brine (30 mL). The organic layer was dried over anhydrous magnesium sulfate and filtered. The filtrate was concentrated to a pale yellow solid, which was purified by column chromatography (70% ethyl acetate in hexanes) to give the product as a white powder (500 mg, 80% yield). $^1$H-NMR (400 MHz, $CDCl_3$): δ 1.50 (s, 9 H), 3.55 (tt, J1=6.0 Hz, J2=6.5 Hz, 2 H), 3.77 (dd, J=7.6 Hz, 2 H), 4.30 (s, 2 H), 6.3 (s, 2 H).

Example 7

A solution of 9.3 mg of Mal-AO-Boc in 1 mL of 3M HCl in methanol was stirred at room temperature for 18 hours. Solvents were removed under vacuum to yield Mal-AO as a light yellow solid. (80% yield). $^1$H-NMR (400 MHz, DMSO-$d_6$): δ 3.27 $CH_2$ (t, J=4.0 Hz, 2H), 3.49 $CH_2$ (t, J=4.0 Hz, 2H), 4.39 $CH_2O$ (s, 2H), 7.00 CH=CH (s, 2H); m/z=214.07 for $[M+H]^+$ ($C_8H_{12}N_3O_4$, Calculated MW=214.11))

Example 8

The polypeptide (Z00477 (SEQ ID No. 4), Z00342 (SEQ ID No. 1) or Z02891 (SEQ ID. No. 2)) was dissolved with freshly degassed PBS buffer (1×, pH 7.4) at a concentration of approximately 1 mg/mL. The disulfide linkage in the polypeptide was reduced by the addition of dithiothreitol (DTT) solution in freshly degassed PBS buffer (1×, pH 7.4). The final concentration of DTT is 20 mM. The reaction mixture was vortexed for 2 hours and eluted through a Zeba desalt spin column (Pierce Technologies) pre-equilibrated with degassed PBS buffer to remove excess of DTT reagent. The reduced polypeptide was collected, and the bifunctional Mal-AO compound was added (15 equivalents per equivalent of the polypeptide) as a solution in DMSO. After being vortexed at room temperature overnight, the reaction mixture was purified with High Performance Liquid Chromatography (HPLC) (FIGS. 14A and 14B).

The HPLC purification was performed on a MiCHROM Magic C18AQ 5μ 200 A column (MiChrom Bioresources, Auburn, Calif.). Solvent A: $H_2O$ (with 0.1% formic acid), Solvent B: $CH_3CN$ (with 0.1% formic acid). Gradient: 5-100% B over 30 mins. The fractions containing desired product was combined and neutralized with 100 mM ammonium bicarbonate solution, and the solvents were removed by lyophilization to give the aminoxy-modified polypeptide as a white solid.

ESI-TOF-MS analysis confirmed the presence of target product with the expected molecular weights (calculated MW: 6964 Da, 8531 Da, and 7243 Da. found: 6963 Da, 8532 Da, and 7244 Da for Z00477 (SEQ. ID No. 4)—$ONH_2$, Z00342 (SEQ. ID No. 1)-$ONH_2$, and Z02891 (SEQ. ID No. 2)-$ONH_2$, respectively.

Example 9

Preparation of 18FBA

Methods: All reactions were performed either under a nitrogen atmosphere or in a crimp-top sealed vial purged with nitrogen prior to use. Kryptofix 222 (Aldrich) and K$_2$CO$_3$ (EMD Science) were purchased and used as received. Optima™-grade acetonitrile was used as both HPLC and reaction solvents.

K$^{18}$F (40 mCi·mL$^{-1}$ (1480 MBq·mL$^{-1}$) in purified water) was obtained from IBA Molecular (Albany, N.Y.) and PET-NET Solutions (Albany, N.Y.) and were used as received. The [$^{18}$F$^-$] fluoride was first immobilized on a Chromafix 30-PS-HCO3 anion exchange cartridge (ABX, Radeberg, Germany), then eluted into a drydown vessel with a 1 mL, 4:1 mixture of acetonitrile: distilled, deionized H$_2$O (ddH$_2$O) containing Kryptofix K222 (376 g·mol$^{-1}$, 8 mg, 2.13×10$^{-5}$ mol) and potassium carbonate (138.2 g·mol$^{-1}$, 2.1 mg, 1.52× 10$^{-5}$ mol). The solvent was removed under partial vacuum and a flow of nitrogen with gentle heating (~45° C.) (~15 min) The source vial and anion exchange cartridge were then washed with 0.5 mL of acetonitrile containing K222 (8 mg) and the reaction mixture again brought to dryness under partial vacuum and gentle heating (~10 min) The reaction vessel was repressurized with nitrogen and the azeotropic drydown repeated once with an additional 0.5 mL of acetonitrile. 4-formyl-N,N,N-trimethylanilinium triflate (313.30 g·mol$^{-1}$, 3.1 mg, 9.89×10$^{-6}$ mol) was dissolved in 0.35 mL of anhydrous DMSO (Acros) and added directly to the reaction vessel containing the K$^{18}$F·K222, K$_2$CO$_3$. The reaction mixture was heated to 90° C. for 15 min and immediately cooled and quenched with 3 mL of ddH$_2$O. This mixture was subsequently passed through a cation exchange cartridge (Waters SepPak Light Accell Plus CM), diluted to 10 mL with ddH$_2$O, and loaded onto a reverse phase C18 SepPak (Waters SepPak Plus C18). The SepPak was flushed with 10 mL of ddH$_2$O then purged with 30 mL of air. [$^{18}$F]4-fluorobenzaldehyde ($^{18}$FBA), was eluted in 1.0 mL of methanol.

Example 10

Figure 15:
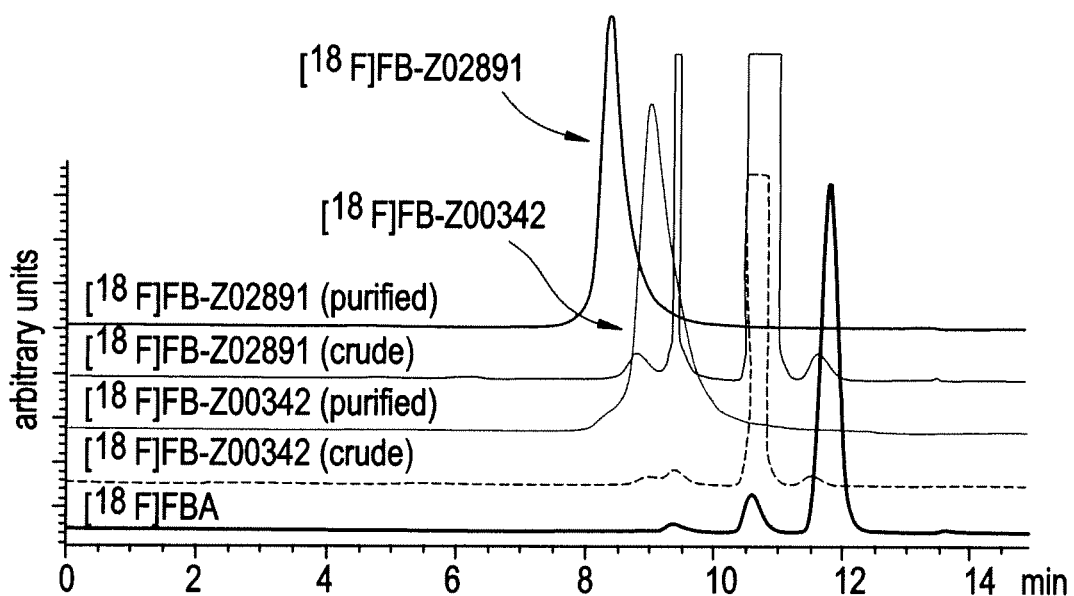
FIG. 15 is the reverse phase HPLC gamma chromatogram for the crude reaction mixtures and purified final products of $^{18}$F-fluorobenzyl-Z00342 (SEQ. ID No. 1) and $^{18}$F-fluorobenzyl-Z02891' (SEQ. ID No. 2).

Separately, a high recovery vial (2 mL, National Scientific) was charged with either the Z00477-(SEQ. ID No. 3)-ONH$_2$ (0.35-0.5 mg), Z00342-(SEQ. ID No.1)-ONH$_2$ (0.35-0.5 mg) or Z02891-(SEQ. ID No. 2)-ONH$_2$ (0.35-0.5 mg). The solid was suspended in 25 µL of ddH$_2$O and 8 µL of trifluoroacetic acid. 25 µL of $^{18}$FBA in methanol (see Example 9) was transferred to the reaction vial. The vessel was capped, crimped, placed in a heating block and maintained at 60° C. for 15 minutes; at which point a small aliquot (<5 µL) was removed for analytical HPLC analysis. 450 µL of ddH$_2$O with 0.1% TFA was used to dilute the solution to approx. 500 µL in preparation for semi-preparative HPLC purification. $^{18}$FB-Polypeptide was isolated and purified by semi-preparative HPLC. The HPLC fraction containing the product (0.113 mCi/4.18 MBq) was diluted 5:1 with ddH$_2$O and subsequently immobilized on a tC18 Plus Sep Pak (Waters). The SepPak was flushed first with 5 mL of ddH$_2$O then 30 mL of air. $^{18}$FB-Polypeptide was isolated in a minimal amount of ethanol by first eluting the void volume (approx. 0.5 mL) followed by collecting 250 to 300 µL of eluent in a separate flask. RP-HPLC analysis was performed on the isolated product in order to establish radiochemical and chemical purity. Typically, 10 µL of a 0.1 µCi/µL solution was injected for post formulation analysis. Isolated radiochemical yields are indicated in Table 9 and are decay corrected from the addition of polypeptide to $^{18}$FBA and radiochemical purity of >99%. Alternatively, $^{18}$F-labeled polypeptides were isolated by NAP5 size exclusion chromatography by diluting the reaction mixture to approximately 0.5 mL with 10 mM PBS and loading onto the gel. The $^{18}$F-labeled polypeptides were isolated by eluting the column with 0.8 mL of 10 mM PBS and used without further modification. These results are illustrated in Table 8, and FIG. 15.

TABLE 8

| Compound | Yield isolated (decay corrected) (%) | HPLC RCP (%) |
| --- | --- | --- |
| Z00477 (SEQ. ID No. 4) | 0.6%/1.2% | 95% |
| Z00342 (SEQ. ID No. 1) | 8.2% (10.7%) | >99% |
| Z02891 (SEQ. ID No. 2) | 6.2% (7.6%) | >99% |

Analytical HPLC conditions used are as follows: Analysis performed on an HP Agilent 1100 with a G1311A QuatPump, G1313A autoinjector with 100 µL syringe and 2.0 mL seat capillary, Phenomenex Gemini C18 column (4.6 mm×150 mm), 5µ, 100 Å (S/N 420477-10), G1316A column heater, G1315A DAD and Ramon Star—GABI gamma-detector. 95:5 ddH$_2$O:CH$_3$CN with 0.05% TFA, Solvent B: CH$_3$CN with 0.05% TFA. Gradient elution (1.0 mL·min$^{-1}$): 0 min 0% B, 1 min 15% B, 21 min 50% B, 22 min. 100% B, 26 min. 100% B, 27 min 0% B, 32 min. 0% B: or gradient elution (1.2 mL min$^{-1}$): 0 min 0% B, 1 min 15% B, 10 min 31% B, 10.5 min. 100% B, 13.5 min 100% B, 14 min 0% B, 17 min 0% B.

Semipreparative HPLC conditions used are as follows: Purification was performed on a Jasco LC with a DG-2080-54 4-line Degasser, an MX-2080-32 Dynamic Mixer and two PU-2086 Plus Prep pumps, an AS-2055 Plus Intelligent autoinjector with large volume injection kit installed, a Phenomenex 5µ Luna C18(2) 100 Å, 250×10 mm, 5µ column with guard (S/N 295860-1, P/N 00G-4252-N0), an MD-2055 PDA and a Carroll & Ramsey Associates Model 105S Analogue Ratemeter attached to a solid-state SiPIN photodiode gamma detector. Gradient elution: 0 min 5% B, 32 min 20% B, 43 min. 95% B, 46 min 95% B, 49 min 5% B, Solvent A: ddH$_2$O:CH$_3$CN with 0.05% TFA, Solvent B: CH$_3$CN with 0.05% TFA.

Example 11

In vivo studies were carried out with female CD-1 nude mice (Charles River Labs, Hopkinton, Mass.) with an age range between 6 and 15 weeks. Mice were housed in a ventilated rack with food and water ad libitum and a standard 12 hour day-night lighting cycle. For xenografts, animals were injected with 100 µl of cells in PBS. Cells were implanted subcutaneously in the right hindquarter Implantation was performed under isoflurane anesthesia. For SKOV3, between 3×10$^6$ to 4×10$^6$ cells were implanted in each mouse. Under these conditions, useable tumors (100 to 300 µg) were obtained in 3 to 4 weeks in greater than 80% of animals injected.

Mice were given tail-vein injections of 1 ug of $^{18}$F-labeled polypeptide (~4 uCi/1 µg). Mice were placed in filter-paper lined cages until euthanasia. Three mice were euthanized at each timepoint and tissues of interest dissected and counted on a Perkin Elmer Wallac Wizard 1480 Gamma Counter. Data were collected for blood, kidney, liver, spleen, bone and injection site (tail). Urine from cages was pooled with the bladder and also counted. The remaining tissues were counted and the sum of all tissues plus urine for each animal was summed to provide the total injected dose. The percent injected dose for each organ was determined based on this total, and organs were weighed for determination of the percent injected dose per gram, (% ID/g). Data is reported as mean value for all three mice in the timepoint with error bars representing the standard deviation of the group.

Figure 16:
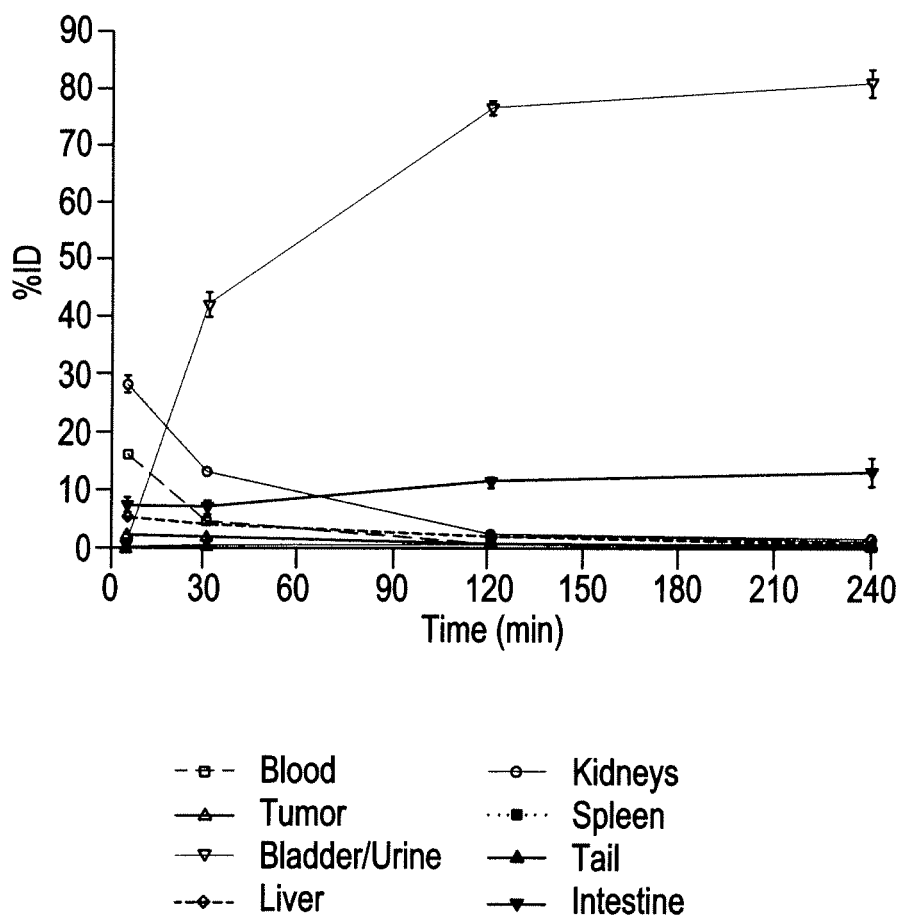
FIG. 16 is a graph of the biodistribution profile (% ID, % injected dose) of the Z02891 (SEQ. ID No. 2) polypeptide labeled with $^{18}$F from SKOV3-tumored animals.
Figure 17:
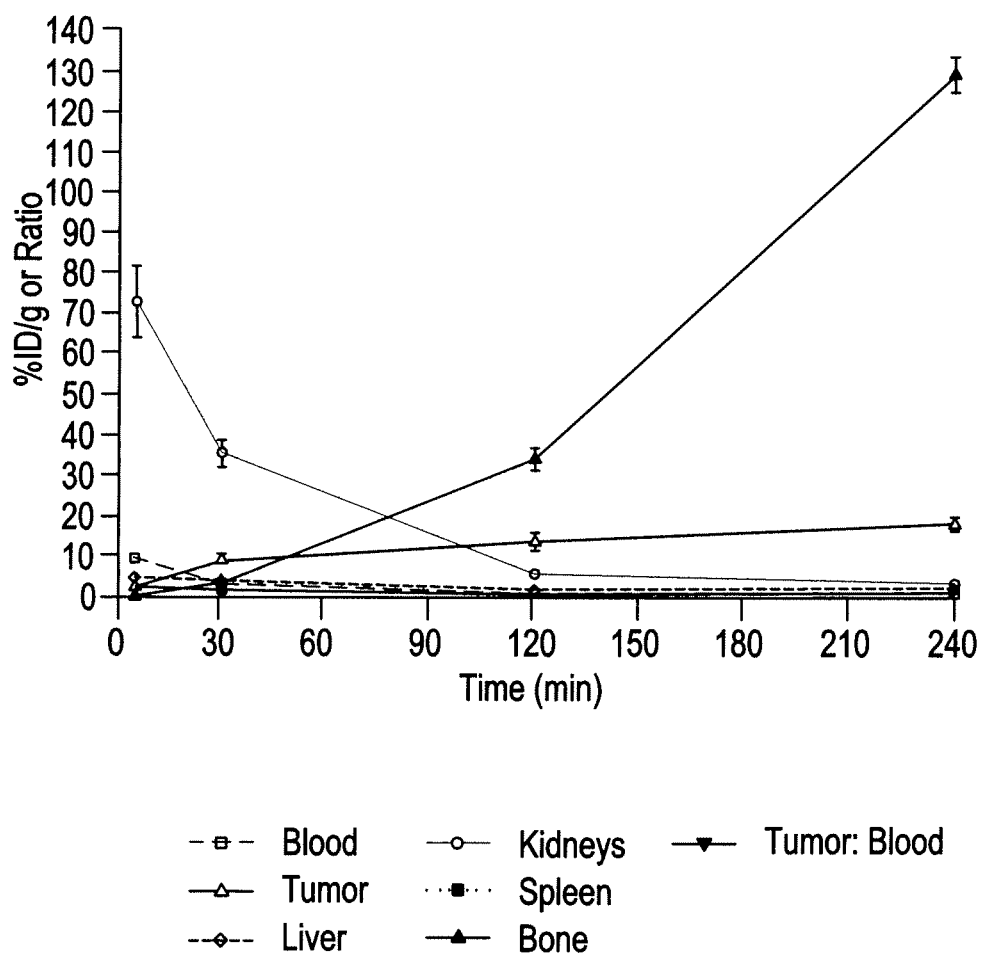
FIG. 17 is a graph of the biodistribution profile of Z02891 (SEQ. ID No. 2) polypeptide labeled with $^{18}$F (% ID, % injected dose) and the tumor: blood ratio from SKOV3-tumored animals.
Figure 18:
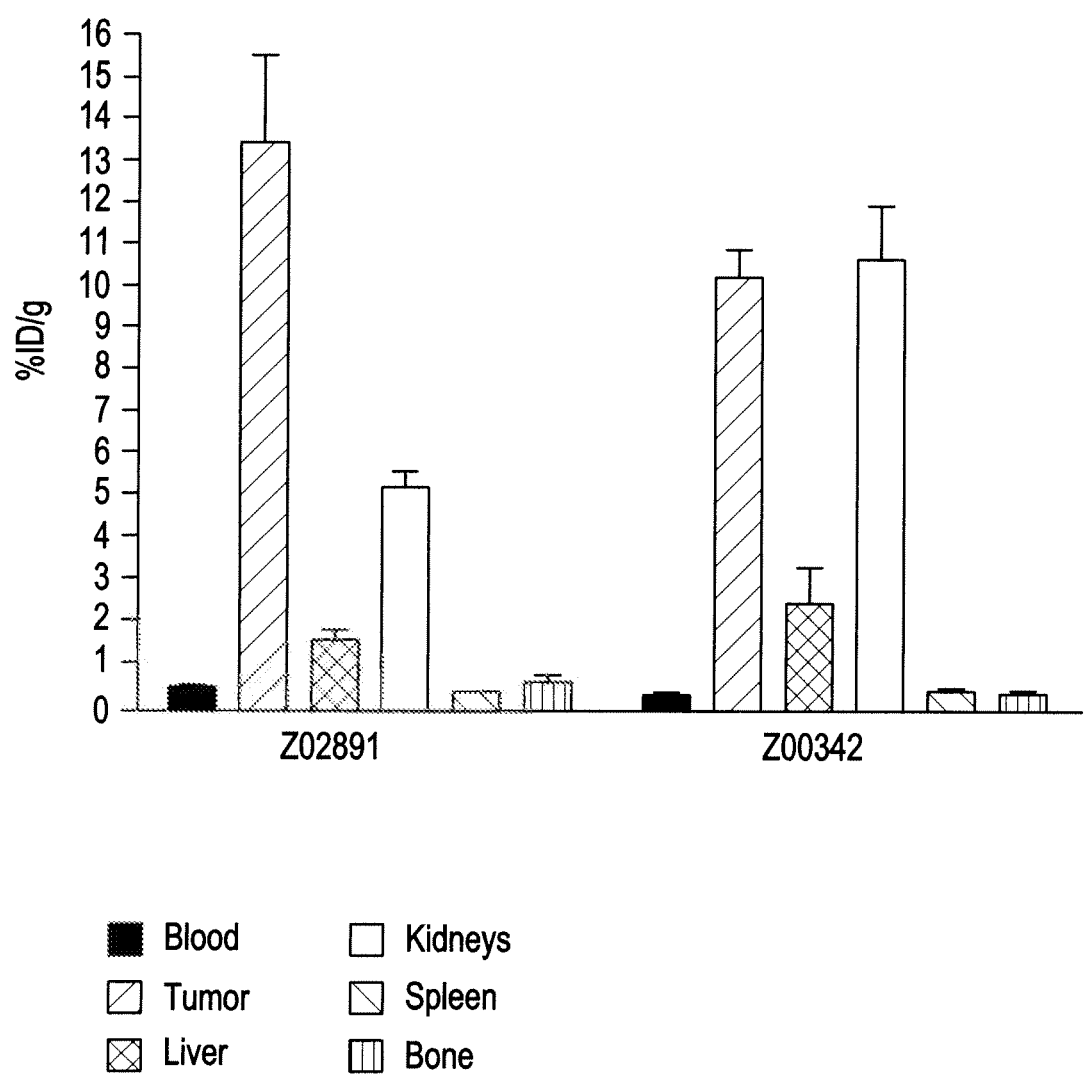
FIG. 18 is bar graph of the biodistribution profile (% ID, % injected dose) of $^{18}$F labeled Z00342 (SEQ. ID No. 1) and $^{18}$F labeled Z02891 (SEQ. ID No. 2) in blood, tumor, liver, kidneys, spleen and bone samples.

The polypeptides underwent biodistribution studies in SKOV3 cell xenograft models. Four time points were taken over four hours (5, 30, 120, and 240 minutes post-injection). Complete biodistribution data are included in Table 12 (% ID/g Z02891 (SEQ. ID No. 2) $^{18}$F-fluorobenzyl oxime in SKOV3 Tumor Bearing Mice) and table 13 (% ID/g Z00342 (SEQ. ID No. 1) $^{18}$F-fluorobenzyl oxime in SKOV3 Tumor Bearing Mice). FIGS. 16, 17 and 18 show the tumor, blood, tumor: blood, and clearance curves for these tests.

The Z02891 (SEQ. ID No. 2) $^{18}$F-fluorobenzyl oxime polypeptide shows strong tumor uptake in target-expressing SKOV3 tumors, with a value of 17.47±2.89 (n=3) of the injected dose per gram of tissue at 240 minutes post-injection (PI). Tumor: blood ratios were approximately 3, 34, and 128 at 30, 120, and 240 min post injection, respectively. The Z00342 (SEQ. ID No. 1) $^{18}$F-fluorobenzyl oxime polypeptide shows strong tumor uptake in target-expressing SKOV3 tumors, with a value of 12.45±2.52 (n=3) of the injected dose per gram of tissue at 240 minutes PI. Tumor: blood ratios were approximately 3, 32 and 53 at 30, 120 and 240 min post injection, respectively.

The polypeptides exhibit a monoexponential clearance from the blood with half-lives of less than two minutes. This clearance of Z02891 (SEQ. ID No. 2) is primarily mediated by the kidneys, with 0.95±0.07 (n=3) ID/organ at 240 min PI. Activity is secreted primarily in the urine. Polypeptide uptake in the spleen was minimal, and low uptake in the liver is observed, ca. 1.8% ID/organ (equivalent in value in mice to % ID/g) over the course of the study (four hours post injection).

for 15 minutes; removing a small aliquot (<5 μL) for analytical HPLC analysis is done to assess the status of the reaction. The reaction mixture is diluted to a minimum 1:1 mixture of ddH$_2$O: Acetonitrile mixture containing 0.1% TFA in preparation for semi-preparative HPLC purification. $^{123}$IB-Polypeptide is isolated and purified by semi-preparative HPLC or NAP5 size exclusion chromatography. The HPLC fraction containing the product is further diluted (5:1) with ddH$_2$O and subsequently immobilized on a tC18 Plus Sep Pak (Waters). Flushing the SepPak first with 5 mL of ddH$_2$O then 30 mL of air gives the $^{123}$IB-Polypeptide in a minimal amount of ethanol by first eluting the void volume (approx. 0.5 mL) followed by collecting 250 to 300 μL of eluent in a separate flask. RP-HPLC analysis is performed on the isolated product to establish radiochemical and chemical purity.

Example 13

Preparation of $^{67}$Ga-NOTA-Z00477 (SEQ ID No. 3)

Figure 19:
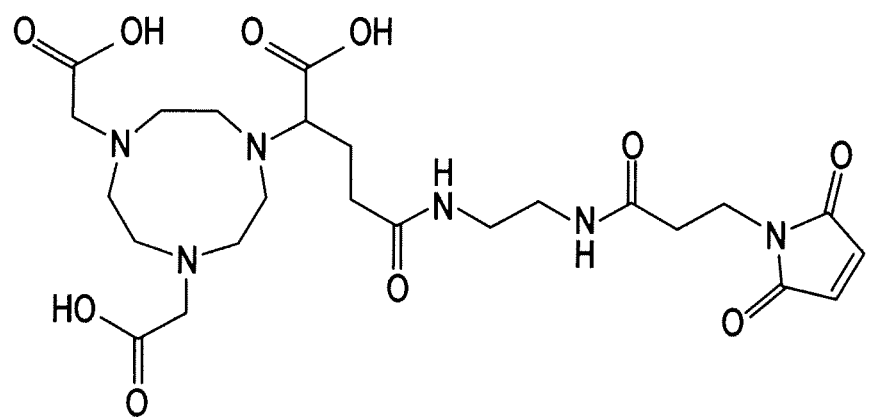
FIG. 19 is a diagram of the chemical structure of the Mal-NOTA linker.

Polypeptide Z00477 (SEQ. ID 3) was labeled with Ga, specifically $^{67}$Ga, after a NOTA (1,4,7-triazacyclononane-N, N',N"-triacetic acid) chelator was conjugated to the polypeptide. (FIG. 19)

Bioconjugation of Mal-NOTA to polypeptide molecules was accomplished as follows. The polypeptide was dissolved with freshly degassed PBS buffer (1×, pH 7.4) at a concentration of approximately 1 mg/mL. The disulfide linkage in the polypeptide was reduced by the addition of DTT solution

TABLE 9

Z02891 (SEQ. ID No. 2) $^{18}$F-fluorobenzyl oxime uptake (% ID/g) in SKOV-3 tumor bearing mice

|        | 5 Minutes         | 30 Minutes        | 120 Minutes        | 240 Minutes       |
|--------|-------------------|-------------------|--------------------|-------------------|
| Blood  | 9.23 ± 0.68 (n = 3)  | 2.91 ± 0.23 (n = 3)  | 0.40 ± 0.07 (n = 3)   | 0.14 ± 0.02 (n = 3)  |
| Tumor  | 2.39 ± 1.13 (n = 3)  | 8.91 ± 2.09 (n = 3)  | 13.47 ± 3.61 (n = 3)  | 17.47 ± 2.89 (n = 3) |
| Liver  | 4.68 ± 0.45 (n = 3)  | 3.85 ± 0.95 (n = 3)  | 1.57 ± 0.42 (n = 3)   | 1.59 ± 0.83 (n = 3)  |
| Kidney | 72.42 ± 15.61 (n = 3)| 35.02 ± 5.76 (n = 3) | 5.22 ± 0.65 (n = 3)   | 2.49 ± 0.17 (n = 3)  |
| Spleen | 3.04 ± 1.15 (n = 3)  | 1.46 ± 0.05 (n = 3)  | 0.37 ± 0.01 (n = 3)   | 0.26 ± 0.04 (n = 3)  |

TABLE 10

Z00342 (SEQ. ID No. 1) $^{18}$F-fluorobenzyl oxime uptake (% ID/g) in SKOV-3 tumor bearing mice

|        | 5 Minutes         | 30 Minutes        | 120 Minutes        | 240 Minutes       |
|--------|-------------------|-------------------|--------------------|-------------------|
| Blood  | 7.38 ± 0.72 (n = 3)  | 1.76 ± 0.09 (n = 3)  | 0.33 ± 0.08 (n = 3)   | 0.87 ± 0.98 (n = 3)  |
| Tumor  | 2.54 ± 0.00 (n = 2)  | 4.97 ± 3.14 (n = 3)  | 10.30 ± 1.08 (n = 3)  | 12.45 ± 2.52 (n = 3) |
| Liver  | 8.29 ± 0.41 (n = 3)  | 6.94 ± 0.92 (n = 3)  | 2.54 ± 1.44 (n = 3)   | 1.41 ± 0.35 (n = 3)  |
| Kidney | 78.93 ± 2.93 (n = 3) | 30.94 ± 4.93 (n = 3) | 10.75 ± 2.17 (n = 3)  | 4.91 ± 0.63 (n = 3)  |
| Spleen | 3.85 ± 0.51 (n = 3)  | 1.77 ± 0.34 (n = 3)  | 0.47 ± 0.08 (n = 3)   | 0.23 ± 0.05 (n = 3)  |

General.

All reactions are performed either under a nitrogen atmosphere or in a crimp-top sealed vial purged with nitrogen. Optima™-grade acetonitrile is used as both HPLC and reaction solvents.

Example 12

[$^{123}$I]4-iodobenzaldehyde ($^{123}$I BA) is added to a high recovery vial (2 mL, National Scientific) containing the polypeptide-ONH$_2$ (Z02891, SEQ. ID No. 2), 0.35-0.5 mg). The reaction commences by dissolving the polypeptide in 25 μL of ddH$_2$O and adding 8 μL of trifluoroacetic acid followed by the addition of $^{123}$IIBA in methanol. The vessel is capped, crimped, placed in a heating block and maintained at 60° C.

in freshly degassed PBS buffer (1×, pH 7.4). The final concentration of DTT was 20 mM. The reaction mixture was vortexed for 2 hours and passed through a Zeba desalt spin column (Pierce Technologies) pre-equilibrated with degassed PBS buffer (1×, pH 7.4) to remove excess of DTT reagent. The eluted reduced polypeptide molecule was collected, and the bifunctional compound mal-NOTA was added (15 equivalents per equivalent of the polypeptide) as a solution in DMSO, and the mixture was vortexed at room temperature. The reaction was allowed to proceed overnight to ensure the complete conversion of the polypeptide molecules.

Figure 20A:
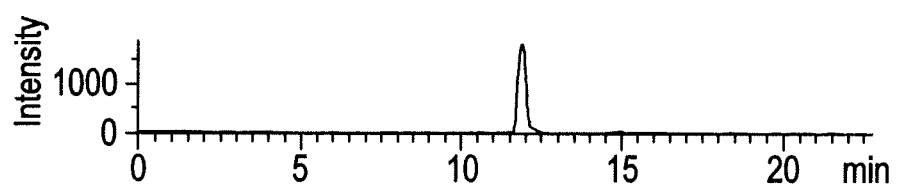
FIG. 20A is a graph of the electrospray ionization time of flight mass spectrum (ESI-TOF-MS), and 20B is a graph of the ESI-TOF-MS mass deconvolution result for Z00477 (SEQ. ID No. 3)-NOTA.

The HPLC purification was performed on a MiCHROM Magic C18AQ 5μ 200 A column (MiChrom Bioresources, Auburn, Calif.). Solvent A: H$_2$O (with 0.1% formic acid), Solvent B: CH$_3$CN (with 0.1% formic acid). Gradient: 5-100% B over 30 mins (FIG. 20A)

The fractions containing desired product were combined and neutralized with 100 mM ammonium bicarbonate solution, and the solvents were removed by lyophilization to give the conjugated polypeptide as a white solid.

Figure 20B:
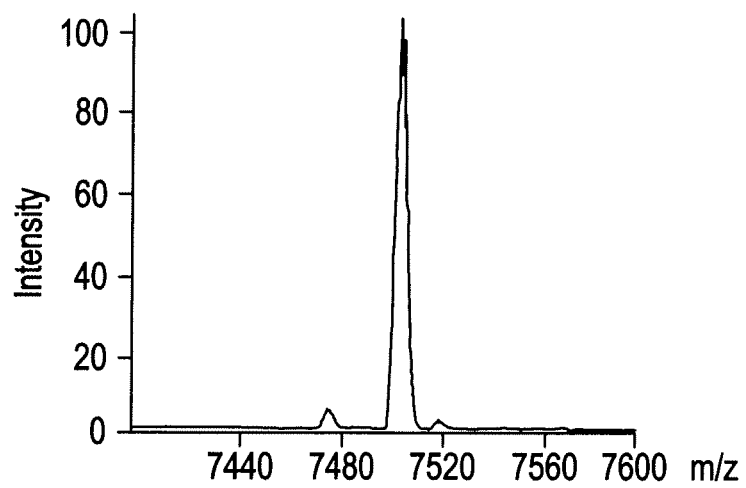

LC-MS analysis of the purified product confirmed the presence of the desired product, and the MW suggested that only one NOTA chelator was added to the polypeptide construct (calculated MW: 7504 Da. found: 7506 Da for Z00477 (SEQ. ID No. 3)-NOTA). (FIG. 20B)

Figure 21:
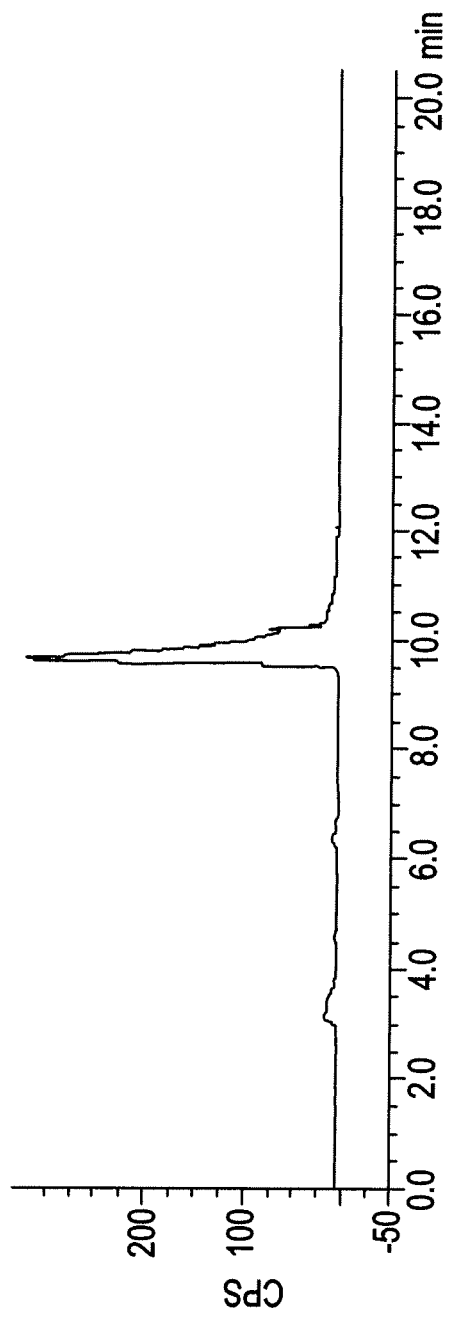
FIG. 21 is a graph of the reverse phase HPLC gamma trace for the crude reaction mixture of $^{67}$Ga-labeled Z00477 (SEQ. ID No. 3)-NOTA after 1 hour of reaction.
Figure 22:
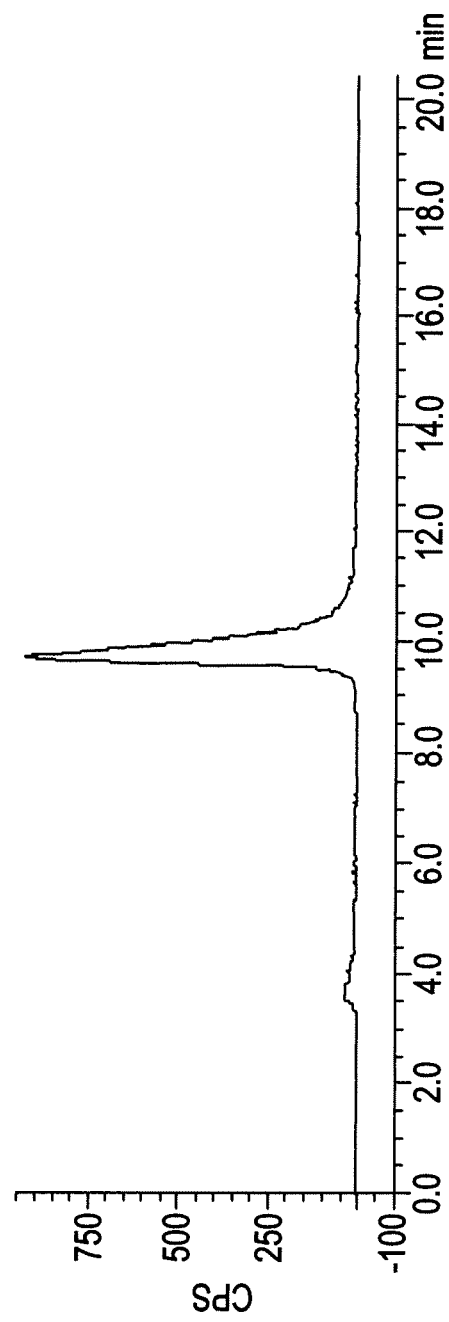
FIG. 22 is a graph of the reverse phase HPLC gamma trace for the purified $^{67}$Ga-labeled NOTA Z00477 (SEQ. ID No. 3)-NOTA polypeptide.

Radiolabeling was subsequently accomplished as follows: 25 µl HEPES solution (63 mM) was initially added to a screw top vial followed by 10 µl $^{67}$GaCl$_3$ (GE Healthcare) in 40.5 MBq of 0.04M HCl. 30 µg (MW=7506, 4.0×10$^{-9}$ mol) of the NOTA Z00477 (SEQ. ID No. 3) in 30 µl H$_2$O was then added to the reaction mixture to give a final NOTA Z00477 (SEQ. ID No. 3) concentration of 61 µM with a pH of 3.5-4.0. The reaction vial was sealed and the reaction maintained at ambient temperature. Reverse phase HPLC analysis of the crude reaction mixture determined the radiochemical purity of the $^{67}$Ga-NOTA Z00477 (SEQ. ID No. 3) was determined to be 95% by HPLC after 2 hours at room temperature. (FIG. 21) The $^{67}$Ga-NOTA Z00477 (SEQ. ID No. 3) was purified by HPLC after a reaction time of 1 day. 22 MBq of $^{67}$Ga-NOTA Z00477 (SEQ. ID No. 3) was injected onto the HPLC for the purification. 15 MBq of the $^{67}$Ga labeled product was obtained from the purification (radiochemical yield=68%). HPLC solvents were removed under vacuum to give a solution with an approximate volume of 0.5 mL. Approximately 1.45 mL of Dulbecco's phosphate buffered saline was then added to give a final solution at pH 6-6.5 with a radioactivity concentration of 7.7 MBq/mL. Purified, formulated $^{67}$Ga-NOTA Z00477 (SEQ. ID No. 3) was found to be stable for at least 2 hr at room temperature. (RCP=96% by HPLC) (FIG. 22).

Analytical HPLC conditions used are as follows: A Grace Vydac C$_4$ protein 5 micron, 300 Å, 4.6×250 mm HPLC column. Solvent A=95/5 H$_2$O/MeCN in 0.05% trifluoroacetic acid (TFA) Solvent B=95/5 CH$_3$CN/H$_2$O in 0.05% TFA. HPLC gradient (Min/% B): 0/0, 4/20, 16/60, 20/100, 25/100, 26/0.

Semi-preparative HPLC conditions used are as follows: Column: Grace Vydac C4 protein 5 micron, 300 Å, 4.6×250 mm Solvent A=95/5 H$_2$O/MeCN in 0.05% trifluoroacetic acid (TFA) Solvent B=95/5 CH$_3$CN/H$_2$O in 0.05% TFA. HPLC gradient (Min/% B): 0/0, 4/20, 16/60, 20/100, 25/100, 26/0.

General

Recombinant HER2 Z28921-Cys was purchased from Affibody AB, Sweden, Eei-aminooxyacetic acid succinic ester from IRIS Biotech, and di-tert-butyldifluorosilane was purchased from Fluorochem. Reagents and solvents were purchased from IRIS Biotech, Merck, Romil and Fluka.

Analytical LC-MS spectra were recorded on a Thermo Finnigan MSQ instrument by electrospray ionisation (ESI) operated in positive mode coupled to a Thermo Finnigan Surveyor PDA chromatography system using the following conditions: Solvent A=H2O/0.1% TFA and solvent B=ACN/0.1% TFA if not otherwise stated, flow rate: 0.6 mL/min, column: Phenomenex Luna 3 µm C18 (2) 20×2 mm, detection: UV 214/254 nm.

Semi-preparative reversed-phase HPLC runs were performed on a Beckman System Gold chromatography system using the following conditions: Solvent A=H2O/0.1% TFA and solvent B=ACN/0.1% TFA if not otherwise stated, flow rate: 10 mL/min, column: Phenomenex Luna 5 µm C18 (2) 250×21.2 mm, detection: UV 214 nm.

Preparative reversed-phase HPLC runs were performed on a Waters Prep 4000 system using the following conditions: Solvent A=H2O/0.1% TFA and solvent B=ACN/0.1% TFA if not otherwise stated, flow rate: 50 mL/min, column: Phenomenex Luna 10µ C18 (2) 250×50 mm, detection: UV 214/254 nm.

Abbreviations:

Ala (A): Alanine
Arg (R): Arginine
Asn (N): Asparagine
Asp (D): Aspartic acid
ACN: Acetonitrile
Boc: tert-Butyloxycarbonyl
Cys (C): Cysteine
DIPEA: Diisopropylethylamine
DMF: N,N-Dimethylformamide
DMAB: 4-dimethylamino-benzaldehyde
DOTA: 1,4,7,10-tetraazacyclododecane-1,4,7,10-tetraacetic acid
EDT: 1,2-Ethanedithiol
EMS: Ethyl methyl sulphide
ESI: Electrospray ionisation
eq: Equivalent
FBA: 4-Fluorobenzaldehyde
Gln (Q): Glutamine
Glu (E): Glutamic acid
hr(s): Hour(s)
HER2: Human Epidermal growth factor receptor
HOAt: 1-Hydroxy-7-azabenzotriazole
HPLC: High performance liquid chromatography
Ile (I): Isoleucine
LC-MS: Liquid chromatography mass spectroscopy
Leu (L): Leucine
Lys (K): Lysine
Met (M): Methionine
min: Minutes
µm: Micrometre
nm: Nanometre
NMP: 1-Methyl-2-pyrrolidinone
NOTA: 1,4,7-Triazacyclononane-1,4,7-triacetic Acid
PDA: Photodiode array
PET: Positron emission tomography
Phe (F): Phenylalanine
Pro (P): Proline
PyAOP: (7-Azabenzotriazol-1-yloxy)tripyrrolidinophosphonium hexafluorophosphate
Ser (S): Serine
SiFA: 4-(Di-tert-butylfluorosilyl)benzaldehyde
TFA: Trifluoroacetic acid
Thr (T): Threonine
TIS: Triisopropylsilane
Trp (W): Tryptophan
Tyr (Y): Tyrosine
Val (V): Valine

Example 14

Semi-Automated Radiosynthesis of Compound 2

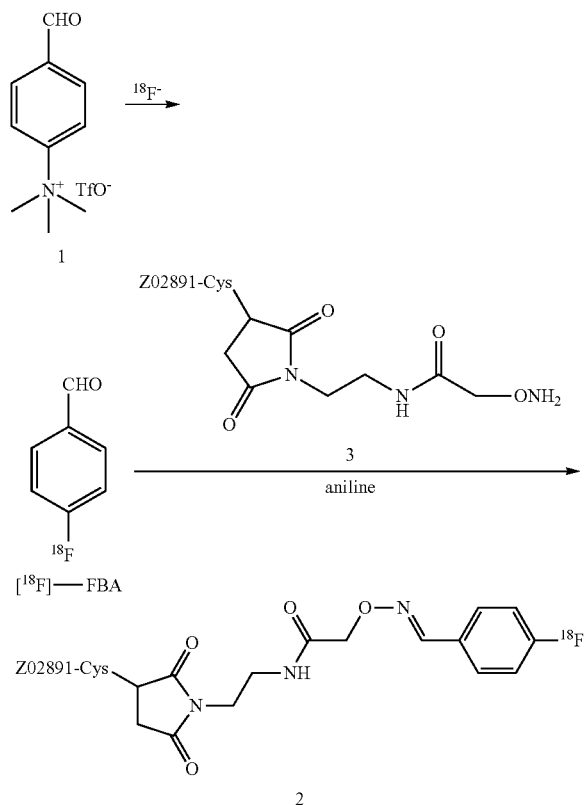

Figure 23:
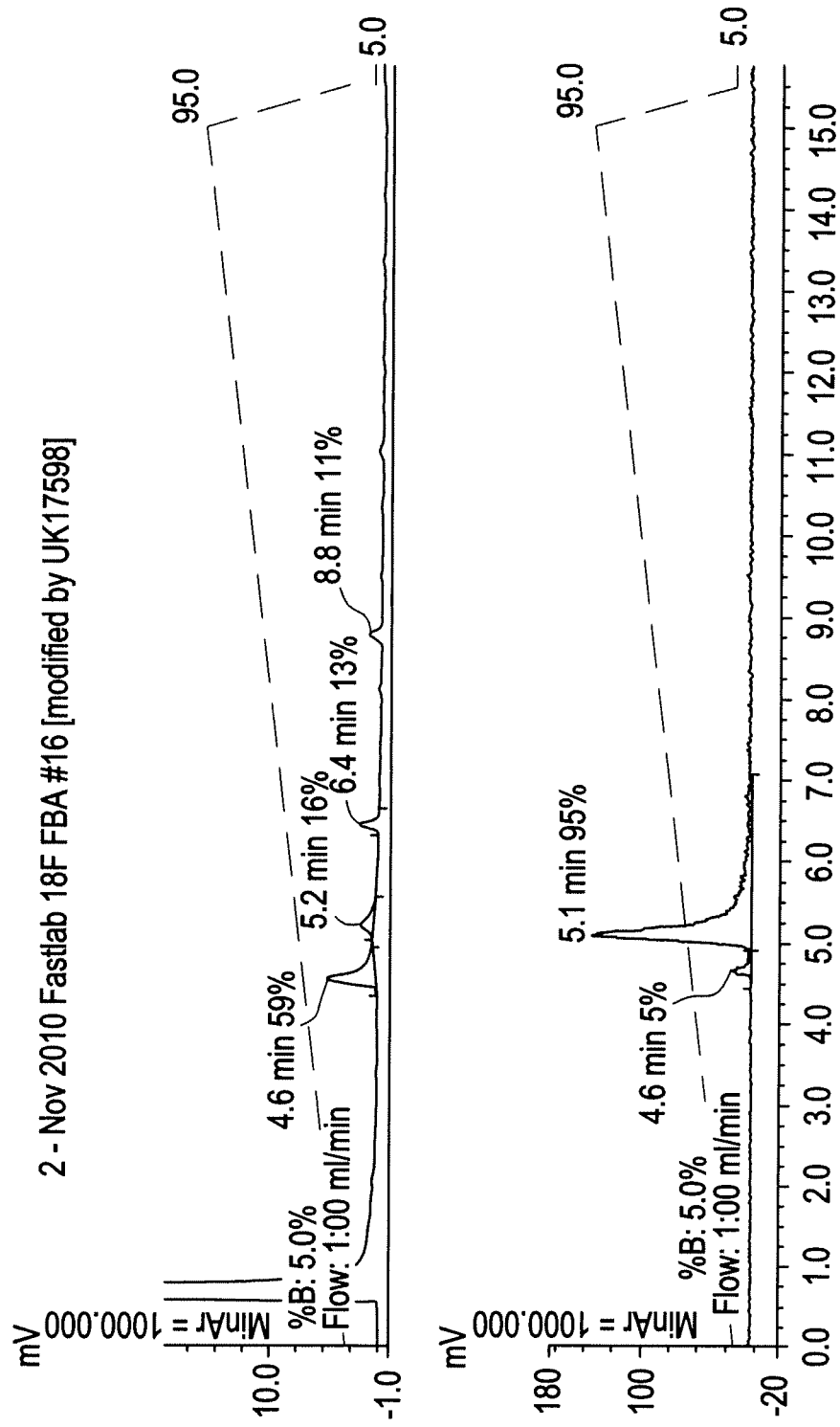
FIG. 23 is an analytical HPLC of formulated 2 [top: UV channel at 280 nm showing ascorbate, 0.5 min and peptide precursor 3, 4.5 min; bottom: radioactivity channel showing 2, 5.1 min (RCP 95%) and a decomposition product at 4.6 min.

A FASTlab™ platform (GE Healthcare) was used to prepare [18F]Fluorobenzaldehyde ("[18F]FBA") yielding typically 7 GBq of [18F]FBA in ethanol (1.5 mL, non-decay corrected yields 12-54%). A small fraction (92 µL) of this [18F]FBA solution was then manually conjugated to the aminoxy precursor 3 (0.4 mg, 55 nmol) in the presence of aniline hydrochloride (3.2 mg, 25 µmol) in water (138 µL) in a silanised P6 vial. The mixture was heated at 70° C. for 20 minutes using a Peltier heater. 2 was isolated via size exclusion chromatography (NAP5 cartridge, GE Healthcare). An initial elution with 0.25 mL saline/0.1% sodium ascorbate was discarded. A subsequent 0.75 mL saline/0.1% sodium ascorbate elution containing 2 was collected and formulated with the same elution mixture at pH 5-5.5 to give the desired radioactive concentration. Non-decay corrected yields of the isolated 2 from the conjugation step were 17-38%, and the radiochemical purity (RCP) values for the manually prepared 2 were ≥95%. (TLC system: Perkin Elmer Instant Imager using C18 reversed-phase sheets with water/30% acetonitrile (v/v) as mobile phase. The labelled peptide remained at the origin.). The product was further analysed by HPLC using a Gilson 322 pump with a Gilson UV/ViS 156 detector, a Bioscan Flow-Count radioactivity detector, and a Luna C18 Phenomenex column (50×4.6 mm, 3 nm) or a Luna C18 Phenomenex column (150×4.6 mm, 5 nm). The mobile phase comprised of solvents A (0.1 M ammonium acetate) and B (acetonitrile) running at 1 mL/min with a linear gradient (5-95 B in 15 min). The UV absorbance was measured at 280 and 350 nm FIG. 23 shows a representative example of an analytical HPLC trace of the formulation of 2.

Example 14a

Preparation of Compound 3

(i) Preparation of Eei-aminooxyacetyl-maleimide

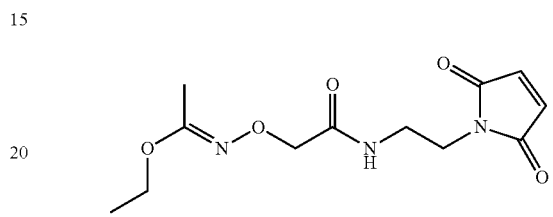

N-(2-Aminoethyl)maleimide TFA salt (51 mg, 0.20 mmol) and Eei-AOAc-OSu (77 mg, 0.30 mmol) were dissolved in NMP (2 mL). Sym.-collidine (80 µL, 0.6 mmol) was added and the reaction mixture stirred for 70 min. The reaction mixture was diluted with water (7 mL) and the product, eei-aminooxyacetyl-maleimide, purified by semi-preparative HPLC. Purification using semi-preparative HPLC (gradient: 15-30% B over 40 min where A=water/0.1% acetic acid and B=ACN) affording 43 mg (75%) pure Eei-aminooxyacetyl-maleimide. The purified material, eei-aminooxyacetyl-maleimide, was characterised by LC-MS (gradient: 10-40% B over 5): $t_R$: 1.93 min. found m/z: 284.1, expected $MH^+$: 284.1

(ii) Preparation of Compound 3

Recombinant Z02891-Cys (144 mg, 0.205 mmol)(purchased from Affibody AB, Sweden) and eei-aminooxyacetyl-maleimide (17 mg, 0.60 mmol) were dissolved in water (3 mL). The solution was adjusted to pH 6 by addition of ammonium acetate and the reaction mixture shaken for 90 min. The reaction mixture was diluted with water (7 mL) and the product purified by semi-prep HPLC affording 126 mg lyophilised Eei-protected product. The eei-protected product was treated with 2.5% TFA/water (16 mL) under a blanket of argon for 20 min. The solution was diluted with water (144 mL), frozen using isopropanol/dry-ice bath under a blanket of argon and lyophilised affording 149 mg (100%) Z02891-Cys-maleimide-aminooxyacetyl (3). Lyophilised Z02891-Cys-maleimide-aminooxyacetyl (3) was analysed by analytical LC-MS (gradient: 10-40% B over 5 min, $t_R$: 3.28 min. found m/z: 1811.8, expected $MH_4^{4+}$: 1811.4

Example 15

Automated Radiosynthesis of Compound 2 Using tC2 SepPak Purification

Figure 24:
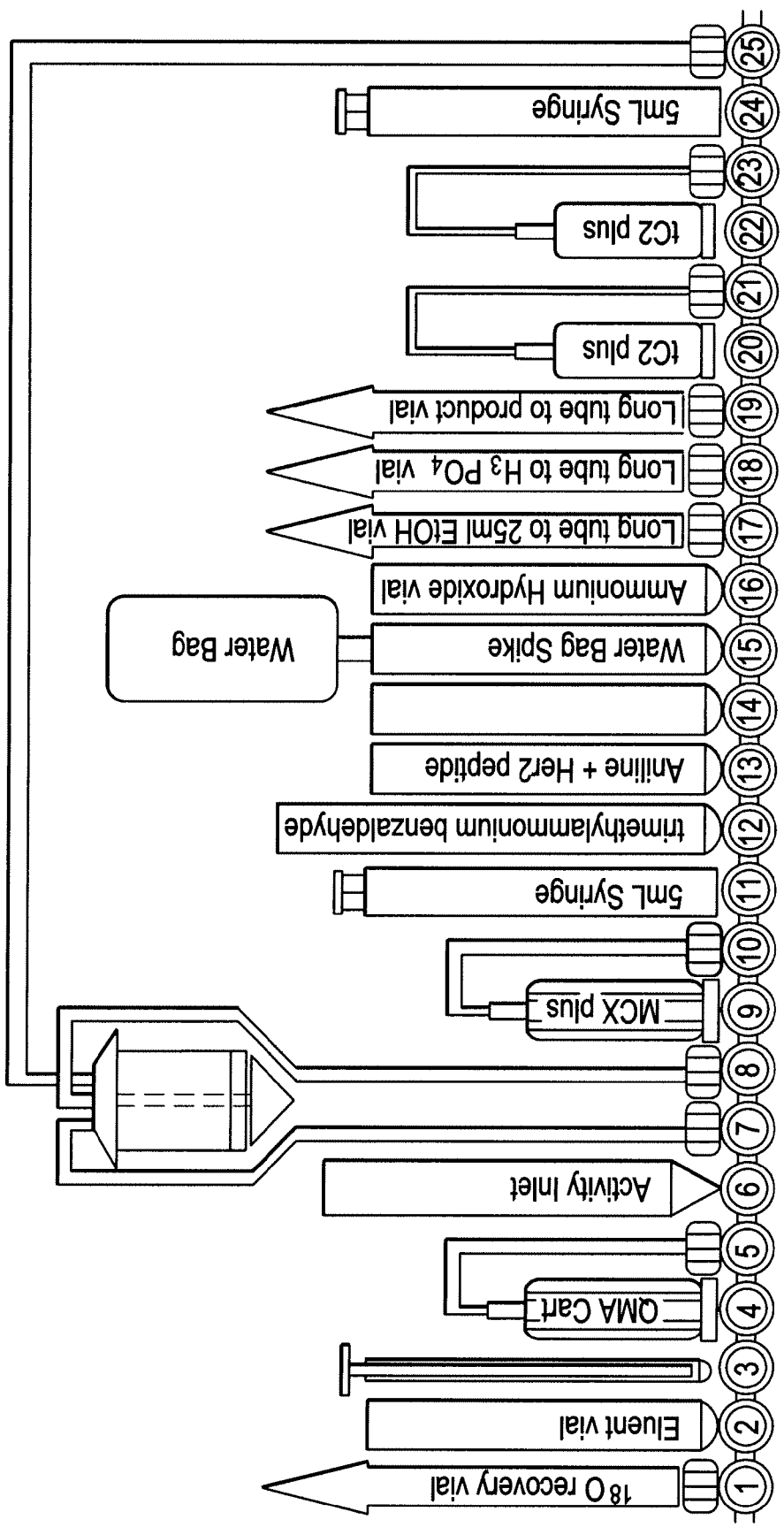
FIG. 24 is a FASTlab™ cassette layout for the preparation of 2 using tC2 SepPak purification.
Figure 25:
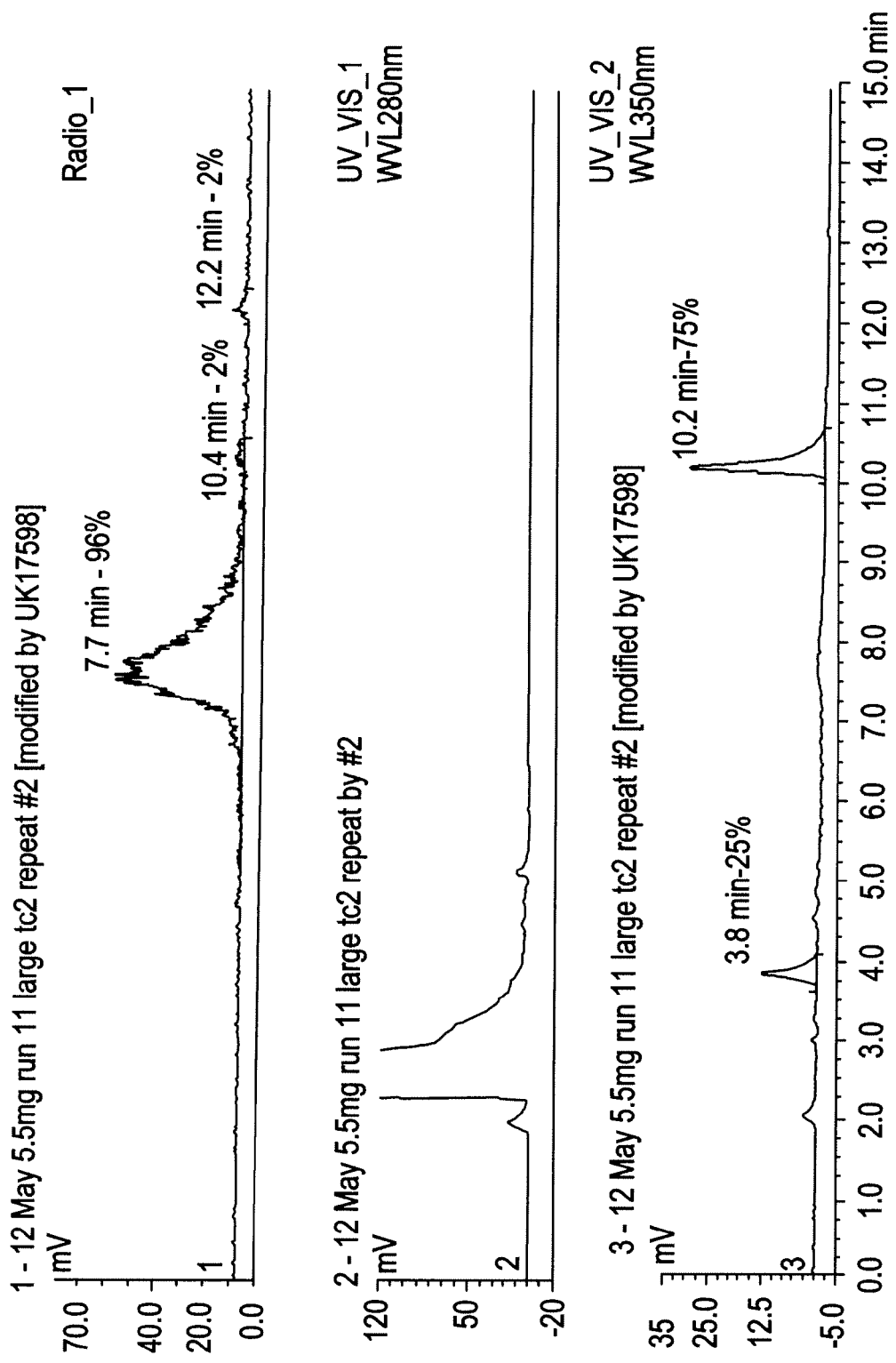
FIG. 25 is an analytical HPLC of formulated 2 prepared using FASTlab™ [top: radioactivity channel, showing 2 (7.7 min), $^{18}$F-FBA (10.4 min) and an unknown impurity (12.2 min); middle: UV channel at 280 nm showing p-aminobenzoic acid formulation additive (3 min); bottom: UV channel at 350 nm showing dimethylaminobenzaldehyde by-product (10.2 min) and an unknown impurity (3.8 min)]

A FASTlab™ cassette was assembled containing a first vial (8.25 mg/21.9 µmol Kryptofix, 1.16 mg/8.4 µmol K₂CO₃, 165 µL water, 660 µL acetonitrile), a second vial (1.5 mg/4.8 µmol triflate 1, 1.5 mL anhydrous DMSO), a third vial (5.5 mg/0.76 µmol 3, 8.2 mg/63 µmol aniline hydrochloride, 0.7 mL ammonium acetate buffer pH 4.5/0.25 M), a fourth vial (4 mL, 4% w/v aqueous ammonia), external vials of ethanol (25 mL) and phosphoric acid (1% w/w, 25 mL), a pre-conditioned QMA light SepPak cartridge, an OASIS MCX SepPak cartridge, and two 'C2 SepPak cartridges. The product vial contained an aqueous solution of p-aminobenzoic acid (0.08% w/w, 19 mL). The cassette layout is shown in FIG. 24.

The required programme sequence was uploaded from the PC control to the synthesizer module and the assembled cassette mounted onto the machine. A water bag and a product vial were attached. A vial containing [¹⁸F]water (300 MBq, 1 mL) was attached to the FASTlab™ module and the radiosynthesis commenced. The process included an azeotropic drying step of the [¹⁸F]-Kryptofix/potassium carbonate complex as eluted from the QMA cartridge, the radiosynthesis of [¹⁸F]FBA, the purification of [¹⁸F]FBA using the MCX cartridge, ammonia solution and elution with ethanol, the conjugation step to produce 2, and the purification and formulation step using phosphoric acid/ethanol on the 'C2 cartridges. The total process took one hour and generated 2 in 33% non-decay corrected radiochemical yield with 94% radiochemical purity.

Example 16

Automated Radiosynthesis of Compound 2 Using Sephadex Purification

Figure 26:
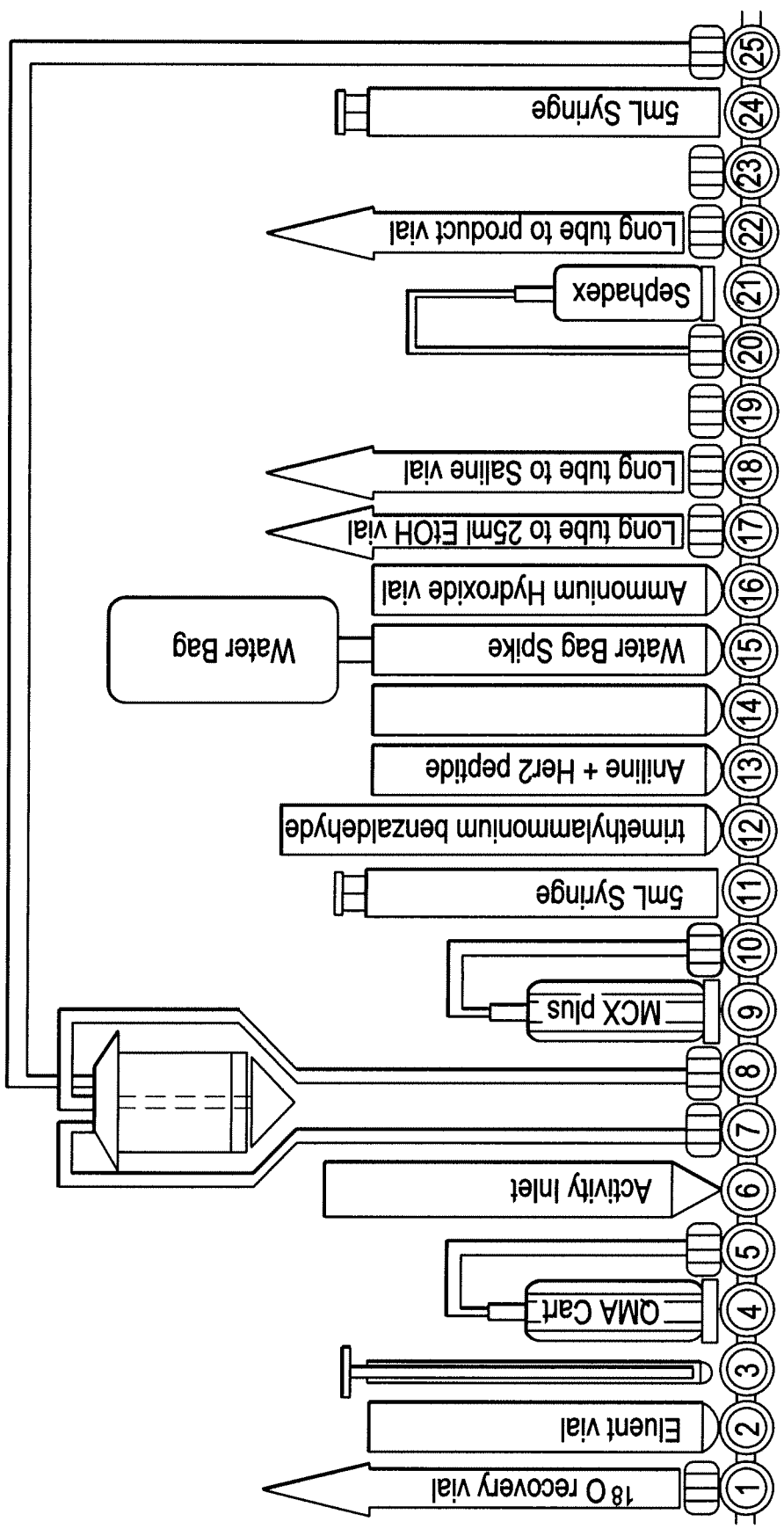
FIG. 26 is a FASTlab™ cassette layout for the preparation of 2 using Sephadex purification.
Figure 27:
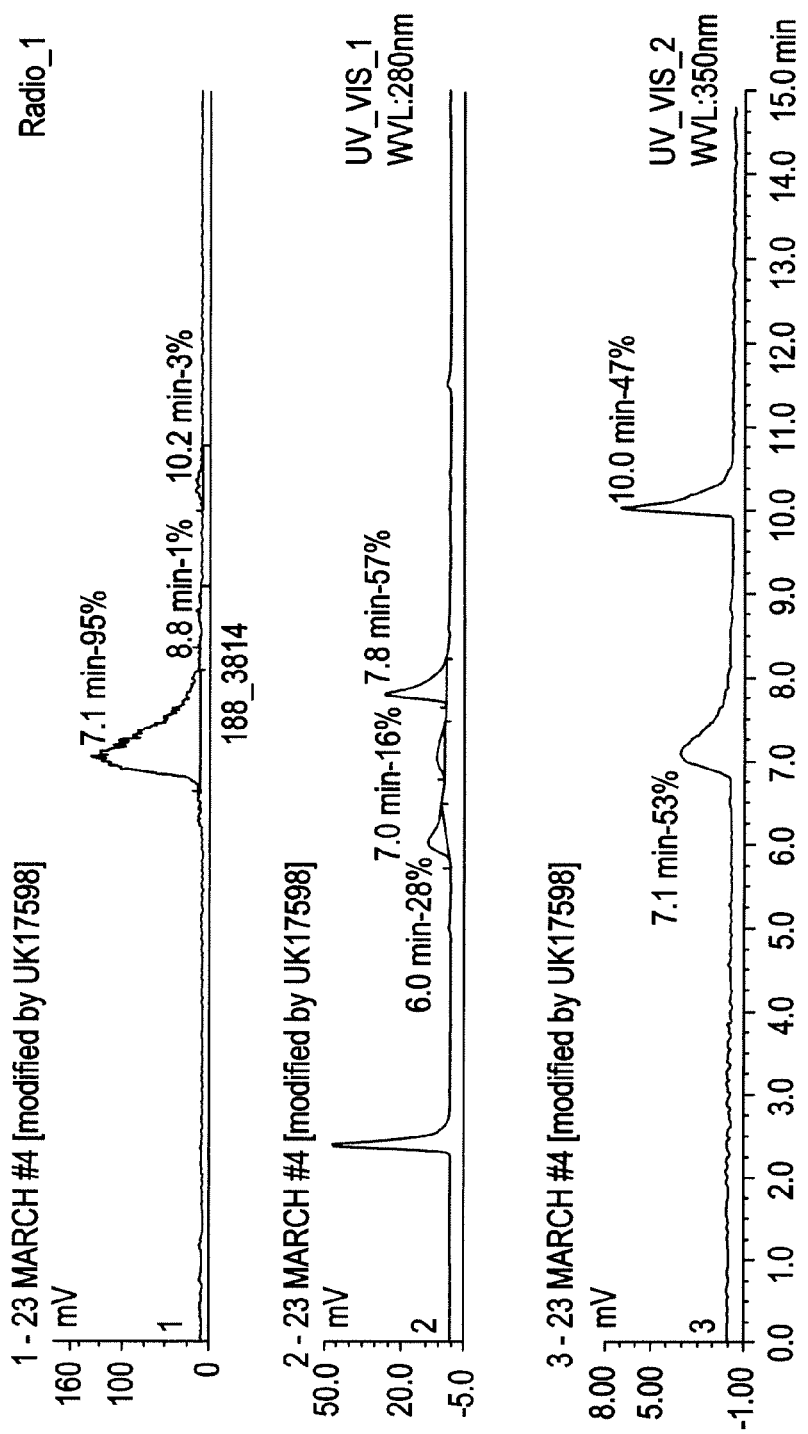
FIG. 27 is an analytical HPLC of formulated 2 prepared using FASTlab with Sephadex purification [top: radioactivity channel, showing 2 (7.1 min), $^{18}$F-FBA (8.8 min) and an unknown impurity (10.2 min); middle: UV channel at 280 nm; bottom: UV channel at 350 nm showing dimethylaminobenzaldehyde by-product (10.0 min)]

A FASTlab™ cassette was assembled containing a first vial (8.25 mg/21.9 µmol Kryptofix, 1.16 mg/8.4 µmol K₂CO₃, 165 µL water, 660 µL acetonitrile), a second vial (1.5 mg/4.8 µmol triflate 1, 1.5 mL anhydrous DMSO), a third vial (5.0 mg/0.69 µmol 3, 8.2 mg/63 µmol aniline hydrochloride, 0.7 mL ammonium acetate buffer pH 4.5/0.25 M), a fourth vial (4 mL, 4% w/v aqueous ammonia), external vials of ethanol (25 mL) and saline (Polyfusor, 0.9% w/v, 25 mL), a pre-conditioned QMA light SepPak cartridge, an OASIS MCX SepPak cartridge, and a custom packed size exclusion cartridge (2 mL, Supelco, Cat. #57608-U) containing dry Sephadex G10 (500 mg, Sigma-Aldrich, Cat. #G10120). The cassette layout is shown in FIG. 26. The radiosynthesis of 2 was performed as described in Example 15. After priming the Sephadex cartridge with saline (5 mL), the crude reaction mixture was pumped through the Sephadex cartridge and pure 2 collected in the product vial. The synthesis time was 40 minutes and the non-decay corrected radiochemical yield was 10%. The radiochemical purity of the product was 95% and the level of DMAB was 0.8 µg/mL. FIG. 27 shows the HPLC analysis of the final product.

Example 17

Radiosynthesis of [18F]AlF-NOTA(COOH)₂-Z02891(SEQ ID No. 2)(5)

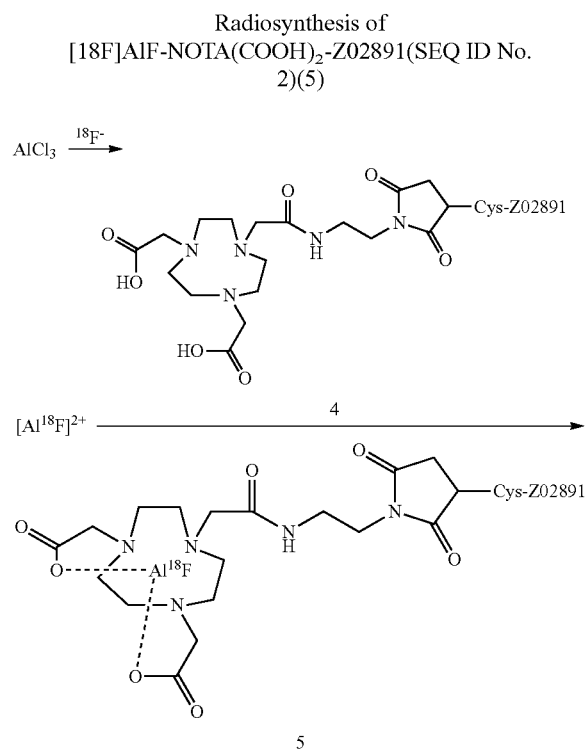

Figure 28:
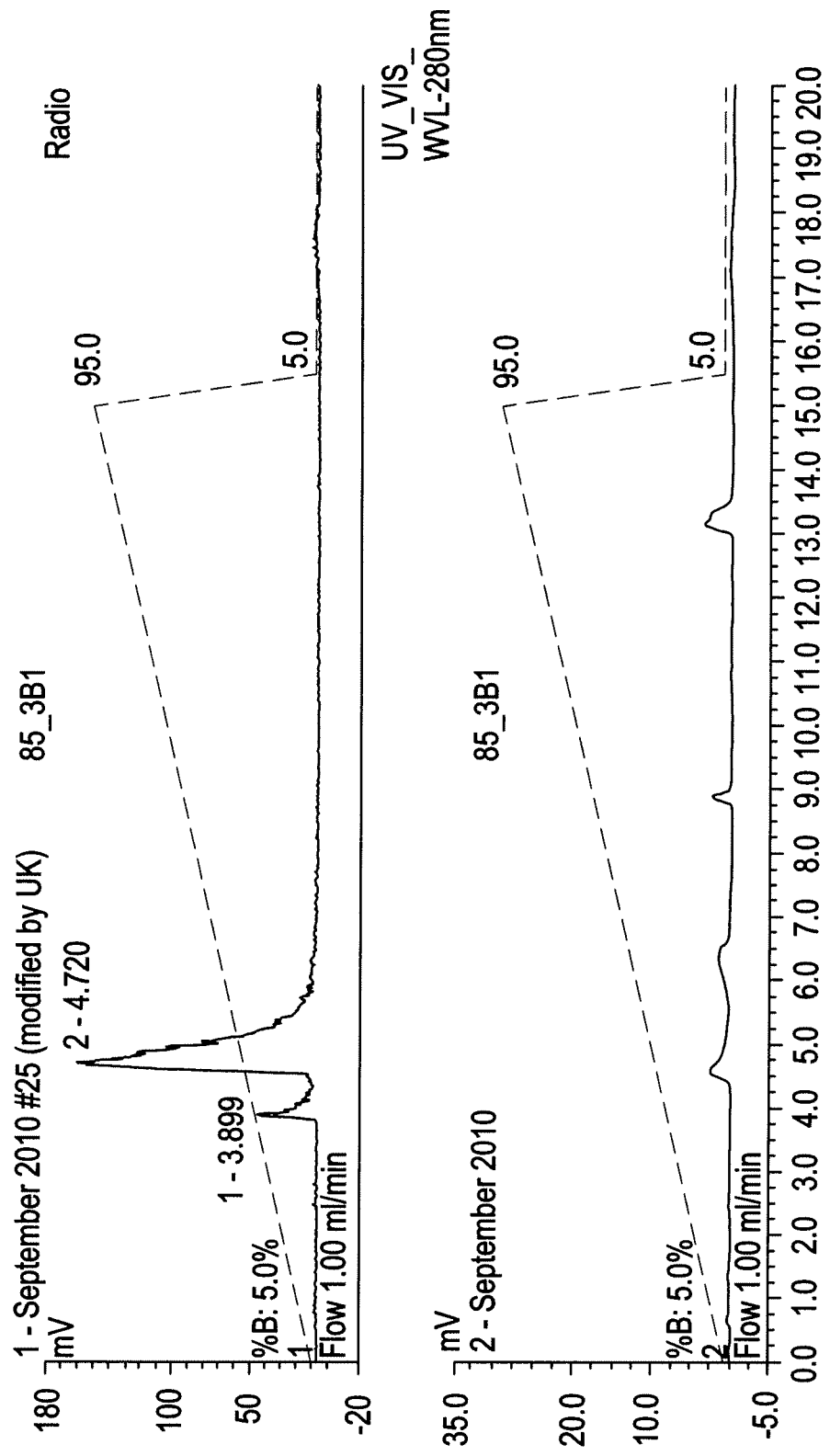
FIG. 28 is an analytical HPLC of formulated 5 [top: radioactivity channel, showing the product (4.7 min, 92%) and a by-product (3.9 min, 8%); bottom: UV channel at 280 nm].

A solution of NOTA(COOH)₂-Z02891 (4) (746 µg, 100 nmol) in sodium acetate buffer (50 µL, pH 4.0, 0.5 M) was mixed with a solution of AlCl₃ (3 µL, 3.33 µg, 25 nmol in sodium acetate buffer, pH 4.0, 0.5 M) in a conical polypropylene centrifuge vial (1.5 mL). This mixture was added to a small volume of [¹⁸F]fluoride (50 µL) in a capped P6 vial. This vial was heated for 15 min at 100° C. After diluting with saline (100 µL), the reaction solution was transferred to a NAP5 size exclusion cartridge (GE Healthcare). The final product was eluted into a P6 vial using saline (750 µL). The labelled peptide 5 was obtained with 11% non-decay corrected radiochemical yield. FIG. 28 shows the analytical HPLC of the formulated product. Table 11 summarises the data of individual runs.

TABLE 11

Summary of [¹⁸F]AlF-NOTA(COOH)₂-Z02891(SEQ ID No. 2)(5) preparations using NAP5 purification.

| Entry | ¹⁸F-Fluoride starting activity (MBq) | ¹⁸F-Fluoride volume (µL) | 5 (MBq) | EOS[a] |
|---|---|---|---|---|
| 1 | 43 | 25 | 2 | 4% |
| 2 | 44 | 25 | 4 | 1% |
| 3 | 127 | 50 | 20 | 16% |
| 4 | 330 | 25 | 35 | 11% |
| 5 | 410 | 50 | 38 | 9% |
| 6 | 134 | 50 | 20 | 15% |
| 7 | 518 | 50 | 55 | 11% |

[a]End of Synthesis radiochemical yield, non-decay corrected

Example 17a

Preparation of Compound 4

(i) Preparation of NOTA(bis-tBu)

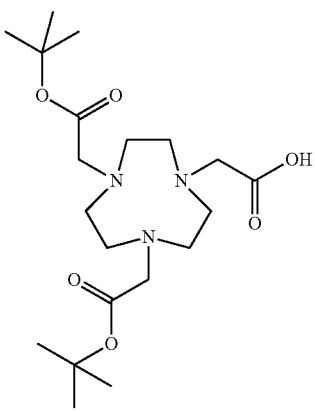 [SMILES: CC(C)(C)OC(=O)CN1CCN(CC(=O)O)CCN(CC(=O)OC(C)(C)C)CC1]

(a) Synthesis of Tetratosyl-N,N'-bis(2-hydroxyethyl)ethylene diamine

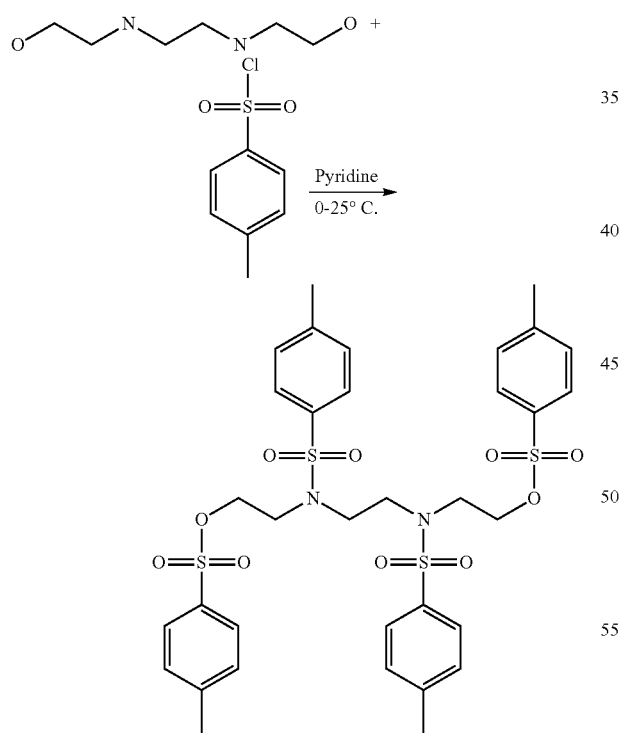

N,N'-bis(2-hydroxyethyl)-ethylenediamine (Aldrich, 14.8 g, 100 mmol) and pyridine (Fluka, 200 mL) was stirred at 0° C. under nitrogen while a solution of toluene-4-sulfonyl chloride (Fluka, 77 g, 400 mmol) dissolved in pyridine (Fluka, 100 mL) was dropped into the solution over a period of 75 minutes. The temperature was slowly raised to room temperature and continued stiffed for 4 hours. Solution was poured into a mixture of ice (250 mL) and hydrochloric acid (concentrated, 250 mL) while stirring to afford a dark sticky oil. Solvents were removed by decantation, product crude washed with water, decanted and re-dissolved in methanol (250 mL). The resulting slurry was isolated by filtration and the crude product was re-dissolved in hot methanol (60° C., 600 mL) and cooled down. Solid product was filtered off and dried in vacuo. Yield 36.36 g (47.5%). Product was verified by NMR.

(b) Synthesis of 1-Benzyl-4-7-ditosyl-1,4,7-triazonane

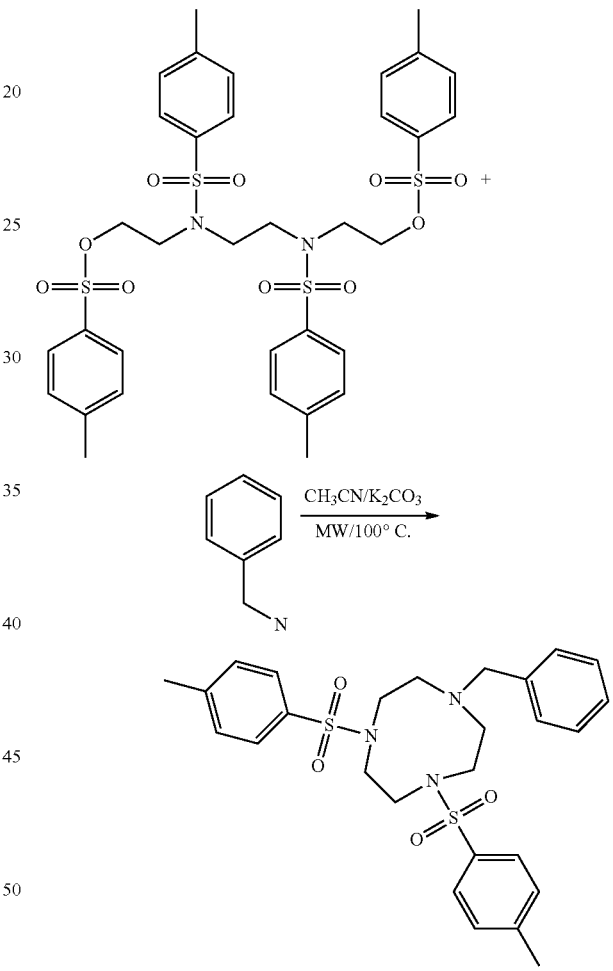

Tetratosyl-N,N'-bis(2-hydroxyethyl)ethylene diamine (See Example 17a(i)(a); 2.0 g, 2.6 mmol), benzyl amine (500 μl, 4.6 mmol), potassium carbonate (Fluka, 792 mg, 5.7 mmol) and acetonitrile (Merck, 25 mL) was heated to 100° C. and stirred overnight. Solvents were removed from solid product by filtration. The solid was washed with acetonitrile (2×10 mL) and solvents were evaporated off. Solids was dissolved in hot ethanol (15 mL) and left for three days in room temperature. Crystals were collected by filtration and dried in vacuum overnight. Product confirmed by LC-MS (Phenomenex Luna C18(2) 2.0×50 mm, 3 μm, solvents: A=water/0.1% trifluoroacetic acid and B=acetonitrile/0.1% trifluoroacetic acid; gradient 10-80% B over 5 min; flow rate 0.6 mL/min, UV detection at 214 and 254 nm, ESI-MS) $t_R$=3.66 min. Yield 1 g (72%).

(c) Synthesis of (4-Benzyl-7-tert-butoxycarbonylmethyl-[1,4,7]triazonan-1-yl)-acetic acid tert-butyl ester

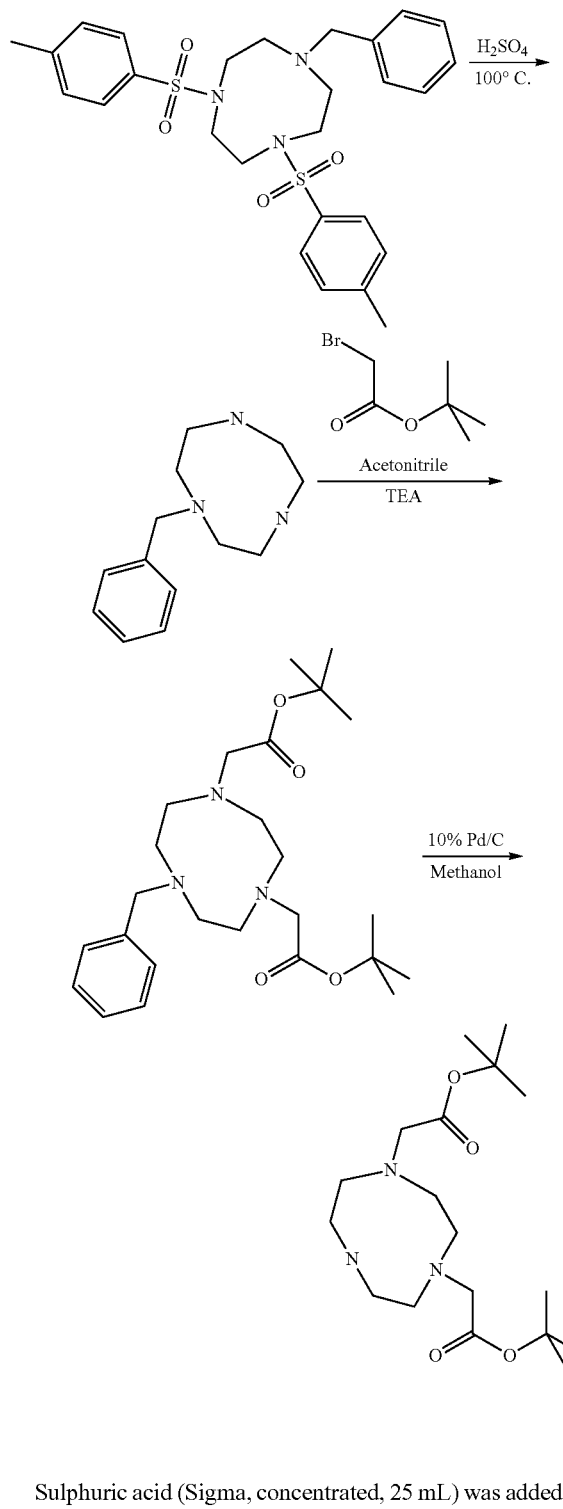

Sulphuric acid (Sigma, concentrated, 25 mL) was added to 1-Benzyl-4-7-ditosyl-1,4,7-triazonane (See Example 17a(i) (b); 2.5 g, 4.7 mmol) while stirring and heated to 100° C. and left for 20 hours. The reaction mixture was cooled to room temperature and added drop wise into diethyl ether (VWR, 500 mL). Product (white precipitate) was filtered off and washed with acetonitrile, chloroform and dichloromethane. Solvents were removed in vacuo. The product crude (986.3 mg, 4.5 mmol) were mixed with triethylamine (Fluka, 1.4 mL, 10 mmol) in acetonitrile (50 mL). Tert-buthyl bromoacetate (Fluka, 1.47 mL, 10 mmol) was dissolved in acetonitrile (25 mL) and added dropwise. The reaction mixture was stirred in room temperature overnight. pH was controlled and triethylamine added if necessary. Solvents were removed in vacuo and crude material dissolved in dichloromethane (150 mL) and washed with water (2×25 mL), 0.1 M hydrochloric acid (1×25 mL) and water (1×25 mL). The organic phase was filtered and solvent evaporated off. Crude material was dissolved in acetonitrile/water (1:1) and purified by preparative HPLC (Phenomenex Luna C18 (2) 5 µm 250×21.2 mm, solvents: A=water/0.1% trifluoroacetic acid and B=acetonitrile/ 0.1% trifluoroacetic acid; gradient 10-80% B over 60 min) and lyophilized LC-MS (Phenomenex Luna C18(2) 2.0×50 mm, 3 µm, solvents: A=water/0.1% trifluoroacetic acid and B=acetonitrile/0.1% trifluoroacetic acid; gradient 10-80% B over 5 min; flow rate 0.6 mL/min, UV detection at 214 and 254 nm, ESI-MS) $t_R$=3.99 min, (M1) 447.4. Product verified by NMR.

Product was mixed with Pd/C (10%, 235 mg) and methanol (25 mL) and stiffed under argon. Argon was then removed by vacuo and hydrogen gas was started to be supplied. Reaction mixture was left for three hours with stirring and continuously supply of hydrogen gas. Catalyst was removed by centrifugation and solvents evaporated off. Crude product was purified with preparative HPLC (Phenomenex Luna C18 (2) 5 µm 250×21.2 mm, solvents: A=water/0.1% trifluoroacetic acid and B=acetonitrile/0.1% trifluoroacetic acid; gradient 2-80% B over 60 min) LC-MS (Phenomenex Luna C18(2) 2.0×50 mm, 3 µm, solvents: A=water/0.1% trifluoroacetic acid and B=acetonitrile/0.1% trifluoroacetic acid; gradient 10-80% B over 5 min; flow rate 0.6 mL/min, UV detection at 214 and 254 nm, ESI-MS) $t_R$=2.55 min, (M1) 357.9. Yield 150 mg. Product confirmed by NMR.

(d) Synthesis of (4,7-Bis-tert-butoxycarbonylmethyl-[1,4,7]triazonan-1-yl)-acetic acid [NOTA(bis-tBu)]

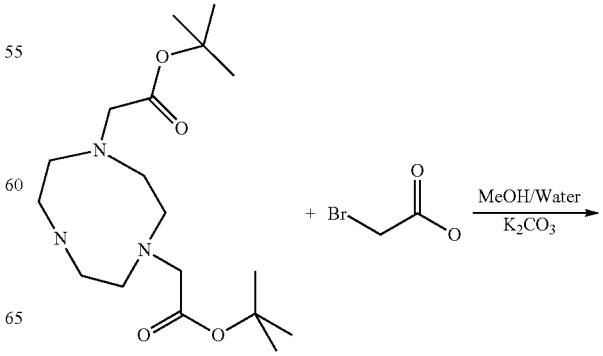

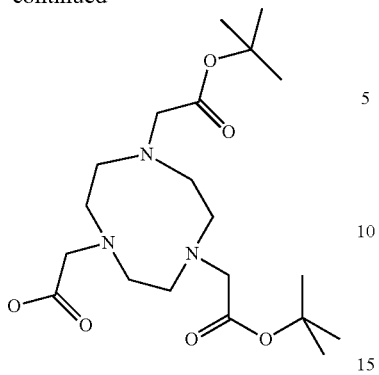

(4-tert-Butoxycarbonylmethyl-[1,4,7]triazonane-1-yl)-acetic acid tert-butyl ester (See Example 17a(i)(d); 280 μmol, 100 mg) and bromoacetic acid (Fluka, 1 mmol, 138.21 mg) were dissolved in methanol (1 mL). Potassium carbonate dissolved in water (1 mL) was added with stirring. Reaction mixture was stirred at room temperature overnight and concentrated in vacuo. The residue was dissolved in water (2.5 mL), and pH was adjusted to 4 with hydrochloric acid (1 M). The crude product was purified by preparative HPLC (Phenomenex Luna C18 (2) 5 μm 250×21.2 mm, solvents: A=water/0.1% trifluoroacetic acid and B=acetonitrile/0.1% trifluoroacetic acid; gradient 10-80% B over 60 min) LC-MS (Phenomenex Luna C18(2) 2.0×50 mm, 3 μm, solvents: A=water/0.1% trifluoroacetic acid and B=acetonitrile/0.1% trifluoroacetic acid; gradient 10-80% B over 5 min; flow rate 0.6 mL/min, UV detection at 214 and 254 nm, ESI-MS) $t_R$=2.40 min. Yield 117.7 mg. Product confirmed by NMR.

NOTA(bis-tBu) was purified by preparative HPLC (gradient: 20-40% B over 40 min) affording 72 mg pure NOTA(bis-tBu). The purified material was characterised by LC-MS (gradient: 10-40% B over 5): $t_R$: 3.75 min. found m/z: 416.2, expected MH$^+$: 416.3.

(ii) Preparation of NOTA(bis-tBu)-maleimide

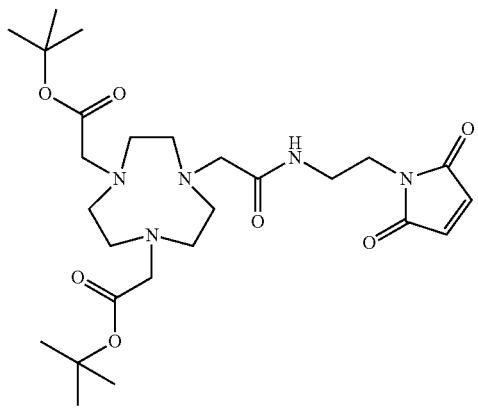 [SMILES: CC(C)(C)OC(=O)CN1CCN(CC(=O)NCCN2C(=O)C=CC2=O)CCN(CC(=O)OC(C)(C)C)CC1]

N-(2-Aminoethyl)maleimide trifluoroacetic acid salt (23 mg, 0.090 mmol), NOTA(bis-tBu) (30 mg, 0.072 mmol) and PyAOP (51 mg, 0.10 mmol) were dissolved in N,N-dimethylformamide (DMF) (2 mL). Sym.-collidine (29 μL, 0.40 mmol) was added and the reaction mixture shaken for 1 hr. The mixture was diluted with water/0.1% trifluoroacetic acid (TFA) (6 mL) and the product purified by semi-preparative HPLC. Purification using semi-preparative HPLC (gradient: 20-50% B over 60 min) afforded 33 mg (87%) pure NOTA (bis-tBu)-maleimide. The purified material was characterised by LC-MS (gradient: 10-40% B over 5, $t_R$: 4.09 min. found m/z: 538.2, expected MH$^+$: 538.3

(iii) Preparation of NOTA(bis-acid)-maleimide

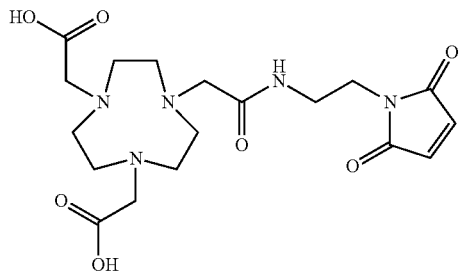 [SMILES: O=C(O)CN1CCN(CC(=O)O)CCN(CC(=O)NCCN2C(=O)C=CC2=O)CC1]

NOTA(bis-tBu)-maleimide (33 mg, 61 μmol) was treated with a solution of 2.5% triisopropylsilane (TIS) and 2.5% water in TFA (10 mL) for 4 hrs 30 min TFA was evaporated in vacuo, the residue dissolved in water/0.1% TFA (8 mL) and the product purified by semi-preparative HPLC. Purification using semi-preparative HPLC (gradient: 0-20% B over 40 min) afforded 15 mg (58%) pure NOTA(bis-acid)-maleimide. The purified material was characterised by LC-MS (gradient: 0-30% B over 5): $t_R$: 1.34 min. found m/z: 426.0, expected MH$^+$: 426.2

(iv) Preparation of 4

Recombinant Z02891-Cys (40 mg, 5.7 μmol) (purchased from Affibody AB, Sweden) and NOTA(bis-acid)-maleimide (6.1 mg, 14 μmol) were dissolved in water (1.5 mL). The solution was adjusted to pH 6 by adding ammonium acetate and the mixture shaken for 1 hr. The reaction mixture was diluted with water/0.1% TFA (6 mL) and the product purified using semi-preparative HPLC. Purification using semi-preparative HPLC (gradient: 20-30% B over 40 min) afforded 38 mg (90%) pure compound 4. Purified 4 was analysed by analytical LC-MS (gradient: 10-40% B over 5 min) $t_R$: 3.31 min. found m/z: 1864.5, expected MH$_4^{4+}$: 1864.5

Example 18

Time Course Study For The Radiosynthesis Of [$^{18}$F] alf-NOTA(COOH)$_3$-Z02891(SEQ ID No. 2)(5a)

Figure 29:
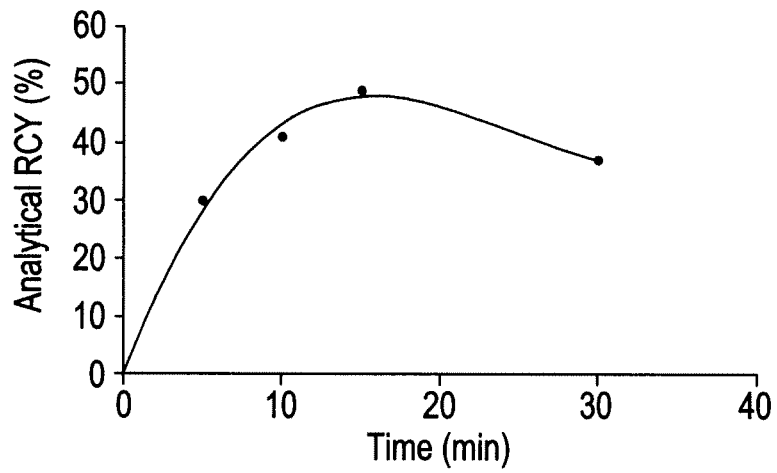
FIG. 29 depicts a time course study of 5 showing labelling efficiencies as measured by analytical radio HPLC.

Fluorine-18 was purified using a QMA cartridge and eluted with saline as described by W. J. McBride et al. (*Bioconj. Chem.* 2010, 21, 1331). A solution of $^{18}$F-water (25 μL, 12 MBq) was mixed with AlCl$_3$ (1.667 μg, 12.5 nmol) in sodium acetate buffer (1.5 μL, pH 4.0, 0.5 M) and compound 6 (380 μg, 50 nmol):

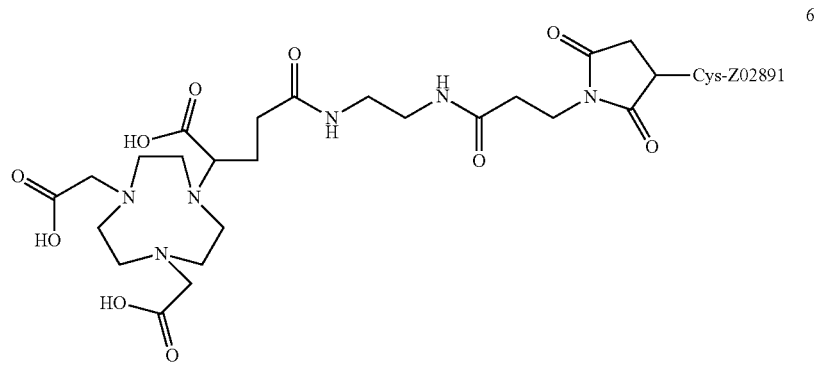

dissolved in sodium acetate buffer (25 μL, pH 4.0, 0.5 M). The mixture was heated at 100° C. and aliquots analysed by HPLC. The analytical data are given in FIG. 29.

Example 18a

Preparation of Compound 6

(i) Preparation of NOTA(tris-tBu)

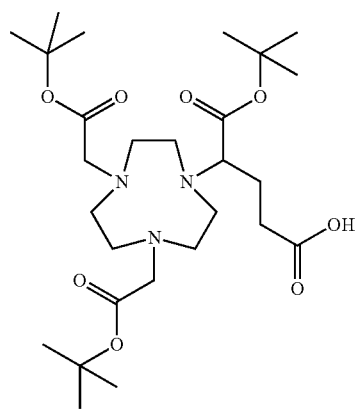 [SMILES: CC(C)(C)OC(=O)CN1CCN(CC(=O)OC(C)(C)C)CCN(C(CCC(=O)O)C(=O)OC(C)(C)C)CC1]

(a) Synthesis of α-bromoglutaric acid 5-benzyl ester

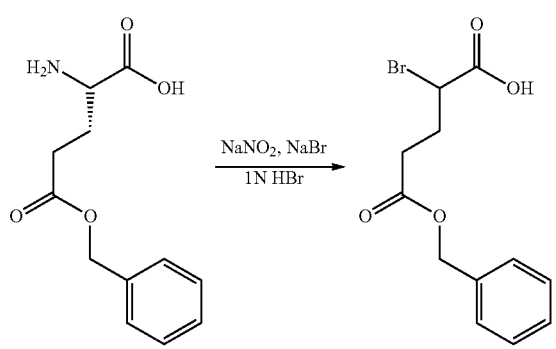

To a solution of L-glutamic acid-5-benzylester (Fluka, 3.0 g, 0.013 mol) and sodium bromide (Fisher, 4.6 g, 0.044 mol) in aqueous hydrobromic acid (Fluka, 1 M, 22.5 mL) cooled to 0° C. was added portion wise sodium nitrite (Fluka, 1.6 g, 0.023 mol). After stirring for 2 h at 0° C., concentrated sulphuric acid (Merck, 1.2 mL) was added followed by diethyl ether (Eternell). The water phase was extracted three times with diethyl ether. The combined organic phases was washed four times with brine, dried over sodium sulphate and evaporated under reduced pressure. The crude product was purified using normal phase chromatography (Silica column (40 g), solvents: A=hexane, B=ethyl acetate, gradient: 10-35% B over 20 min, flow rate 40 mL/min, UV detection at 214 and 254 nm) affording 1.81 g of the pure product. Yield 46%. Structure verified by NMR.

(b) Synthesis of α-bromoglutaric acid 5-benzyl ester 1-tert-butyl ester (*Bioorg. Med. Chem. Lett.* 2000 10, 2133-2135)

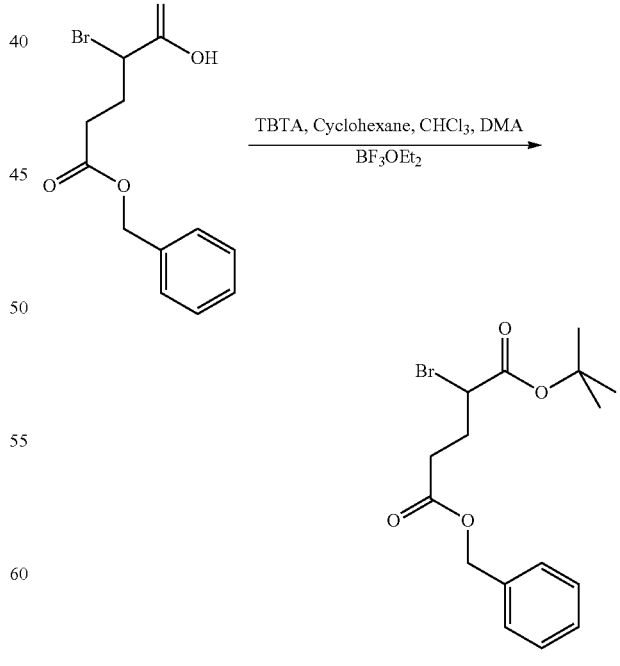

To a solution of α-bromoglutaric acid-5-benzylester (See Example 18a(i)(a); 1.2 g, 4.0 mmol) in chloroform (Merck, 5 mL) a solution of tert-butyl 2,2,2-trichloroacetimidate (Fluka, 1.57 mL, 8.52 mmol) in cyclohexane (Merck, 5 mL) was added dropwise over 5 minutes. N,N-Dimethylacetamide (Fluka, 0.88 mL) was added followed by boron trifluoride ethyl etherate (Aldrich, 80 µL) as catalyst. The reaction mixture was stirred for 5 days at room temperature. Hexane was added and the organic phase washed with brine three times, dried over sodium sulphate and evaporated under reduced pressure. The crude product was purified using normal phase chromatography (Silica column (40 g), solvents: A=hexane, B=ethyl acetate, gradient: 10 to 35% B over 15 min, flow rate 40 mL/min, UV detection at 214 and 254 nm) affording 1.13 g (79%) of the pure product. Structure was verified by NMR trifluoroacetic acid and B=acetonitrile/0.1% trifluoroacetic acid; gradient 10-50% B over 5 min; flow rate 0.6 mL/min, UV detection at 214 and 254 nm, ESI-MS) $t_R$=2.5 min, m/z (MIT), 406.3.

(d) Synthesis of 2-(4,7-bis-tert-butoxycarbonylmethyl-[1,4,7]triazonan-1-yl-pentanedioic acid 5-benzyl ester 1-tert-butyl ester (c) Synthesis of 2-[1,4,7]triazonan-1-yl-pentanedioic acid 5-benzyl ester 1-tert-butyl ester

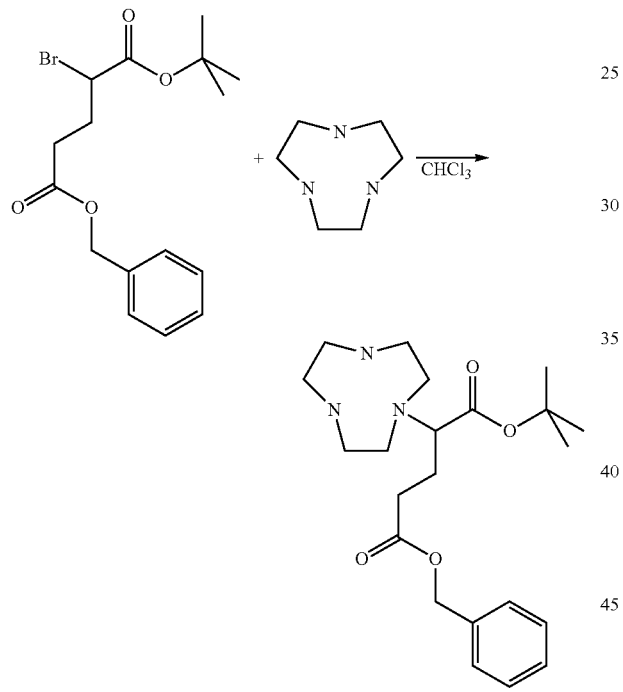

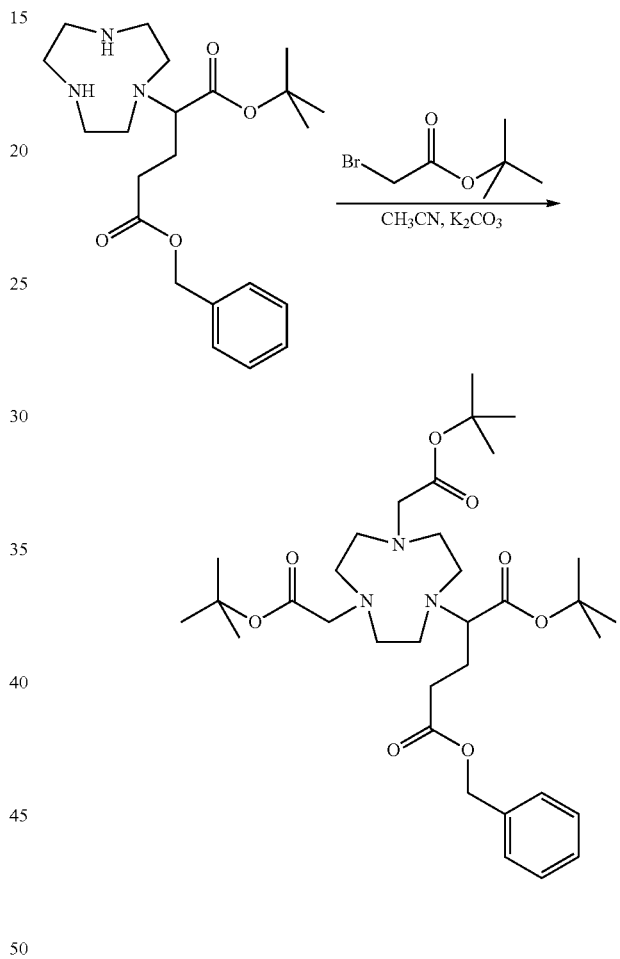

A solution of α-bromoglutaric acid-5-benzylester 1-tert-butyl ester (See Example 18a(i)(a); 513 mg, 1.44 mmol) in chloroform (Merck, 20 mL) was added over a period of 3 hours to a solution of 1,4,7 triazacyclononane (Fluka, 557 mg, 4.31 mmol) in chloroform (Merck, 20 mL). The mixture was stirred for 3 days at room temperature and concentrated in vacuo to a light yellow oil. The crude product was purified using normal phase chromatography (Silica column (40 g), solvents: A=ethanol: ammonia (aq) 95:5, B=chloroform: ethanol: ammonia (aq) 385:175:20, gradient: 0% B over 6 min, 100% B over 12 min, flow rate 40 mL/min, UV detection at 214 and 254 nm) affording the semi-pure product (289 mg). Yield 49%. Product confirmed by LC-MS (column Phenomenex Luna C18(2) 2.0×50 mm, 3 µm, solvents: A=water/0.1%

2-[1,4,7]-Triazonan-1-yl-pentanedioic acid 5-benzyl ester 1-tert-butyl ester (See Example 18a(i)(b); 600 mg, 1.48 mmol) in dry acetonitrile (40 mL) was cooled to zero degrees before tert-butyl bromoacetate (Fluka, 548 mg, 414 µL, 2.81 mmol) in dry acetonitrile (10 mL) was added drop wise over a period of 15 minutes. The reaction mixture was stirred for additional 15 minutes before dry potassium carbonate (Fluka, 1.13 g, 814 mmol) was added and the reaction mixture warmed slowly to room temperature over 4 hours. The mixture was filtered over Celite and evaporated to dryness to afford the crude product. Product was confirmed by LC-MS (column Phenomenex Luna C18(2) 2.0×50 mm, 3 µm, solvents: A=water/0.1% trifluoroacetic acid and B=acetonitrile/ 0.1% trifluoroacetic acid; gradient 10-80% B over 5 min; flow rate 0.6 mL/min, UV detection at 214 and 254 nm, ESI-MS) $t_R$=3.9 min, m/z (MIT), 634.4.

(e) Synthesis of 2-(4,7-bis-tert-butoxycarbonylmethyl-[1,4,7]triazonan-1-yl-pentanedioic acid 1-tert-butyl ester [NOTA(tris-tBu)]

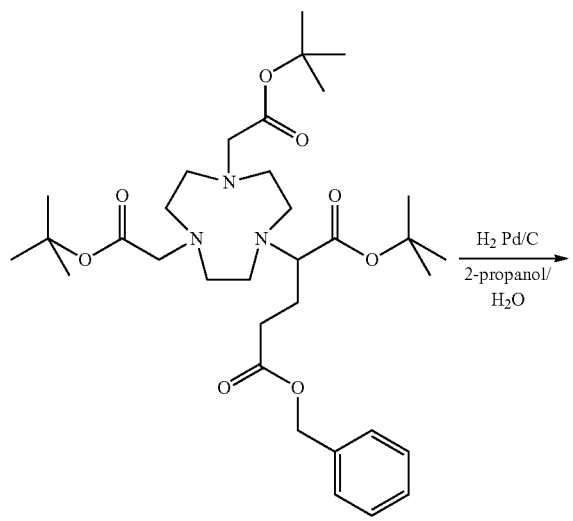

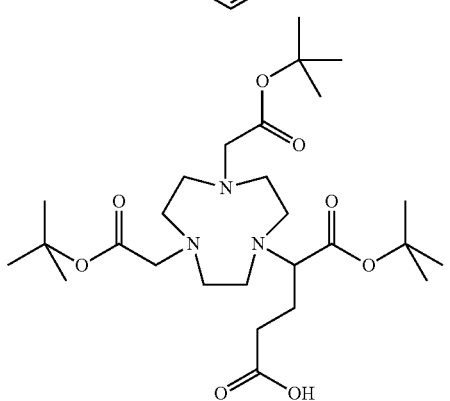

2-(4,7-Bis-tert-butoxycarbonylmethyl-[1,4,7]triazonan-1-yl-pentanedioic acid 5-benzyl ester 1-tert-butyl ester (See Example 18a(i)(c); 938 mg, 1.48 mmol) was dissolved in 2-propanol (Arcus, 115 mL) and 10% Pd/C (Koch-Light, 315 mg) suspended in water (3 mL) was added. The mixture was treated with hydrogen (4 atm) for 3 hours, filtered over Celite and evaporated to dryness. The residue was chromatographed on silica gel (Silica column (4 g), solvents: 2-propanol:ammonia 95:5, flow rate 40 mL/min, UV detection at 214 and 254 nm) affording a semi-pure product (225 mg). Product was confirmed by LCMS (Phenomenex Luna C18 (2), 2.0×50 mm, 3 μm; solvents: A=water/0.1% trifluoroacetic acid and B=acetonitrile/0.1% trifluoroacetic acid, gradient 10-80% B over 5 min, flow rate 0.6 mL/min, UV detection at 214 and 254 nm, ESI-MS) $t_R$ 2.4 min, MH$^+$ 544.5.

Purified NOTA(tris-tBu) was characterised by LC-MS (gradient: 10-80% B over 5): $t_R$: 2.4 min. found m/z: 544.5, expected MH$^+$: 544.4

(ii) Preparation of NOTA(tris-tBu)-NH—CH2CH2-NH2

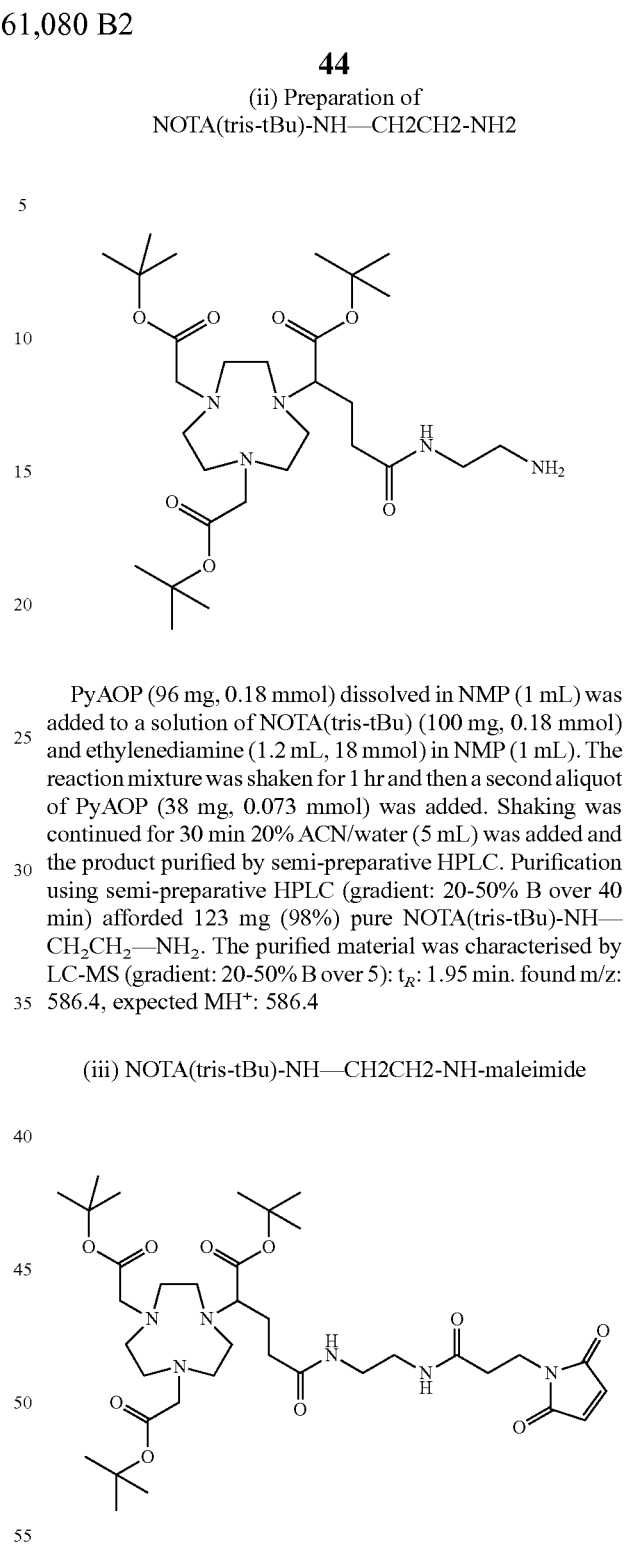

PyAOP (96 mg, 0.18 mmol) dissolved in NMP (1 mL) was added to a solution of NOTA(tris-tBu) (100 mg, 0.18 mmol) and ethylenediamine (1.2 mL, 18 mmol) in NMP (1 mL). The reaction mixture was shaken for 1 hr and then a second aliquot of PyAOP (38 mg, 0.073 mmol) was added. Shaking was continued for 30 min 20% ACN/water (5 mL) was added and the product purified by semi-preparative HPLC. Purification using semi-preparative HPLC (gradient: 20-50% B over 40 min) afforded 123 mg (98%) pure NOTA(tris-tBu)-NH—CH$_2$CH$_2$—NH$_2$. The purified material was characterised by LC-MS (gradient: 20-50% B over 5): $t_R$: 1.95 min. found m/z: 586.4, expected MH$^+$: 586.4

(iii) NOTA(tris-tBu)-NH—CH2CH2-NH-maleimide

NOTA(tris-tBu)-NH—CH$_2$CH$_2$—NH$_2$ (123 mg, 0.176 mmol), 3-maleimido-propionic aid NHS ester (70 mg, 0.26 mmol) and sym.-collidine (346 μL, 2.60 mmol) were dissolved in NMP (2 mL). The reaction mixture was stirred for 6 hr. Water (6 mL) was added and the product purified by semi-preparative HPLC. Purification using semi-preparative HPLC (gradient: 20-50% B over 40 min) afforded 115 mg (87%) pure NOTA(ths-tBu)-NH—CH$_2$CH$_2$—NH-maleimide. The purified material was characterised by LC-MS (gradient: 10-60% B over 5): $t_R$: 3.36 min. found m/z: 737.4, expected MH$^+$: 737.4

(iv) Preparation of NOTA(tris-acid)-NH—CH2CH2-NH-maleimide

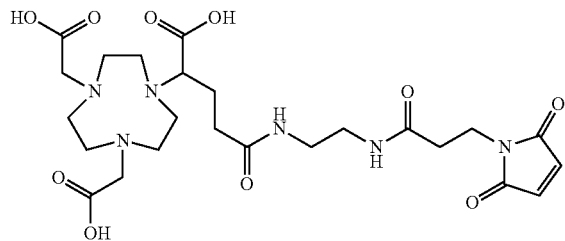 [SMILES: O=C(O)CN1CCN(CC(=O)O)CCN(C(CCC(=O)NCCNC(=O)CCN2C(=O)C=CC2=O)C(=O)O)CC1]

NOTA(tris-tBu)-NH—CH$_2$CH$_2$—NH-maleimide (115 mg, 0.150 mmol) was treated with a solution of 2.5% TIS and 2.5% water in TFA (10 mL) for 4 hrs. The solvents were evaporated in vacuo, the residue re-dissolved in water (8 mL) and the product purified by semi-preparative HPLC. Purification using semi-preparative HPLC (gradient: 0-20% B over 40 min) afforded 80 mg (90%) pure NOTA(tris-acid)-NH—CH$_2$CH$_2$—NH-maleimide. The purified material was characterised by LC-MS (gradient: 0-30% B over 5): $t_R$: 2.74 min. found m/z: 569.5, expected MH$^{30}$: 569.2

(v) Preparation of Compound 6

(a) Preparation of Synthetic Z02891-Cys

Sequence:
EAKYAKEMRNAYWEIALLPNLT-NQQKRAFIRKLYDDPSQSSELLSEAKKLND SQAP-KVDC was assembled on a CEM Liberty microwave peptide synthesiser using Fmoc chemistry starting with 0.05 mmol NovaPEG Rink Amide resin. 0.5 mmol amino acid was applied in each coupling step (5 min at 75° C.) using 0.45 mmol HBTU/0.45 mmol HOAt/1.0 mmol DIPEA for in situ activation. Fmoc was removed by 5% piperazine in DMF. Double coupling of both Arg was applied. Asp-Ser and Leu-Ser pseudoproline dipeptides (0.5 mmol) were incorporated into the sequence.

The simultaneous removal of the side-chain protecting groups and cleavage of the peptide from the resin was carried out in TFA (40 mL) containing 2.5% TIS, 2.5% EDT, 2.5% EMS and 2.5% water for 1 hr. The resin was removed by filtration, washed with TFA and the combined filtrates were evaporated in vacuo. Diethyl ether was added to the residue, the formed precipitate washed with diethyl ether and dried. The cleavage procedure was repeated once more. The dried precipitates were dissolved in 20% ACN/water and left over night in order to remove remaining Trp protecting groups. The solution was lyophilised affording 148 mg (42%) crude Z02891-Cys. 148 mg crude Z02891-Cys was purified by semi-preparative HPLC (4 runs, gradient: 25-30% B over 40 min) affording 33 mg (9%) pure Z02891-Cys. The purified material was characterised by LC-MS (gradient: 10-40% B over 5): $t_R$: 3.40 min. found m/z: 1758.3, expected MH$_4^{4+}$: 1758.4.

Synthetic Z02891-Cys (13.7 mg, 1.95 µmol) and NOTA(tris-acid)-NH—CH2CH2-NH-maleimide (11 mg, 19.3 µmol) were dissolved in water (1 mL). The solution was adjusted to pH 6 by adding ammonium acetate and the mixture shaken for 3 hrs. The reaction mixture was diluted with water/0.1% TFA (6.5 mL) and the product was purified using semi-preparative HPLC. Purification using semi-preparative HPLC (gradient: 15-35% B over 40 min) afforded 8.4 mg (57%) pure 6. Compound 6 was analysed by analytical LC-MS (gradient: 10-40% B over 5 min) tR: 3.31 min. found m/z: 1900.7, expected MH44+: 1900.2

Example 19

Impact of the AlCl3/Peptide Ratio Radiochemical Yields of [18F]AlF-NOTA(COOH)$_2$-Z02891(SEQ ID No. 2)(5)

Three solutions of 4 (149 µg, 20 nmol) in sodium acetate buffer (10 µL, pH 4.0, 0.5 M) were mixed with solutions of AlCl$_3$ (0.33 µg, 2.49 nmol; 0.66 µg, 4.98 nmol; and 1.33 µg, 9.96 nmol, respectively) in sodium acetate buffer (1 µL, pH 4.0, 0.5 M) in conical polypropylene centrifuge vials (1.5 mL). To these vials a small volume of [$^{18}$F]fluoride (10 µL) was added. The vials were heated for 15 min at 100° C. and subsequently analyzed by HPLC. The incorporation yields are given in Table 12.

TABLE 12

Impact of AlCl$_3$/peptide ratio on analytical RCY of [$^{18}$F]AlF-NOTA(COOH)$_2$-Z02891(SEQ ID No. 2)(5).

| Experiment | AlCl$_3$/peptide | Product (5) | Pre-peak |
|---|---|---|---|
| 1 | 1/8 | 23% | 2% |
| 2 | 1/4 | 29% | 2% |
| 3 | 1/2 | 28% | 3% |

Example 20

Impact of the Reagent Dilution on Radiochemical Yields of [18F]AlF-NOTA(COOH)$_2$-Z02891(SEQ ID No. 2)(5)

A solution of 4 (373 µg, 50 nmol) in sodium acetate buffer (25 µL, pH 4.0, 0.5 M) was mixed with a solution of AlCl$_3$ (1.66 µg, 12.5 nmol) in sodium acetate buffer (1.5 µL, pH 4.0, 0.5 M) in a conical polypropylene centrifuge vial (1.5 mL). A small volume of [$^{18}$F]fluoride (10 µL, 80 MBq) was added. Two serial dilutions of this mixture (50% and 25% v/v) with sodium acetate buffer (1.5 µL, pH 4.0, 0.5 M) were prepared. The three vials were then heated at 100° C. for 15 minutes and subsequently analyzed by HPLC. The data are shown in Table 13.

TABLE 13

Impact of reagent concentration on analytical RCY of [$^{18}$F]AlF-NOTA(COOH)$_2$-Z02891(SEQ ID No. 2)(5). The ratio of reagents was kept constant.

| Experiment | Peptide concentration (µg/µL) | Product (5) | Pre-peak |
|---|---|---|---|
| 1 | 7 | 30% | 5% |
| 2 | 3.5 | 16% | 3% |
| 3 | 1.75 | 8% | 1% |

Example 21

Impact of the Peptide/AlCl3 Concentration on Radiochemical Yields of [18F]AlF-NOTA(COOH)$_2$-Z02891(SEQ ID No. 2)(5)

Figure 30:
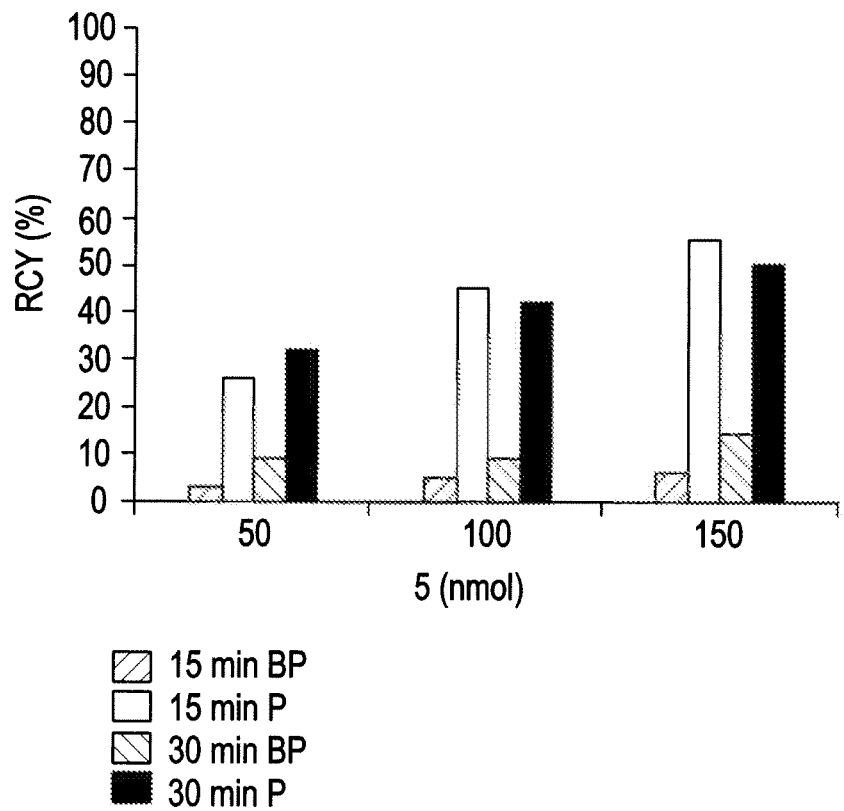
FIG. 30 is an analytical RCY of 5 after increasing the peptide/AlCl$_3$ concentration (P: product, BP: by-product, see FIG. 28).

Three vials containing [$^{18}$F]fluoride (25 µL, 23-25 MBq), AlCl$_3$ (¼ eq. of peptide 4 in 1.5 µL sodium acetate buffer, pH 4.0, 0.5 M), and 4 (50, 100, 150 nmol) in sodium acetate buffer (25 µL, pH 4.0, 0.5 M) were heated at 100° C. for 30 minutes. FIG. 30 shows the incorporation data after 15 and 30 minutes.

Example 22

Impact of Microwave Heating on Radiochemical Yields of [$^{18}$F]AlF-NOTA(COOH)$_2$-Z02891(SEQ ID No. 2)(5)

A Wheaton vial (3 mL) containing [$^{18}$F]fluoride (25 μL, 29 MBq), AlCl$_3$ (1.66 μg, 12.5 nmol) in 1.5 μL sodium acetate buffer, pH 4.0, 0.5 M), and 4 (373 μg, 50 nmol) in sodium acetate buffer (25 μL, pH 4.0, 0.5 M) was heated using a microwave device (Resonance Instruments Model 521, set temperature 80° C., 50 W) for 5, 10, and 15 s. Table 14 gives the summary of the HPLC analyses after these time points.

TABLE 14

Analytical RCY from preparation of [$^{18}$F]AlF-NOTA(COOH)$_2$-Z02891(SEQ ID No. 2)(5) using microwave heating.

| Time (s) | Product (5) | Pre-peak |
|---|---|---|
| 5 | 17% | — |
| 10 | 21% | — |
| 15 | 35% | 1% |

Example 23

Preparation of [18F]AlF-NOTA(COOH)$_3$-Z02891(SEQ ID No. 2)(5a)

A PP centrifuge vial (1.5 mL) containing [$^{18}$F]fluoride (25 μL, 29 MBq), AlCl$_3$ (1.66 μg, 12.5 nmol) in 1.5 μL sodium acetate buffer, pH 4.0, 0.5 M), and 6 (380 μg, 50 nmol) in sodium acetate buffer (25 μL, pH 4.0, 0.5 M) was heated at 100° C. for 15 minutes. The analytical RCY of 5a was 15-20%. FIG. 31 shows the HPLC profile of the reaction mixture.

Example 24

Preparation of [18F]SiFA-Z02891(SEQ ID No. 2)(7)

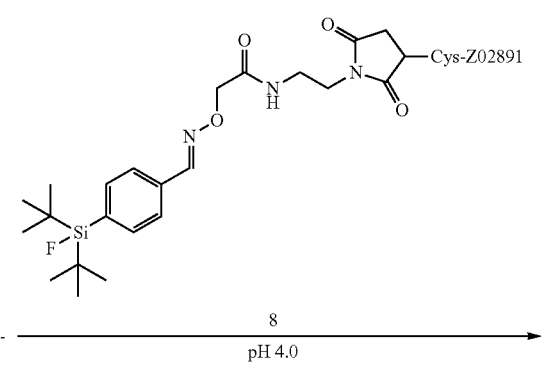

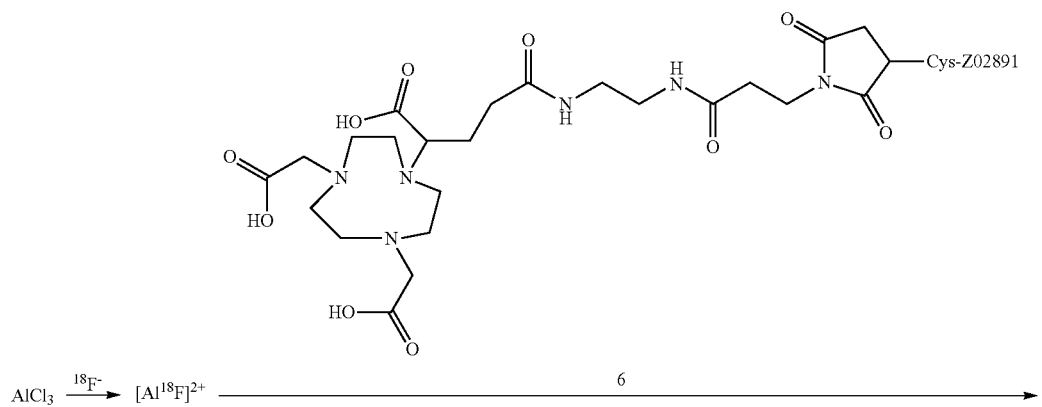

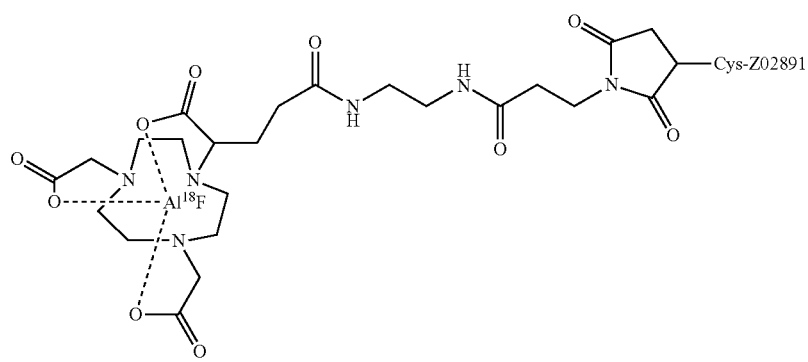

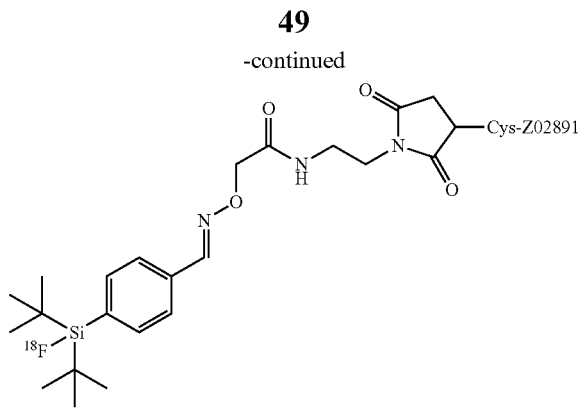

7

Figure 32:
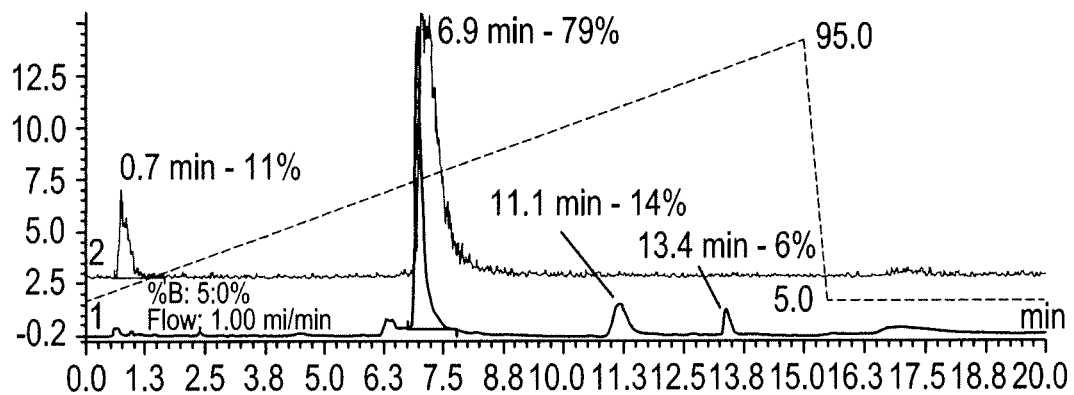
FIG. 32 is an analytical radioactivity channel HPLC of isolated 7 (Red: radioactivity channel, blue: UV channel at 280 nm).

A solution of peptide precursor 8 (750 μg, 100 nmol) in sodium acetate buffer (50 μL, pH 4.0, 0.5 M) was added to a solution of [$^{18}$F]fluoride in water (50 μL) in a polypropylene centrifuge vial (1.5 mL) and heated for 15 minutes at 95° C. After adding saline (100 μL, 0.9% w/v), the mixture was purified using a saline conditioned NAP5 column (GE Healthcare). The product 7 was obtained with 18% non-decay corrected radiochemical yield and 87% radiochemical purity after 26 minutes. FIG. 32 shows the HPLC analysis of the final product.

Example 24a

Preparation of Compound 8

(i) Synthesis of SiFa

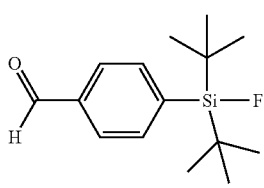 [SMILES: CC(C)(C)[Si](F)(c1ccc(C=O)cc1)C(C)(C)C]

n-Butyllithium in hexane (2.5 M, 3.2 mL, 7.9 mmol) was added dropwise under argon to a cooled (−78° C.) solution of 2-(4-bromophenyl)-1,3-dioxolane (1.8 g, 7.9 mmol) in dry tetrahydrofurna (THF) (6 mL). After stirring for 2 hrs at 78° C., the resulting yellow suspension was taken up in a syringe and added dropwise over a period of 20 min to a cooled solution (−70° C.) of di-tert-butyldifluorosilane (1.5 mL, 8.33 mmol) in THF (15 mL). The reaction mixture was stiffed for 1 hr at 70° C. and then allowed to warm to ambient temperature. A sample (3 mL) was withdrawn from the reaction mixture after 2 hrs 30 min and quenched with water/0.1% TFA resulting in removal of the dioxolane protecting group. The deprotected product was purified by preparative HPLC. Purification using preparative HPLC (gradient: 40-95% B over 60 min) afforded pure SiFA. The purified material was characterised by LC-MS (gradient: 50-95% B over 5): $t_R$: 2.05 min. found m/z: not detected, expected MH$^+$: 267.2

(ii) Preparation of SiFA-aminooxyacetyl-maleimide

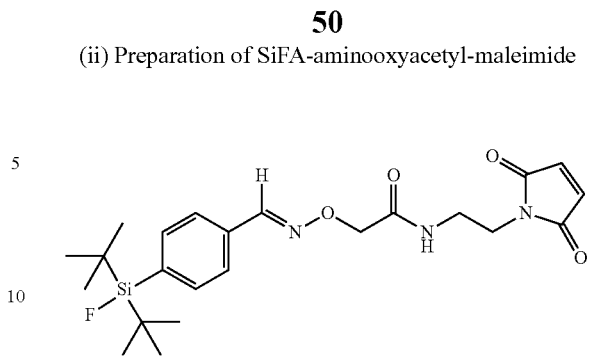

Eei-aminooxyacetyl-maleimide (20 mg, 71 μmol) was added to SiFA in water/ACN/0.1% TFA (from HPLC prep fractions). 1M HCl (1 mL) was added and the reaction mixture stirred over night. The product was purified by semi-preparative HPLC. Purification using semi-preparative HPLC (gradient: 40-80% B over 40 min) afforded 15 mg (45%) pure SiFA-aminooxyacetyl-maleimide. The purified material was characterised by LC-MS (gradient: 40-70% B over 5): $t_R$: 3.00 min. found m/z: 462.1, expected MH$^+$: 462.2

(iii) Preparation of Compound 8

Recombinant Z02891-Cys Affibody (24 mg, 3.4 μmol) and SiFA-aminooxyacetyl-maleimide (4.7 mg, 10 μmol) were dissolved in 50% ACN/water (1 mL). The solution was adjusted to pH 6 by adding ammonium acetate and the mixture shaken for 1 hr. The reaction mixture was diluted with 10% ACN/water/0.1% TFA (8 mL) and the product purified using semi-preparative HPLC. Purification using semi-preparative HPLC (gradient: 20-40% B over 40 min) afforded 26 mg (100%) pure Z02891-Cys-maleimide-aminooxyacetyl-SiFA (8). Purified Z02891-Cys-maleimide-aminooxyacetyl-SiFA (8) was analysed by analytical LC-MS (gradient: 10-40% B over 5 min) $t_R$: 3.87 min. found m/z: 1873.6, expected MH$_4^{4+}$: 1873.5

Example 25

Tumour Model Validation

The A431 and NCI-N87 xenograft models were validated for tumour growth and HER2 expression. The animal model setup involved inoculation of 2×10$^6$ NCI-N87 or 10$^7$ A431 cells per animal (in 100 μl of 50% PBS/50% Matrigel) subcutaneously into the right flank followed by an inoculation period of 30 days. HER2 expression in these tumours was assessed by immunohistochemistry, using the FDA-validated HercepTest (Dako, K5204).

Figure 33:
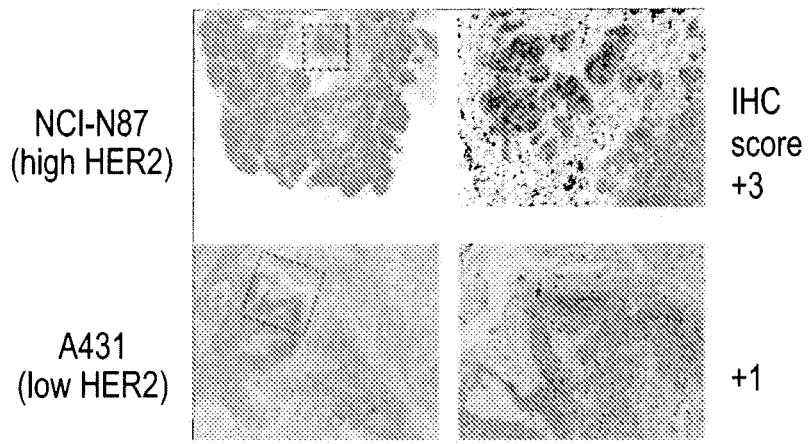
FIG. 33 depicts HER2 protein expression in tumour sections from the NCI-N87 and A431 xenograft models by immunohistochemistry the HERCEPTEST by DAKO. Pictures on the left are ×2 magnification, pictures on the right are ×10 of the highlighted square.

FIG. 33 depicts that with the recommended intensity scale (0→+3), NCI-N87 tumours stain strongly (+3), while A431 cells show a considerably weaker staining intensity (+1). These data suggest that the tumour models have significantly different HER2 expression and are therefore suitable for comparing the uptake of the HER2 targeted Affibody molecules. Based on the adequate separation of IHC scores, no further quantitative assessment was considered necessary.

Example 26

Biodistribution of Compounds 2, 5, and 7 in Normal Mice

Figure 34:
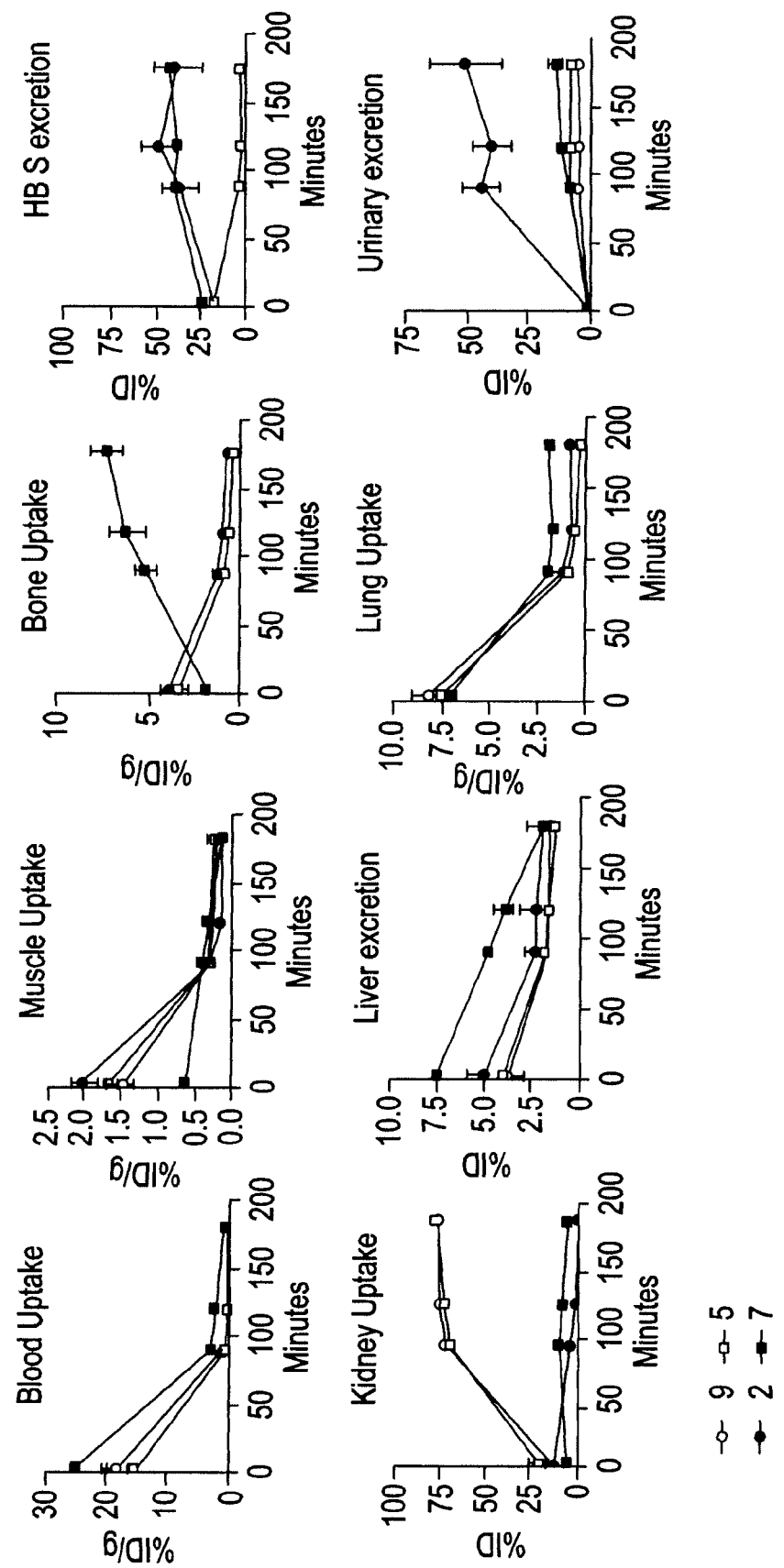
FIG. 34 shows naïve mice biodistributions of 9, 2, 5, and 7.

The saline formulated tracers compounds 2, 5, and 7 have been evaluated using naïve CD1 mice. Following intravenous injection of 3 MBq of activity (2.5 MBq for the 2 min time point), animals were sacrificed at 2, 90, 120 and 180 min post injection and retention of radioactivity was assessed in key organs. In the biodistribution measurements, 5 showed significant kidney retention (70.3% ID at 90 minutes p.i.) which was not observed for the 2 or 7 (4.8% ID and 10% ID, respectively at 90 min p.i.). Defluorination of 7 was observed (bone uptake 5.3% ID/g at 90 min p.i.) FIG. 34 compares the biodistribution data with the corresponding rill [$^{111}$In]DOTA-Z02891(SEQ ID No. 2)(9) compound:

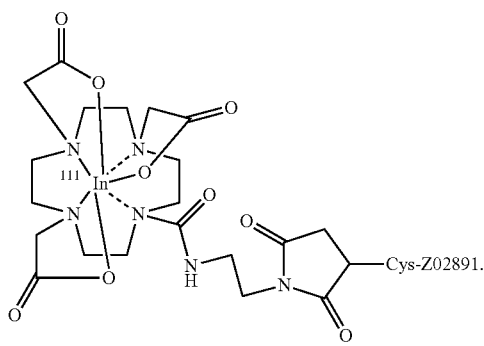

Example 27

Tumour Uptake of Compounds 2, 5, and 7

Figure 35:
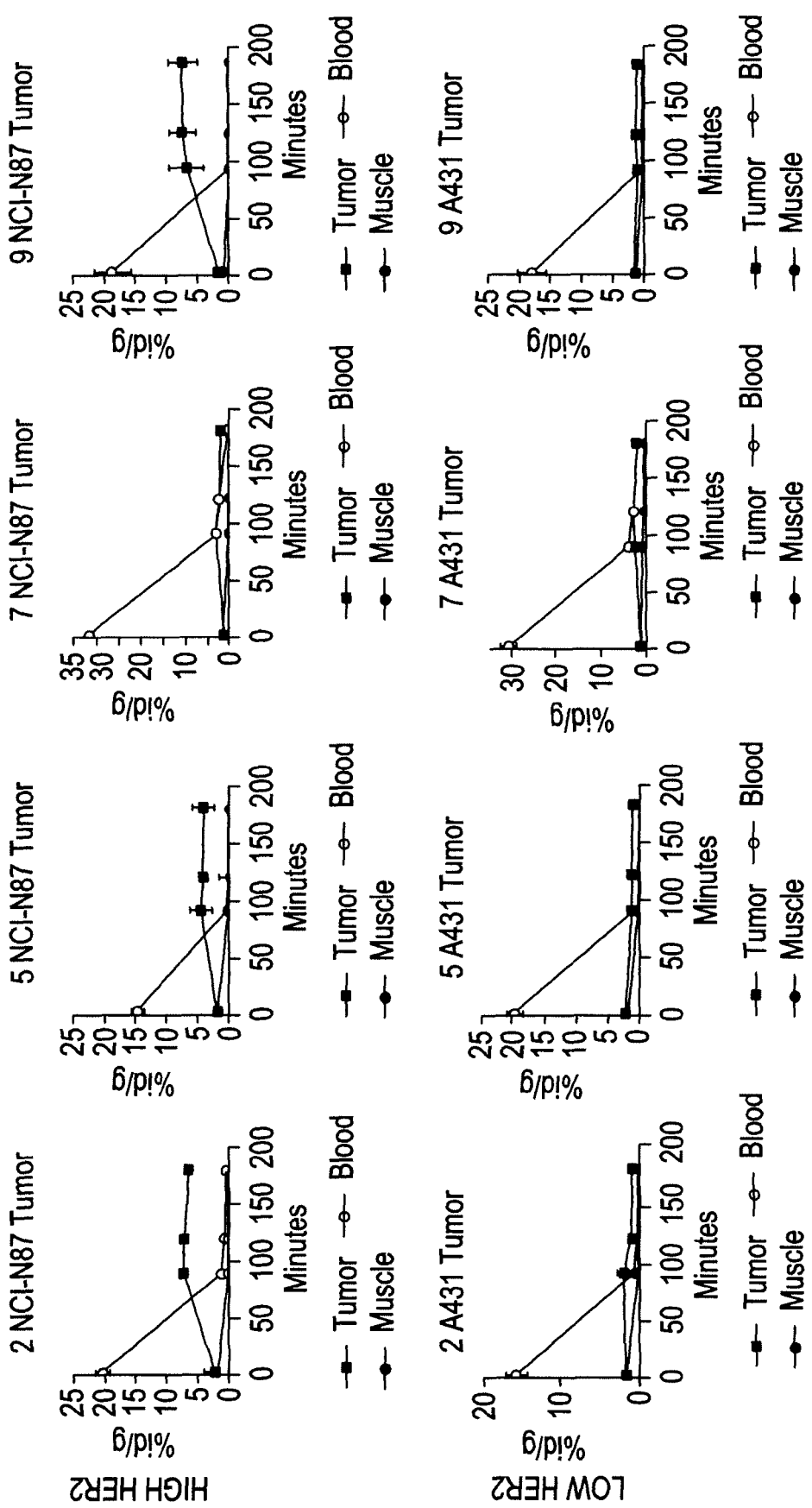
FIG. 35 shows biodistributions of 9, 2, 5, and 7 in the NC87/A431 tumour bearing mice.

In a tumour mouse model with high and low HER2 level expressing tumor cells (NC87 and A431, respectively) a differential uptake of compounds 2, 5, and 7 was observed as expected. FIG. 35, Tables 15 and 16 compare the biodistribution data with corresponding [$^{111}$In]DOTA-Z02891(SEQ ID No. 2)(9) compound.

TABLE 15

Key ratios from the NCI-N87 xenograft biodistribution of Compounds 9, 2, 5 and 7.

| | | Time post injection | | | |
|---|---|---|---|---|---|
| Ratio | Compound | 2 | 90 | 120 | 180 |
| Tumour:Blood | 9 | 0.11 | 14.05 | 19.05 | 75.24 |
| | 2 | 0.11 | 6.05 | 12.62 | 12.87 |
| | 5 | 0.14 | 8.07 | 19.58 | 28.84 |
| | 7 | 0.04 | 1 | 1.05 | 2.62 |
| Tumour:Muscle | 9 | 1.61 | 29.5 | 36.48 | 52.63 |
| | 2 | 1.31 | 28.38 | 46.68 | 30.38 |
| | 5 | 1.21 | 20.91 | 24.11 | 24.99 |
| | 7 | 1.54 | 7.49 | 6.2 | 10.6 |
| Tumour:Liver | 9 | 0.43 | 5.6 | 4.99 | 6.16 |
| | 2 | 0.35 | 2.45 | 1.30 | 1.96 |
| | 5 | 0.1 | 0.31 | 0.40 | 0.40 |
| | 7 | 0.13 | 0.43 | 0.49 | 0.78 |

TABLE 16

Key ratios from A431 xenograft biodistribution of Compounds 9, 2, 5 and 7.

| | | Time post injection | | | |
|---|---|---|---|---|---|
| Ratio | Compound | 2 | 90 | 120 | 180 |
| Tumour:blood | 9 | 0.06 | 3.13 | 4.16 | 11.47 |
| | 2 | 0.1 | 3.09 | 2.85 | 4.89 |
| | 5 | 0.12 | 3.13 | 5.16 | 11.32 |
| | 7 | 0.03 | 0.58 | 0.95 | 1.63 |
| Tumour:muscle | 9 | 0.65 | 4.48 | 5.41 | 6.55 |
| | 2 | 1.02 | 8.88 | 8.44 | 8.78 |
| | 5 | 1.26 | 5.2 | 5.2 | 7.76 |
| | 7 | 0.91 | 2.86 | 4.3 | 5.34 |
| Tumour:liver | 9 | 0.2 | 0.67 | 0.86 | 0.75 |
| | 2 | 0.29 | 0.54 | 0.44 | 1.01 |
| | 5 | 0.4 | 1 | 0.83 | 1.08 |
| | 7 | 0.08 | 0.26 | 0.4 | 0.6 |

Example 28

Imaging of 2 in Dual Tumour Xenograft Model

Dual tumour xenograft mice were generated by implantation of A431 and NCI-N87 in each of the two flanks. These mice were used to assess the biodistribution of 2, enabling a same-animal assessment of uptake in both low and high HER2 expressing tumours. Timepoints included 30 and 60 p.i.

Figure 36:
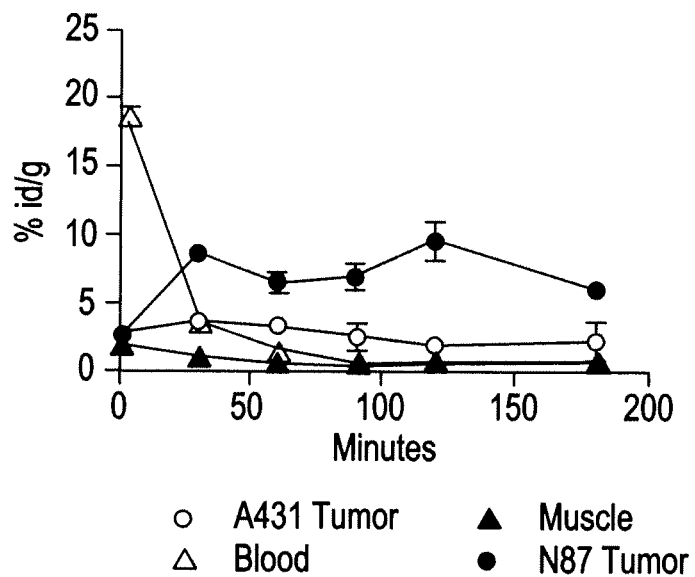
FIG. 36 shows biodistribution profile of 2 in the dual tumour xenograft model.

FIG. 36 shows that 2 performance was comparable to that observed in the single tumour animal studies, with good separation in binder uptake between the A431 and NCI-N87 tumours, starting from as early as 30 min p.i. As far as background tissue clearance (see Table 7 for key tissue ratios), blood levels at 60 min p.i. have reduced significantly, providing a NCI-N87 tumour: blood ratio of 4.52, while at 30 min, partial blood clearance gives a 2.39 ratio, accompanied by a positive tumour:liver ratio of 1.39. These properties suggest that the pharmacokinetics of 2 is sufficient for imaging human subjects within a suitable imaging window.

TABLE 17

Key ratios from the dual tumour xenograft biodistribution of 2.

| | | Time post injection | | | | | |
|---|---|---|---|---|---|---|---|
| Ratio | Tumour | 2 | 30 | 60 | 90 | 120 | 180 |
| Tumour: blood | A431 | 0.14 | 0.96 | 2.11 | 3.51 | 2.90 | 5.05 |
| | N87 | 0.14 | 2.39 | 4.52 | 9.85 | 15.41 | 14.79 |
| Tumour: muscle | A431 | 1.48 | 3.57 | 6.57 | 7.58 | 7.30 | 10.04 |
| | N87 | 1.40 | 8.89 | 14.06 | 21.29 | 38.77 | 29.41 |
| Tumour: liver | A431 | 0.47 | 0.56 | 0.73 | 0.96 | 0.62 | 1.67 |
| | N87 | 0.45 | 1.39 | 1.56 | 2.70 | 3.28 | 4.89 |

Example 29

Compound 2 Add-Back Studies in NCI-N87 Tumoured Mice

Figure 37:
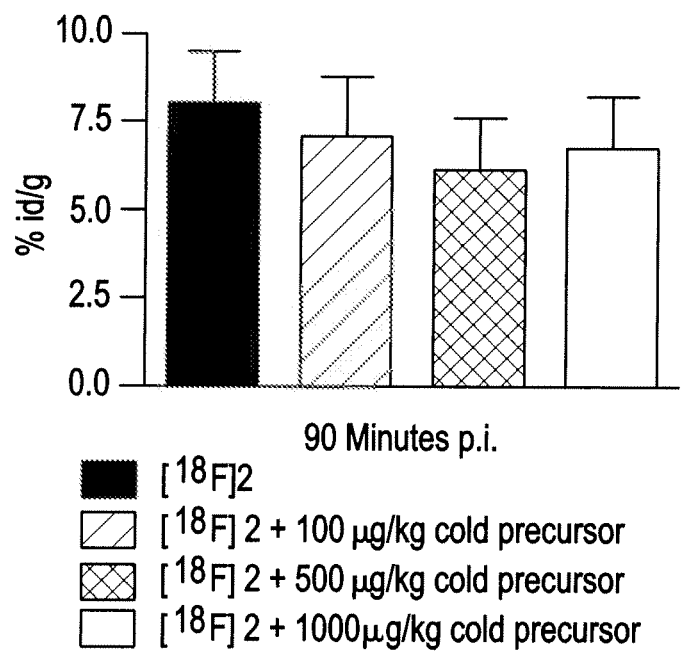
FIG. 37 shows NCI-N87 xenograft biodistribution profile of 2 using increasing concentrations of cold precursor.

For the add-back studies performed in the NCI-N87 tumour model to assess the effect of excess cold ligand in binder efficacy, the following four different preparations were assessed at 90 min p.i.:
1. Standard compound 2 preparation
2. Standard preparation plus 100 μg/kg per mouse cold precursor 3. Standard preparation plus 500 μg/kg per mouse cold precursor
4. Standard preparation plus 1000 μg/kg per mouse cold precursor The concentration of cold precursor in the standard preparation was 120 μg/kg per mouse, therefore this study examined the effects of cold precursor at 10× the original concentration used (in the mouse). FIG. 37 shows that the effect on tumour uptake was not significant and clearance from other tissues was not significantly affected either.

Example 30

Compound 2 In Vivo Imaging Studies in Dual Flank A431/NCI-N87 Tumoured Mice

The dual-tumour mouse model described in Example 28 was used to perform a preliminary imaging study. 10 MBq of 2 were injected i.v. per animal and the mice were imaged for 30 minutes starting at 120 min p.i. The image in FIG. 38 shows that clearance was through the kidneys and bladder, as previously demonstrated through the biodistribution studies. The transverse imaging shows uptake in the 2 tumours, with the NCI-N87 tumour showing considerably higher signal intensity than the A431 tumour, in agreement with the dual tumour biodistribution studies in Example 28.

Comparison of the current 2 imaging study with the Affibody® 9 imaging study (FIG. 38) shows a similar difference in uptake between high and low HER2 expressing tumours. However, 2 has a considerably improved background from the kidneys due to minimal kidney retention also seen in the biodistributions.

All patents, journal articles, publications and other documents discussed and/or cited above are hereby incorporated by reference.

What is claimed is:

1. An imaging agent composition comprising an isolated polypeptide comprising SEQ ID No 1 or SEQ ID No 2, conjugated with an $Al^{18}F$-NOTA-chelator to form an $Al^{18}F$-NOTA-chelator conjugated polypeptide wherein the isolated $Al^{18}F$-NOTA-chelator conjugated polypeptide binds specifically to HER2 or variants thereof.

2. A method of making an imaging agent composition according to claim 1 comprising (i) providing an isolated polypeptide comprising SEQ ID No 1 or SEQ ID No 2; (ii) reacting the polypeptide with a NOTA-chelator to form a NOTA-chelator conjugated polypeptide; and (iii) reacting the NOTA-chelator conjugated polypeptide with an $Al^{18}F$ moiety to form a $Al^{18}F$-NOTA-chelator conjugated polypeptide.

3. A method according to claim 2, wherein said NOTA-chelator comprises a NOTA chelate moiety and a linker.

4. A method of making an imaging agent composition according to claim 1 comprising (i) providing the isolated polypeptide comprising SEQ ID No 1 or SEQ ID No 2; (ii) reacting the polypeptide with a NOTA-chelator, wherein the NOTA-chelator comprises a NOTA chelate moiety and a linker, to form a NOTA-chelator conjugated polypeptide; and (iii) reacting the NOTA-chelator conjugated polypeptide with an $^{18}F$ moiety or a source of $^{18}F$.

5. A pharmaceutical composition comprising an imaging agent composition according to claim 1 and a pharmaceutically acceptable carrier.

* * * * *

```
                        SEQUENCE LISTING

<160> NUMBER OF SEQ ID NOS: 7

<210> SEQ ID NO 1
<211> LENGTH: 58
<212> TYPE: PRT
<213> ORGANISM: Artificial Sequence
<220> FEATURE:
<223> OTHER INFORMATION: SYNTHETIC POLYPEPTIDE

<400> SEQUENCE: 1

Val Glu Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 61
<212> TYPE: PRT
<213> ORGANISM: Artificial Sequence
<220> FEATURE:
<223> OTHER INFORMATION: SYNTHETIC POLYPEPTIDE

<400> SEQUENCE: 2

Ala Glu Ala Lys Tyr Ala Lys Glu Met Arg Asn Ala Tyr Trp Glu Ile
1               5                   10                  15

Ala Leu Leu Pro Asn Leu Thr Asn Gln Gln Lys Arg Ala Phe Ile Arg
            20                  25                  30

Lys Leu Tyr Asp Asp Pro Ser Gln Ser Ser Glu Leu Leu Ser Glu Ala
        35                  40                  45

Lys Lys Leu Asn Asp Ser Gln Ala Pro Lys Val Asp Cys
    50                  55                  60

<210> SEQ ID NO 3
<211> LENGTH: 61
<212> TYPE: PRT
<213> ORGANISM: Artificial Sequence
<220> FEATURE:
<223> OTHER INFORMATION: SYNTHETIC POLYPEPTIDE

<400> SEQUENCE: 3
```

```
Val Asp Asn Lys Phe Asn Lys Glu Met Arg Asn Ala Tyr Trp Glu Ile
1               5                   10                  15

Ala Leu Leu Pro Asn Leu Asn Val Ala Gln Lys Arg Ala Phe Ile Arg
            20                  25                  30

Ser Leu Tyr Asp Asp Pro Ser Gln Ser Ala Asn Leu Leu Ala Glu Ala
                35                  40                  45

Lys Lys Leu Asn Asp Ala Gln Ala Pro Lys Val Asp Cys
50                  55                  60
```

<210> SEQ ID NO 4
<211> LENGTH: 72
<212> TYPE: PRT
<213> ORGANISM: Artificial Sequence
<220> FEATURE:
<223> OTHER INFORMATION: SYNTHETIC POLYPEPTIDE

<400> SEQUENCE: 4

```
Gly Ser Ser His His His His His Leu Gln Val Asp Asn Lys Phe
1               5                   10                  15

Asn Lys Glu Met Arg Asn Ala Tyr Trp Glu Ile Ala Leu Leu Pro Asn
            20                  25                  30

Leu Asn Val Ala Gln Lys Arg Ala Phe Ile Arg Ser Leu Tyr Asp Asp
                35                  40                  45

Pro Ser Gln Ser Ala Asn Leu Leu Ala Glu Ala Lys Lys Leu Asn Asp
50                  55                  60

Ala Gln Ala Pro Lys Val Asp Cys
65                  70
```

<210> SEQ ID NO 5
<211> LENGTH: 130
<212> TYPE: PRT
<213> ORGANISM: Artificial Sequence
<220> FEATURE:
<223> OTHER INFORMATION: SYNTHETIC POLYPEPTIDE

<400> SEQUENCE: 5

```
Gly Ser Ser His His His His His Leu Gln Val Asp Asn Lys Phe
1               5                   10                  15

Asn Lys Glu Met Arg Asn Ala Tyr Trp Glu Ile Ala Leu Leu Pro Asn
            20                  25                  30

Leu Asn Val Ala Gln Lys Arg Ala Phe Ile Arg Ser Leu Tyr Asp Asp
                35                  40                  45

Pro Ser Gln Ser Ala Asn Leu Leu Ala Glu Ala Lys Lys Leu Asn Asp
50                  55                  60

Ala Gln Ala Pro Lys Val Asp Asn Lys Phe Asn Lys Glu Met Arg Asn
65                  70                  75                  80

Ala Tyr Trp Glu Ile Ala Leu Leu Pro Asn Leu Asn Val Ala Gln Lys
                85                  90                  95

Arg Ala Phe Ile Arg Ser Leu Tyr Asp Asp Pro Ser Gln Ser Ala Asn
            100                 105                 110

Leu Leu Ala Glu Ala Lys Lys Leu Asn Asp Ala Gln Ala Pro Lys Val
        115                 120                 125

Asp Cys
    130
```

<210> SEQ ID NO 6
<211> LENGTH: 4
<212> TYPE: PRT
<213> ORGANISM: Artificial Sequence

```
<220> FEATURE:
<223> OTHER INFORMATION: SYNTHETIC POLYPEPTIDE

<400> SEQUENCE: 6

Cys Gly Gly Gly
1

<210> SEQ ID NO 7
<211> LENGTH: 6
<212> TYPE: PRT
<213> ORGANISM: Artificial Sequence
<220> FEATURE:
<223> OTHER INFORMATION: SYNTHETIC 6xHis TAG

<400> SEQUENCE: 7

His His His His His His
1               5
```